(12) United States Patent
Michielin et al.

(10) Patent No.: US 11,738,049 B2
(45) Date of Patent: Aug. 29, 2023

(54) KINASE MUTANTS AND USES THEREOF

(71) Applicants: SIB Swiss Institute of Bioinformatics, Lausanne (CH); CHUV—Centre Hospitalier Universitaire Vaudois, Lausanne (CH); Universite de Lausanne, Lausanne (CH); Ludwig Institute for Cancer Research Ltd, Zurich (CH)

(72) Inventors: Olivier Michielin, Lausanne (CH); Vincent Zoete, Morges (CH); George Coukos, Chexbres (CH); Melita Irving, Prilly (CH); Nahzli Dilek, Collombey (CH); Patrick Reichenbach, La Sarraz (CH); Kelly Ascencao, Prilly (CH)

(73) Assignees: SIB Swiss Institute of Bioinformatics, Lausanne (CH); CHUV—Centre Hospitalier Universitaire Vaudois, Lausanne (CH); Université de Lausanne, Lausanne (CH); Ludwig Institute for Cancer Research Ltd, New York, NY (US)

( * ) Notice: Subject to any disclaimer, the term of this patent is extended or adjusted under 35 U.S.C. 154(b) by 758 days.

(21) Appl. No.: 16/615,032

(22) PCT Filed: May 24, 2018

(86) PCT No.: PCT/EP2018/063733
§ 371 (c)(1),
(2) Date: Nov. 19, 2019

(87) PCT Pub. No.: WO2018/215626
PCT Pub. Date: Nov. 29, 2018

(65) Prior Publication Data
US 2020/0101110 A1    Apr. 2, 2020

(30) Foreign Application Priority Data
May 24, 2017    (EP) .................................... 17172639

(51) Int. Cl.
| A61K 38/00 | (2006.01) |
| A61K 35/17 | (2015.01) |
| A61K 31/517 | (2006.01) |
| C07K 14/55 | (2006.01) |
| C12N 9/12 | (2006.01) |
| C12N 15/10 | (2006.01) |
| C12Q 1/48 | (2006.01) |
| G01N 33/573 | (2006.01) |

(52) U.S. Cl.
CPC ............ *A61K 35/17* (2013.01); *A61K 31/517* (2013.01); *C07K 14/55* (2013.01); *C12N 9/1205* (2013.01); *C12N 15/1024* (2013.01); *C12Q 1/485* (2013.01); *G01N 33/573* (2013.01); *A61K 38/00* (2013.01); *C12Y 207/10* (2013.01)

(58) Field of Classification Search
CPC ...................................................... A61K 38/43
See application file for complete search history.

(56) References Cited

U.S. PATENT DOCUMENTS

2012/0077827 A1    3/2012    Ibrahim et al.

FOREIGN PATENT DOCUMENTS

WO         00/42042 A2    7/2000

OTHER PUBLICATIONS

Mikayama et al. Proc. Natl. Acad. Sci. USA (1993) vol. 90, pp. 10056-10060.*
Voet et al. Biochemistry John Wiley & Sons, Inc., (1990), pp. 126-128 and 228-234.*
Susan E. Levin et al., "Inhibition of ZAP-70 Kinase Activity via an Analog-sensitive Allele Blocks T Cell Receptor and CD28 Superagonist Signaling", Journal of Biological Chemistry, vol. 283, No. 22, May 30, 2008, pp. 15419-15430.
H. Wang et al., "ZAP-70: An Essential Kinase in T-cell Signaling", Cold Spring Harbor Perspectives in Biology, vol. 2, No. 5, May 1, 2010.
Chao Zhang et al., "Structure-Guided Inhibitor Design Expands the Scope of Analog-Sensitive Kinase Technology", ACS Chemical Biology, vol. 8, No. 9, Sep. 20, 2013, pp. 1931-1938.
Bishop A C et al., "A chemical switch for inhibitor-sensitive alleles of any protein kinase", Nature, Macmillan Journals Ltd., ETC, vol. 407, Sep. 21, 2000, pp. 395-401.
B. B. Au-Yeung et al., "A sharp T-cell antigen receptor signaling threshold for T-cell proliferation", Proceedings National Academy of Sciences PNAS, vol. 111, No. 35, Aug. 18, 2014, pp. E3679-E3688.
Byron B Au-Yeung et al., "A genetically selective inhibitor demonstrates a function for the kinase Zap70 in regulatory T cells independent of its catalytic activity", Nature Immunology, vol. 11, No. 12, Oct. 31, 2010, pp. 1085-1092.
Michal Vieth et al., "Kinase Inhibitor Data Modeling and de Novo Inhibitor Design with Fragment Approaches", Journal of Medicinal Chemistry, vol. 52, No. 20, Oct. 22, 2009, pp. 6456-6466.
Chin Y Liew et al., "SVM Model for Virtual Screening of Lck Inhibitors", Journal of Chemical Information and Mode, American Chemical Society, Washington, DC, vol. 49, No. 4, Apr. 27, 2009, pp. 877-888.

(Continued)

*Primary Examiner* — Prema M Mertz
(74) *Attorney, Agent, or Firm* — Fox Rothschild LLP

(57) ABSTRACT

The present invention relates to methods of designing kinase mutants for reprogramming the sensitivity of a target kinase to some specific inhibitors, methods of reprogramming the sensitivity of a target kinase to some specific inhibitors, wherein those kinase inhibitors have little or no affinity for the wild-type target kinase, vectors or cells expressing said mutated kinases, composition and uses thereof for the prevention and/or treatment of a disease or disorder, in particular cancer.

6 Claims, 6 Drawing Sheets
Specification includes a Sequence Listing.

(56) References Cited

OTHER PUBLICATIONS

K C Lee et al., "Lck is a key target of imatinib and dasatinib in T-cell activation", Leukemia, vol. 24, No. 4, Apr. 1, 2010, pp. 896-900.
A. Giannini et al., "Regulation of the Src Family Kinase Lck by Hsp90 and Ubiquitination", Molecular and Cellular Biology, vol. 24, No. 13, Jul. 1, 2004, pp. 5667-5676.
Anthony C. Bishop et al., "Design of allele-specific inhibitors to probe protein kinase signaling", Current Biology, vol. 8, No. 5, Feb. 1, 1998, pp. 257-266.
A. Denzel et al., "Cutting Edge: A Chemical Genetic System for the Analysis of Kinases Regulating T Cell Development", The Journal of Immunology, 2003, 171:519-523.

* cited by examiner

SEQUENCE LISTING

<160> NUMBER OF SEQ ID NOS: 20

<210> SEQ ID NO 1
<211> LENGTH: 619
<212> TYPE: PRT
<213> ORGANISM: Homo sapiens

<400> SEQUENCE: 1

Met Pro Asp Pro Ala Ala His Leu Pro Phe Phe Tyr Gly Ser Ile Ser
1               5                   10                  15

Arg Ala Glu Ala Glu Glu His Leu Lys Leu Ala Gly Met Ala Asp Gly
                20                  25                  30

Leu Phe Leu Leu Arg Gln Cys Leu Arg Ser Leu Gly Gly Tyr Val Leu
            35                  40                  45

Ser Leu Val His Asp Val Arg Phe His His Phe Pro Ile Glu Arg Gln
        50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
                100                 105                 110

Gly Val Phe Asp Cys Leu Arg Asp Ala Met Val Arg Asp Tyr Val Arg
            115                 120                 125

Gln Thr Trp Lys Leu Glu Gly Glu Ala Leu Glu Gln Ala Ile Ile Ser
        130                 135                 140

Gln Ala Pro Gln Val Glu Lys Leu Ile Ala Thr Thr Ala His Glu Arg
145                 150                 155                 160

Met Pro Trp Tyr His Ser Ser Leu Thr Arg Glu Glu Ala Glu Arg Lys

```
              165                 170                 175
Leu Tyr Ser Gly Ala Gln Thr Asp Gly Lys Phe Leu Leu Arg Pro Arg
            180                 185                 190

Lys Glu Gln Gly Thr Tyr Ala Leu Ser Leu Ile Tyr Gly Lys Thr Val
            195                 200                 205

Tyr His Tyr Leu Ile Ser Gln Asp Lys Ala Gly Lys Tyr Cys Ile Pro
210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
            245                 250                 255

Ser Ser Ala Ser Asn Ala Ser Gly Ala Ala Pro Thr Leu Pro Ala
            260                 265                 270

His Pro Ser Thr Leu Thr His Pro Gln Arg Arg Ile Asp Thr Leu Asn
            275                 280                 285

Ser Asp Gly Tyr Thr Pro Glu Pro Ala Arg Ile Thr Ser Pro Asp Lys
            290                 295                 300

Pro Arg Pro Met Pro Met Asp Thr Ser Val Tyr Glu Ser Pro Tyr Ser
305                 310                 315                 320

Asp Pro Glu Glu Leu Lys Asp Lys Lys Leu Phe Leu Lys Arg Asp Asn
            325                 330                 335

Leu Leu Ile Ala Asp Ile Glu Leu Gly Cys Gly Asn Phe Gly Ser Val
            340                 345                 350

Arg Gln Gly Val Tyr Arg Met Arg Lys Lys Gln Ile Asp Val Ala Ile
            355                 360                 365

Lys Val Leu Lys Gln Gly Thr Glu Lys Ala Asp Thr Glu Glu Met Met
            370                 375                 380

Arg Glu Ala Gln Ile Met His Gln Leu Asp Asn Pro Tyr Ile Val Arg
385                 390                 395                 400

Leu Ile Gly Val Cys Gln Ala Glu Ala Leu Met Leu Val Met Glu Met
            405                 410                 415

Ala Gly Gly Gly Pro Leu His Lys Phe Leu Val Gly Lys Arg Glu Glu
            420                 425                 430

Ile Pro Val Ser Asn Val Ala Glu Leu Leu His Gln Val Ser Met Gly
            435                 440                 445

Met Lys Tyr Leu Glu Glu Lys Asn Phe Val His Arg Asp Leu Ala Ala
            450                 455                 460

Arg Asn Val Leu Leu Val Asn Arg His Tyr Ala Lys Ile Ser Asp Phe
465                 470                 475                 480

Gly Leu Ser Lys Ala Leu Gly Ala Asp Asp Ser Tyr Tyr Thr Ala Arg
            485                 490                 495

Ser Ala Gly Lys Trp Pro Leu Lys Trp Tyr Ala Pro Glu Cys Ile Asn
            500                 505                 510

Phe Arg Lys Phe Ser Ser Arg Ser Asp Val Trp Ser Tyr Gly Val Thr
            515                 520                 525

Met Trp Glu Ala Leu Ser Tyr Gly Gln Lys Pro Tyr Lys Lys Met Lys
            530                 535                 540

Gly Pro Glu Val Met Ala Phe Ile Glu Gln Gly Lys Arg Met Glu Cys
545                 550                 555                 560

Pro Pro Glu Cys Pro Pro Glu Leu Tyr Ala Leu Met Ser Asp Cys Trp
            565                 570                 575

Ile Tyr Lys Trp Glu Asp Arg Pro Asp Phe Leu Thr Val Glu Gln Arg
            580                 585                 590
```

```
Met Arg Ala Cys Tyr Tyr Ser Leu Ala Ser Lys Val Glu Gly Pro Pro
            595                 600                 605

Gly Ser Thr Gln Lys Ala Glu Ala Ala Cys Ala
        610                 615

<210> SEQ ID NO 2
<211> LENGTH: 509
<212> TYPE: PRT
<213> ORGANISM: Homo sapiens

<400> SEQUENCE: 2

Met Gly Cys Gly Cys Ser Ser His Pro Glu Asp Asp Trp Met Glu Asn
1               5                   10                  15

Ile Asp Val Cys Glu Asn Cys His Tyr Pro Ile Val Pro Leu Asp Gly
            20                  25                  30

Lys Gly Thr Leu Leu Ile Arg Asn Gly Ser Glu Val Arg Asp Pro Leu
        35                  40                  45

Val Thr Tyr Glu Gly Ser Asn Pro Pro Ala Ser Pro Leu Gln Asp Asn
    50                  55                  60

Leu Val Ile Ala Leu His Ser Tyr Glu Pro Ser His Asp Gly Asp Leu
65                  70                  75                  80

Gly Phe Glu Lys Gly Glu Gln Leu Arg Ile Leu Glu Gln Ser Gly Glu
                85                  90                  95

Trp Trp Lys Ala Gln Ser Leu Thr Thr Gly Gln Glu Gly Phe Ile Pro
            100                 105                 110

Phe Asn Phe Val Ala Lys Ala Asn Ser Leu Glu Pro Glu Pro Trp Phe
        115                 120                 125

Phe Lys Asn Leu Ser Arg Lys Asp Ala Glu Arg Gln Leu Leu Ala Pro
    130                 135                 140

Gly Asn Thr His Gly Ser Phe Leu Ile Arg Glu Ser Glu Ser Thr Ala
145                 150                 155                 160

Gly Ser Phe Ser Leu Ser Val Arg Asp Phe Asp Gln Asn Gln Gly Glu
                165                 170                 175

Val Val Lys His Tyr Lys Ile Arg Asn Leu Asp Asn Gly Gly Phe Tyr
            180                 185                 190

Ile Ser Pro Arg Ile Thr Phe Pro Gly Leu His Glu Leu Val Arg His
        195                 200                 205

Tyr Thr Asn Ala Ser Asp Gly Leu Cys Thr Arg Leu Ser Arg Pro Cys
    210                 215                 220

Gln Thr Gln Lys Pro Gln Lys Pro Trp Trp Glu Asp Glu Trp Glu Val
225                 230                 235                 240

Pro Arg Glu Thr Leu Lys Leu Val Glu Arg Leu Gly Ala Gly Gln Phe
                245                 250                 255

Gly Glu Val Trp Met Gly Tyr Tyr Asn Gly His Thr Lys Val Ala Val
            260                 265                 270

Lys Ser Leu Lys Gln Gly Ser Met Ser Pro Asp Ala Phe Leu Ala Glu
        275                 280                 285

Ala Asn Leu Met Lys Gln Leu Gln His Gln Arg Leu Val Arg Leu Tyr
    290                 295                 300

Ala Val Val Thr Gln Glu Pro Ile Tyr Ile Thr Glu Tyr Met Glu
305                 310                 315                 320

Asn Gly Ser Leu Val Asp Phe Leu Lys Thr Pro Ser Gly Ile Lys Leu
                325                 330                 335

Thr Ile Asn Lys Leu Leu Asp Met Ala Ala Gln Ile Ala Glu Gly Met
```

```
                    340                 345                 350
Ala Phe Ile Glu Glu Arg Asn Tyr Ile His Arg Asp Leu Arg Ala Ala
            355                 360                 365

Asn Ile Leu Val Ser Asp Thr Leu Ser Cys Lys Ile Ala Asp Phe Gly
        370                 375                 380

Leu Ala Arg Leu Ile Glu Asp Asn Glu Tyr Thr Ala Arg Glu Gly Ala
385                 390                 395                 400

Lys Phe Pro Ile Lys Trp Thr Ala Pro Glu Ala Ile Asn Tyr Gly Thr
                405                 410                 415

Phe Thr Ile Lys Ser Asp Val Trp Ser Phe Gly Ile Leu Leu Thr Glu
            420                 425                 430

Ile Val Thr His Gly Arg Ile Pro Tyr Pro Gly Met Thr Asn Pro Glu
        435                 440                 445

Val Ile Gln Asn Leu Glu Arg Gly Tyr Arg Met Val Arg Pro Asp Asn
    450                 455                 460

Cys Pro Glu Glu Leu Tyr Gln Leu Met Arg Leu Cys Trp Lys Glu Arg
465                 470                 475                 480

Pro Glu Asp Arg Pro Thr Phe Asp Tyr Leu Arg Ser Val Leu Glu Asp
                485                 490                 495

Phe Phe Thr Ala Thr Glu Gly Gln Tyr Gln Pro Gln Pro
            500                 505

<210> SEQ ID NO 3
<211> LENGTH: 619
<212> TYPE: PRT
<213> ORGANISM: Artificial Sequence
<220> FEATURE:
<223> OTHER INFORMATION: Amino acid sequence of Z1 (mutated human
      Zap-70)

<400> SEQUENCE: 3

Met Pro Asp Pro Ala Ala His Leu Pro Phe Phe Tyr Gly Ser Ile Ser
1               5                   10                  15

Arg Ala Glu Ala Glu His Leu Lys Leu Ala Gly Met Ala Asp Gly
            20                  25                  30

Leu Phe Leu Leu Arg Gln Cys Leu Arg Ser Leu Gly Gly Tyr Val Leu
        35                  40                  45

Ser Leu Val His Asp Val Arg Phe His His Phe Pro Ile Glu Arg Gln
    50                  55                  60

Leu Asn Gly Thr Tyr Ala Ile Ala Gly Gly Lys Ala His Cys Gly Pro
65              70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
            100                 105                 110

Gly Val Phe Asp Cys Leu Arg Asp Ala Met Val Arg Asp Tyr Val Arg
        115                 120                 125

Gln Thr Trp Lys Leu Glu Gly Glu Ala Leu Glu Gln Ala Ile Ile Ser
    130                 135                 140

Gln Ala Pro Gln Val Glu Lys Leu Ile Ala Thr Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Ala Gln Thr Asp Gly Lys Phe Leu Leu Arg Pro Arg
            180                 185                 190
```

```
Lys Glu Gln Gly Thr Tyr Ala Leu Ser Leu Ile Tyr Gly Lys Thr Val
            195                 200                 205
Tyr His Tyr Leu Ile Ser Gln Asp Lys Ala Gly Lys Tyr Cys Ile Pro
        210                 215                 220
Glu Gly Thr Lys Phe Asp Thr Leu Trp Gln Leu Val Glu Tyr Leu Lys
225                 230                 235                 240
Leu Lys Ala Asp Gly Leu Ile Tyr Cys Leu Lys Glu Ala Cys Pro Asn
                245                 250                 255
Ser Ser Ala Ser Asn Ala Ser Gly Ala Ala Pro Thr Leu Pro Ala
            260                 265                 270
His Pro Ser Thr Leu Thr His Pro Gln Arg Arg Ile Asp Thr Leu Asn
        275                 280                 285
Ser Asp Gly Tyr Thr Pro Glu Pro Ala Arg Ile Thr Ser Pro Asp Lys
    290                 295                 300
Pro Arg Pro Met Pro Met Asp Thr Ser Val Tyr Glu Ser Pro Tyr Ser
305                 310                 315                 320
Asp Pro Glu Glu Leu Lys Asp Lys Lys Leu Phe Leu Lys Arg Asp Asn
                325                 330                 335
Leu Leu Ile Ala Asp Ile Glu Leu Gly Cys Gly Asn Phe Gly Ser Val
            340                 345                 350
Arg Gln Gly Val Tyr Arg Met Arg Lys Lys Gln Ile Asp Val Ala Ile
        355                 360                 365
Lys Val Leu Lys Gln Gly Thr Glu Lys Ala Asp Thr Glu Glu Met Met
    370                 375                 380
Arg Glu Ala Gln Ile Met His Gln Leu Asp Asn Pro Tyr Ile Val Arg
385                 390                 395                 400
Leu Ile Gly Val Cys Gln Ala Glu Ala Leu Met Leu Val Ala Glu Met
                405                 410                 415
Ala Gly Gly Gly Pro Leu His Lys Phe Leu Val Gly Lys Arg Glu Glu
            420                 425                 430
Ile Pro Val Ser Asn Val Ala Glu Leu Leu His Gln Val Ser Met Gly
        435                 440                 445
Met Lys Tyr Leu Glu Glu Lys Asn Phe Val His Arg Asp Leu Ala Ala
    450                 455                 460
Arg Asn Val Leu Leu Val Asn Arg His Tyr Ala Lys Ile Ser Asp Phe
465                 470                 475                 480
Gly Leu Ser Lys Ala Leu Gly Ala Asp Asp Ser Tyr Tyr Thr Ala Arg
                485                 490                 495
Ser Ala Gly Lys Trp Pro Leu Lys Trp Tyr Ala Pro Glu Cys Ile Asn
            500                 505                 510
Phe Arg Lys Phe Ser Ser Arg Ser Asp Val Trp Ser Tyr Gly Val Thr
        515                 520                 525
Met Trp Glu Ala Leu Ser Tyr Gly Gln Lys Pro Tyr Lys Lys Met Lys
    530                 535                 540
Gly Pro Glu Val Met Ala Phe Ile Glu Gln Gly Lys Arg Met Glu Cys
545                 550                 555                 560
Pro Pro Glu Cys Pro Pro Glu Leu Tyr Ala Leu Met Ser Asp Cys Trp
                565                 570                 575
Ile Tyr Lys Trp Glu Asp Arg Pro Asp Phe Leu Thr Val Glu Gln Arg
            580                 585                 590
Met Arg Ala Cys Tyr Tyr Ser Leu Ala Ser Lys Val Glu Gly Pro Pro
        595                 600                 605
Gly Ser Thr Gln Lys Ala Glu Ala Ala Cys Ala
```

610            615

<210> SEQ ID NO 4
<211> LENGTH: 619
<212> TYPE: PRT
<213> ORGANISM: Artificial Sequence
<220> FEATURE:
<223> OTHER INFORMATION: Amino acid sequence of Z2 (mutated human
      Zap-70)

<400> SEQUENCE: 4

Met Pro Asp Pro Ala Ala His Leu Pro Phe Phe Tyr Gly Ser Ile Ser
1               5                   10                  15

Arg Ala Glu Ala Glu His Leu Lys Leu Ala Gly Met Ala Asp Gly
            20                  25                  30

Leu Phe Leu Leu Arg Gln Cys Leu Arg Ser Leu Gly Gly Tyr Val Leu
        35                  40                  45

Ser Leu Val His Asp Val Arg Phe His His Phe Pro Ile Glu Arg Gln
    50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
            100                 105                 110

Gly Val Phe Asp Cys Leu Arg Asp Ala Met Val Arg Asp Tyr Val Arg
        115                 120                 125

Gln Thr Trp Lys Leu Glu Gly Glu Ala Leu Glu Gln Ala Ile Ile Ser
    130                 135                 140

Gln Ala Pro Gln Val Glu Lys Leu Ile Ala Thr Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Ala Gln Thr Asp Gly Lys Phe Leu Leu Arg Pro Arg
            180                 185                 190

Lys Glu Gln Gly Thr Tyr Ala Leu Ser Leu Ile Tyr Gly Lys Thr Val
        195                 200                 205

Tyr His Tyr Leu Ile Ser Gln Asp Lys Ala Gly Lys Tyr Cys Ile Pro
    210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255

Ser Ser Ala Ser Asn Ala Ser Gly Ala Ala Pro Thr Leu Pro Ala
            260                 265                 270

His Pro Ser Thr Leu Thr His Pro Gln Arg Arg Ile Asp Thr Leu Asn
        275                 280                 285

Ser Asp Gly Tyr Thr Pro Glu Pro Ala Arg Ile Thr Ser Pro Asp Lys
    290                 295                 300

Pro Arg Pro Met Pro Met Asp Thr Ser Val Tyr Glu Ser Pro Tyr Ser
305                 310                 315                 320

Asp Pro Glu Glu Leu Lys Asp Lys Lys Leu Phe Leu Lys Arg Asp Asn
                325                 330                 335

Leu Leu Ile Ala Asp Ile Glu Leu Gly Cys Gly Asn Phe Gly Ser Val
            340                 345                 350

```
Arg Gln Gly Val Tyr Arg Met Arg Lys Lys Gln Ile Asp Val Ala Ile
            355                 360                 365

Lys Val Leu Lys Gln Gly Thr Glu Lys Ala Asp Thr Glu Glu Met Met
            370                 375                 380

Arg Glu Ala Gln Ile Met His Gln Leu Asp Asn Pro Tyr Ile Val Arg
385                 390                 395                 400

Leu Ile Gly Val Cys Gln Ala Glu Ala Leu Met Leu Val Thr Glu Met
                405                 410                 415

Ala Gly Gly Gly Pro Leu His Lys Phe Leu Val Gly Lys Arg Glu Glu
            420                 425                 430

Ile Pro Val Ser Asn Val Ala Glu Leu Leu His Gln Val Ser Met Gly
            435                 440                 445

Met Lys Tyr Leu Glu Glu Lys Asn Phe Val His Arg Asp Leu Ala Ala
            450                 455                 460

Arg Asn Val Leu Leu Val Asn Arg His Tyr Ala Lys Ile Ser Asp Phe
465                 470                 475                 480

Gly Leu Ser Lys Ala Leu Gly Ala Asp Asp Ser Tyr Tyr Thr Ala Arg
                485                 490                 495

Ser Ala Gly Lys Trp Pro Leu Lys Trp Tyr Ala Pro Glu Cys Ile Asn
            500                 505                 510

Phe Arg Lys Phe Ser Ser Arg Ser Asp Val Trp Ser Tyr Gly Val Thr
            515                 520                 525

Met Trp Glu Ala Leu Ser Tyr Gly Gln Lys Pro Tyr Lys Lys Met Lys
            530                 535                 540

Gly Pro Glu Val Met Ala Phe Ile Glu Gln Gly Lys Arg Met Glu Cys
545                 550                 555                 560

Pro Pro Glu Cys Pro Pro Glu Leu Tyr Ala Leu Met Ser Asp Cys Trp
                565                 570                 575

Ile Tyr Lys Trp Glu Asp Arg Pro Asp Phe Leu Thr Val Glu Gln Arg
            580                 585                 590

Met Arg Ala Cys Tyr Tyr Ser Leu Ala Ser Lys Val Glu Gly Pro Pro
            595                 600                 605

Gly Ser Thr Gln Lys Ala Glu Ala Ala Cys Ala
        610                 615

<210> SEQ ID NO 5
<211> LENGTH: 619
<212> TYPE: PRT
<213> ORGANISM: Artificial Sequence
<220> FEATURE:
<223> OTHER INFORMATION: Amino acid sequence of Z3 (mutated human
      Zap-70)

<400> SEQUENCE: 5

Met Pro Asp Pro Ala Ala His Leu Pro Phe Phe Tyr Gly Ser Ile Ser
1               5                   10                  15

Arg Ala Glu Ala Glu Glu His Leu Lys Leu Ala Gly Met Ala Asp Gly
            20                  25                  30

Leu Phe Leu Leu Arg Gln Cys Leu Arg Ser Leu Gly Gly Tyr Val Leu
            35                  40                  45

Ser Leu Val His Asp Val Arg Phe His His Phe Pro Ile Glu Arg Gln
            50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
                85                  90                  95
```

```
Asn Leu Arg Lys Pro Cys Asn Arg Pro Ser Gly Leu Glu Pro Gln Pro
            100                 105                 110

Gly Val Phe Asp Cys Leu Arg Asp Ala Met Val Arg Asp Tyr Val Arg
        115                 120                 125

Gln Thr Trp Lys Leu Glu Gly Glu Ala Leu Glu Gln Ala Ile Ile Ser
    130                 135                 140

Gln Ala Pro Gln Val Glu Lys Leu Ile Ala Thr Thr Ala His Glu Arg
145                 150                 155                 160

Met Pro Trp Tyr His Ser Ser Leu Thr Arg Glu Ala Glu Arg Lys
                165                 170                 175

Leu Tyr Ser Gly Ala Gln Thr Asp Gly Lys Phe Leu Leu Arg Pro Arg
                180                 185                 190

Lys Glu Gln Gly Thr Tyr Ala Leu Ser Leu Ile Tyr Gly Lys Thr Val
            195                 200                 205

Tyr His Tyr Leu Ile Ser Gln Asp Lys Ala Gly Lys Tyr Cys Ile Pro
        210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255

Ser Ser Ala Ser Asn Ala Ser Gly Ala Ala Pro Thr Leu Pro Ala
                260                 265                 270

His Pro Ser Thr Leu Thr His Pro Gln Arg Ile Asp Thr Leu Asn
        275                 280                 285

Ser Asp Gly Tyr Thr Pro Glu Pro Ala Arg Ile Thr Ser Pro Asp Lys
        290                 295                 300

Pro Arg Pro Met Pro Met Asp Thr Ser Val Tyr Glu Ser Pro Tyr Ser
305                 310                 315                 320

Asp Pro Glu Glu Leu Lys Asp Lys Lys Leu Phe Leu Lys Arg Asp Asn
                325                 330                 335

Leu Leu Ile Ala Asp Ile Glu Leu Gly Cys Gly Asn Phe Gly Ser Val
            340                 345                 350

Arg Gln Gly Val Tyr Arg Met Arg Lys Lys Gln Ile Asp Val Ala Ile
        355                 360                 365

Lys Val Leu Lys Gln Gly Thr Glu Lys Ala Asp Thr Glu Glu Met Met
    370                 375                 380

Arg Glu Ala Gln Ile Met His Gln Leu Asp Asn Pro Tyr Ile Val Arg
385                 390                 395                 400

Leu Ile Gly Val Cys Gln Ala Glu Ala Leu Met Leu Val Val Glu Met
                405                 410                 415

Ala Gly Gly Gly Pro Leu His Lys Phe Leu Val Gly Lys Arg Glu Glu
            420                 425                 430

Ile Pro Val Ser Asn Val Ala Glu Leu Leu His Gln Val Ser Met Gly
        435                 440                 445

Met Lys Tyr Leu Glu Glu Lys Asn Phe Val His Arg Asp Leu Ala Ala
    450                 455                 460

Arg Asn Val Leu Leu Val Asn Arg His Tyr Ala Lys Ile Ser Asp Phe
465                 470                 475                 480

Gly Leu Ser Lys Ala Leu Gly Ala Asp Asp Ser Tyr Tyr Thr Ala Arg
                485                 490                 495

Ser Ala Gly Lys Trp Pro Leu Lys Trp Tyr Ala Pro Glu Cys Ile Asn
            500                 505                 510
```

```
Phe Arg Lys Phe Ser Ser Arg Ser Asp Val Trp Ser Tyr Gly Val Thr
            515                 520                 525
Met Trp Glu Ala Leu Ser Tyr Gly Gln Lys Pro Tyr Lys Lys Met Lys
530                 535                 540
Gly Pro Glu Val Met Ala Phe Ile Glu Gln Gly Lys Arg Met Glu Cys
545                 550                 555                 560
Pro Pro Glu Cys Pro Pro Glu Leu Tyr Ala Leu Met Ser Asp Cys Trp
                565                 570                 575
Ile Tyr Lys Trp Glu Asp Arg Pro Asp Phe Leu Thr Val Glu Gln Arg
            580                 585                 590
Met Arg Ala Cys Tyr Tyr Ser Leu Ala Ser Lys Val Glu Gly Pro Pro
        595                 600                 605
Gly Ser Thr Gln Lys Ala Glu Ala Ala Cys Ala
    610                 615

<210> SEQ ID NO 6
<211> LENGTH: 619
<212> TYPE: PRT
<213> ORGANISM: Artificial Sequence
<220> FEATURE:
<223> OTHER INFORMATION: Amino acid sequence of Z8 (mutated human
      Zap-70)

<400> SEQUENCE: 6

Met Pro Asp Pro Ala Ala His Leu Pro Phe Phe Tyr Gly Ser Ile Ser
1               5                   10                  15
Arg Ala Glu Ala Glu Glu His Leu Lys Leu Ala Gly Met Ala Asp Gly
            20                  25                  30
Leu Phe Leu Leu Arg Gln Cys Leu Arg Ser Leu Gly Gly Tyr Val Leu
        35                  40                  45
Ser Leu Val His Asp Val Arg Phe His His Phe Pro Ile Glu Arg Gln
    50                  55                  60
Leu Asn Gly Thr Tyr Ala Ile Ala Gly Gly Lys Ala His Cys Gly Pro
65                  70                  75                  80
Ala Glu Leu Cys Glu Phe Tyr Ser Arg Asp Pro Asp Gly Leu Pro Cys
                85                  90                  95
Asn Leu Arg Lys Pro Cys Asn Arg Pro Ser Gly Leu Glu Pro Gln Pro
            100                 105                 110
Gly Val Phe Asp Cys Leu Arg Asp Ala Met Val Arg Asp Tyr Val Arg
        115                 120                 125
Gln Thr Trp Lys Leu Glu Gly Glu Ala Leu Glu Gln Ala Ile Ile Ser
    130                 135                 140
Gln Ala Pro Gln Val Glu Lys Leu Ile Ala Thr Ala His Glu Arg
145                 150                 155                 160
Met Pro Trp Tyr His Ser Ser Leu Thr Arg Glu Glu Ala Glu Arg Lys
                165                 170                 175
Leu Tyr Ser Gly Ala Gln Thr Asp Gly Lys Phe Leu Leu Arg Pro Arg
            180                 185                 190
Lys Glu Gln Gly Thr Tyr Ala Leu Ser Leu Ile Tyr Gly Lys Thr Val
        195                 200                 205
Tyr His Tyr Leu Ile Ser Gln Asp Lys Ala Gly Lys Tyr Cys Ile Pro
    210                 215                 220
Glu Gly Thr Lys Phe Asp Thr Leu Trp Gln Leu Val Glu Tyr Leu Lys
225                 230                 235                 240
Leu Lys Ala Asp Gly Leu Ile Tyr Cys Leu Lys Glu Ala Cys Pro Asn
                245                 250                 255
```

```
Ser Ser Ala Ser Asn Ala Ser Gly Ala Ala Pro Thr Leu Pro Ala
            260                 265                 270

His Pro Ser Thr Leu Thr His Pro Gln Arg Arg Ile Asp Thr Leu Asn
        275                 280                 285

Ser Asp Gly Tyr Thr Pro Glu Pro Ala Arg Ile Thr Ser Pro Asp Lys
    290                 295                 300

Pro Arg Pro Met Pro Met Asp Thr Ser Val Tyr Glu Ser Pro Tyr Ser
305                 310                 315                 320

Asp Pro Glu Glu Leu Lys Asp Lys Lys Leu Phe Leu Lys Arg Asp Asn
                325                 330                 335

Leu Leu Ile Ala Asp Ile Glu Leu Gly Cys Gly Asn Phe Gly Ser Val
            340                 345                 350

Arg Gln Gly Val Tyr Arg Met Arg Lys Lys Gln Ile Asp Val Ala Ile
        355                 360                 365

Lys Val Leu Lys Gln Gly Thr Glu Lys Ala Asp Thr Glu Glu Met Met
    370                 375                 380

Arg Glu Ala Gln Ile Met His Gln Leu Asp Asn Pro Tyr Ile Val Arg
385                 390                 395                 400

Leu Ile Gly Val Cys Gln Ala Glu Ala Leu Met Leu Val Val Glu Tyr
                405                 410                 415

Ala Gly Gly Gly Pro Leu His Lys Phe Leu Val Gly Lys Arg Glu Glu
            420                 425                 430

Ile Pro Val Ser Asn Val Ala Glu Leu Leu His Gln Val Ser Met Gly
        435                 440                 445

Met Lys Tyr Leu Glu Glu Lys Asn Phe Val His Arg Asp Leu Ala Ala
    450                 455                 460

Arg Asn Val Leu Leu Val Asn Arg His Tyr Ala Lys Ile Ser Asp Phe
465                 470                 475                 480

Gly Leu Ser Lys Ala Leu Gly Ala Asp Asp Ser Tyr Tyr Thr Ala Arg
                485                 490                 495

Ser Ala Gly Lys Trp Pro Leu Lys Trp Tyr Ala Pro Glu Cys Ile Asn
            500                 505                 510

Phe Arg Lys Phe Ser Ser Arg Ser Asp Val Trp Ser Tyr Gly Val Thr
        515                 520                 525

Met Trp Glu Ala Leu Ser Tyr Gly Gln Lys Pro Tyr Lys Lys Met Lys
    530                 535                 540

Gly Pro Glu Val Met Ala Phe Ile Glu Gln Gly Lys Arg Met Glu Cys
545                 550                 555                 560

Pro Pro Glu Cys Pro Pro Glu Leu Tyr Ala Leu Met Ser Asp Cys Trp
                565                 570                 575

Ile Tyr Lys Trp Glu Asp Arg Pro Asp Phe Leu Thr Val Glu Gln Arg
            580                 585                 590

Met Arg Ala Cys Tyr Tyr Ser Leu Ala Ser Lys Val Glu Gly Pro Pro
        595                 600                 605

Gly Ser Thr Gln Lys Ala Glu Ala Ala Cys Ala
    610                 615

<210> SEQ ID NO 7
<211> LENGTH: 619
<212> TYPE: PRT
<213> ORGANISM: Artificial Sequence
<220> FEATURE:
<223> OTHER INFORMATION: Amino acid sequence of Z9 (mutated human
      Zap-70)
```

<400> SEQUENCE: 7

```
Met Pro Asp Pro Ala Ala His Leu Pro Phe Phe Tyr Gly Ser Ile Ser
1               5                   10                  15

Arg Ala Glu Ala Glu His Leu Lys Leu Ala Gly Met Ala Asp Gly
            20                  25                  30

Leu Phe Leu Leu Arg Gln Cys Leu Arg Ser Leu Gly Gly Tyr Val Leu
        35                  40                  45

Ser Leu Val His Asp Val Arg Phe His His Phe Pro Ile Glu Arg Gln
    50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
            100                 105                 110

Gly Val Phe Asp Cys Leu Arg Asp Ala Met Val Arg Asp Tyr Val Arg
        115                 120                 125

Gln Thr Trp Lys Leu Glu Gly Glu Ala Leu Glu Gln Ala Ile Ile Ser
    130                 135                 140

Gln Ala Pro Gln Val Glu Lys Leu Ile Ala Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Ala Gln Thr Asp Gly Lys Phe Leu Leu Arg Pro Arg
            180                 185                 190

Lys Glu Gln Gly Thr Tyr Ala Leu Ser Leu Ile Tyr Gly Lys Thr Val
        195                 200                 205

Tyr His Tyr Leu Ile Ser Gln Asp Lys Ala Gly Lys Tyr Cys Ile Pro
    210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255

Ser Ser Ala Ser Asn Ala Ser Gly Ala Ala Pro Thr Leu Pro Ala
            260                 265                 270

His Pro Ser Thr Leu Thr His Pro Gln Arg Arg Ile Asp Thr Leu Asn
        275                 280                 285

Ser Asp Gly Tyr Thr Pro Glu Pro Ala Arg Ile Thr Ser Pro Asp Lys
    290                 295                 300

Pro Arg Pro Met Pro Met Asp Thr Ser Val Tyr Glu Ser Pro Tyr Ser
305                 310                 315                 320

Asp Pro Glu Glu Leu Lys Asp Lys Lys Leu Phe Leu Lys Arg Asp Asn
                325                 330                 335

Leu Leu Ile Ala Asp Ile Glu Leu Gly Cys Gly Asn Phe Gly Ser Val
            340                 345                 350

Arg Gln Gly Val Tyr Arg Met Arg Lys Lys Gln Ile Asp Val Ala Ile
        355                 360                 365

Lys Val Leu Lys Gln Gly Thr Glu Lys Ala Asp Thr Glu Glu Met Met
    370                 375                 380

Arg Glu Ala Gln Ile Met His Gln Leu Asp Asn Pro Tyr Ile Ile Arg
385                 390                 395                 400

Leu Ile Gly Val Cys Gln Ala Glu Ala Leu Met Leu Val Val Glu Met
                405                 410                 415
```

-continued

```
Ala Gly Gly Pro Leu His Lys Phe Leu Val Gly Lys Arg Glu Glu
        420                 425                 430

Ile Pro Val Ser Asn Val Ala Glu Leu Leu His Gln Val Ser Met Gly
            435                 440                 445

Met Lys Tyr Leu Glu Glu Lys Asn Phe Val His Arg Asp Leu Ala Ala
    450                 455                 460

Arg Asn Val Leu Leu Val Asn Arg His Tyr Ala Lys Ile Ser Asp Phe
465                 470                 475                 480

Gly Leu Ser Lys Ala Leu Gly Ala Asp Asp Ser Tyr Tyr Thr Ala Arg
                485                 490                 495

Ser Ala Gly Lys Trp Pro Leu Lys Trp Tyr Ala Pro Glu Cys Ile Asn
            500                 505                 510

Phe Arg Lys Phe Ser Ser Arg Ser Asp Val Trp Ser Tyr Gly Val Thr
        515                 520                 525

Met Trp Glu Ala Leu Ser Tyr Gly Gln Lys Pro Tyr Lys Lys Met Lys
    530                 535                 540

Gly Pro Glu Val Met Ala Phe Ile Glu Gln Gly Lys Arg Met Glu Cys
545                 550                 555                 560

Pro Pro Glu Cys Pro Pro Glu Leu Tyr Ala Leu Met Ser Asp Cys Trp
                565                 570                 575

Ile Tyr Lys Trp Glu Asp Arg Pro Asp Phe Leu Thr Val Glu Gln Arg
            580                 585                 590

Met Arg Ala Cys Tyr Tyr Ser Leu Ala Ser Lys Val Glu Gly Pro Pro
        595                 600                 605

Gly Ser Thr Gln Lys Ala Glu Ala Ala Cys Ala
    610                 615
```

<210> SEQ ID NO 8
<211> LENGTH: 619
<212> TYPE: PRT
<213> ORGANISM: Artificial Sequence
<220> FEATURE:
<223> OTHER INFORMATION: Amino acid sequence of Z10 (mutated human Zap-70)

<400> SEQUENCE: 8

```
Met Pro Asp Pro Ala Ala His Leu Pro Phe Phe Tyr Gly Ser Ile Ser
1               5                   10                  15

Arg Ala Glu Ala Glu His Leu Lys Leu Ala Gly Met Ala Asp Gly
            20                  25                  30

Leu Phe Leu Leu Arg Gln Cys Leu Arg Ser Leu Gly Gly Tyr Val Leu
        35                  40                  45

Ser Leu Val His Asp Val Arg Phe His His Phe Pro Ile Glu Arg Gln
    50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
            100                 105                 110

Gly Val Phe Asp Cys Leu Arg Asp Ala Met Val Arg Asp Tyr Val Arg
        115                 120                 125

Gln Thr Trp Lys Leu Glu Gly Glu Ala Leu Glu Gln Ala Ile Ile Ser
    130                 135                 140

Gln Ala Pro Gln Val Glu Lys Leu Ile Ala Thr Thr Ala His Glu Arg
```

```
                145                 150                 155                 160
Met Pro Trp Tyr His Ser Ser Leu Thr Arg Glu Glu Ala Glu Arg Lys
                    165                 170                 175
Leu Tyr Ser Gly Ala Gln Thr Asp Gly Lys Phe Leu Leu Arg Pro Arg
                    180                 185                 190
Lys Glu Gln Gly Thr Tyr Ala Leu Ser Leu Ile Tyr Gly Lys Thr Val
                    195                 200                 205
Tyr His Tyr Leu Ile Ser Gln Asp Lys Ala Gly Lys Tyr Cys Ile Pro
                    210                 215                 220
Glu Gly Thr Lys Phe Asp Thr Leu Trp Gln Leu Val Glu Tyr Leu Lys
225                 230                 235                 240
Leu Lys Ala Asp Gly Leu Ile Tyr Cys Leu Lys Glu Ala Cys Pro Asn
                    245                 250                 255
Ser Ser Ala Ser Asn Ala Ser Gly Ala Ala Pro Thr Leu Pro Ala
                    260                 265                 270
His Pro Ser Thr Leu Thr His Pro Gln Arg Arg Ile Asp Thr Leu Asn
                    275                 280                 285
Ser Asp Gly Tyr Thr Pro Glu Pro Ala Arg Ile Thr Ser Pro Asp Lys
                    290                 295                 300
Pro Arg Pro Met Pro Met Asp Thr Ser Val Tyr Glu Ser Pro Tyr Ser
305                 310                 315                 320
Asp Pro Glu Glu Leu Lys Asp Lys Lys Leu Phe Leu Lys Arg Asp Asn
                    325                 330                 335
Leu Leu Ile Ala Asp Ile Glu Leu Gly Cys Gly Asn Phe Gly Ser Val
                    340                 345                 350
Arg Gln Gly Val Tyr Arg Met Arg Lys Lys Gln Ile Asp Val Ala Ile
                    355                 360                 365
Lys Val Leu Lys Gln Gly Thr Glu Lys Ala Asp Thr Glu Glu Met Met
                    370                 375                 380
Arg Glu Ala Gln Ile Met His Gln Leu Asp Asn Pro Tyr Ile Ile Arg
385                 390                 395                 400
Leu Ile Gly Val Cys Gln Ala Glu Ala Leu Met Leu Val Val Glu Tyr
                    405                 410                 415
Ala Gly Gly Gly Pro Leu His Lys Phe Leu Val Gly Lys Arg Glu Glu
                    420                 425                 430
Ile Pro Val Ser Asn Val Ala Glu Leu Leu His Gln Val Ser Met Gly
                    435                 440                 445
Met Lys Tyr Leu Glu Glu Lys Asn Phe Val His Arg Asp Leu Ala Ala
                    450                 455                 460
Arg Asn Val Leu Leu Val Asn Arg His Tyr Ala Lys Ile Ser Asp Phe
465                 470                 475                 480
Gly Leu Ser Lys Ala Leu Gly Ala Asp Asp Ser Tyr Tyr Thr Ala Arg
                    485                 490                 495
Ser Ala Gly Lys Trp Pro Leu Lys Trp Tyr Ala Pro Glu Cys Ile Asn
                    500                 505                 510
Phe Arg Lys Phe Ser Ser Arg Ser Asp Val Trp Ser Tyr Gly Val Thr
                    515                 520                 525
Met Trp Glu Ala Leu Ser Tyr Gly Gln Lys Pro Tyr Lys Lys Met Lys
                    530                 535                 540
Gly Pro Glu Val Met Ala Phe Ile Glu Gln Gly Lys Arg Met Glu Cys
545                 550                 555                 560
Pro Pro Glu Cys Pro Pro Glu Leu Tyr Ala Leu Met Ser Asp Cys Trp
                    565                 570                 575
```

-continued

```
Ile Tyr Lys Trp Glu Asp Arg Pro Asp Phe Leu Thr Val Glu Gln Arg
            580                 585                 590

Met Arg Ala Cys Tyr Tyr Ser Leu Ala Ser Lys Val Glu Gly Pro Pro
        595                 600                 605

Gly Ser Thr Gln Lys Ala Glu Ala Ala Cys Ala
    610                 615

<210> SEQ ID NO 9
<211> LENGTH: 509
<212> TYPE: PRT
<213> ORGANISM: Artificial Sequence
<220> FEATURE:
<223> OTHER INFORMATION: Amino acid sequence of mutated human Lck 7
      (T316V)

<400> SEQUENCE: 9

Met Gly Cys Gly Cys Ser Ser His Pro Glu Asp Asp Trp Met Glu Asn
1               5                   10                  15

Ile Asp Val Cys Glu Asn Cys His Tyr Pro Ile Val Pro Leu Asp Gly
            20                  25                  30

Lys Gly Thr Leu Leu Ile Arg Asn Gly Ser Glu Val Arg Asp Pro Leu
        35                  40                  45

Val Thr Tyr Glu Gly Ser Asn Pro Pro Ala Ser Pro Leu Gln Asp Asn
    50                  55                  60

Leu Val Ile Ala Leu His Ser Tyr Glu Pro Ser His Asp Gly Asp Leu
65                  70                  75                  80

Gly Phe Glu Lys Gly Glu Gln Leu Arg Ile Leu Glu Gln Ser Gly Glu
                85                  90                  95

Trp Trp Lys Ala Gln Ser Leu Thr Thr Gly Gln Glu Gly Phe Ile Pro
            100                 105                 110

Phe Asn Phe Val Ala Lys Ala Asn Ser Leu Glu Pro Glu Pro Trp Phe
        115                 120                 125

Phe Lys Asn Leu Ser Arg Lys Asp Ala Glu Arg Gln Leu Leu Ala Pro
    130                 135                 140

Gly Asn Thr His Gly Ser Phe Leu Ile Arg Glu Ser Glu Ser Thr Ala
145                 150                 155                 160

Gly Ser Phe Ser Leu Ser Val Arg Asp Phe Asp Gln Asn Gln Gly Glu
                165                 170                 175

Val Val Lys His Tyr Lys Ile Arg Asn Leu Asp Asn Gly Gly Phe Tyr
            180                 185                 190

Ile Ser Pro Arg Ile Thr Phe Pro Gly Leu His Glu Leu Val Arg His
        195                 200                 205

Tyr Thr Asn Ala Ser Asp Gly Leu Cys Thr Arg Leu Ser Arg Pro Cys
    210                 215                 220

Gln Thr Gln Lys Pro Gln Lys Pro Trp Trp Glu Asp Glu Trp Glu Val
225                 230                 235                 240

Pro Arg Glu Thr Leu Lys Leu Val Glu Arg Leu Gly Ala Gly Gln Phe
                245                 250                 255

Gly Glu Val Trp Met Gly Tyr Tyr Asn Gly His Thr Lys Val Ala Val
            260                 265                 270

Lys Ser Leu Lys Gln Gly Ser Met Ser Pro Asp Ala Phe Leu Ala Glu
        275                 280                 285

Ala Asn Leu Met Lys Gln Leu Gln His Gln Arg Leu Val Arg Leu Tyr
    290                 295                 300

Ala Val Val Thr Gln Glu Pro Ile Tyr Ile Ile Val Glu Tyr Met Glu
```

-continued

```
                305                 310                 315                 320
        Asn Gly Ser Leu Val Asp Phe Leu Lys Thr Pro Ser Gly Ile Lys Leu
                        325                 330                 335

Thr Ile Asn Lys Leu Leu Asp Met Ala Ala Gln Ile Ala Glu Gly Met
                            340                 345                 350

Ala Phe Ile Glu Glu Arg Asn Tyr Ile His Arg Asp Leu Arg Ala Ala
                        355                 360                 365

Asn Ile Leu Val Ser Asp Thr Leu Ser Cys Lys Ile Ala Asp Phe Gly
        370                 375                 380

Leu Ala Arg Leu Ile Glu Asp Asn Glu Tyr Thr Ala Arg Glu Gly Ala
        385                 390                 395                 400

Lys Phe Pro Ile Lys Trp Thr Ala Pro Glu Ala Ile Asn Tyr Gly Thr
                            405                 410                 415

Phe Thr Ile Lys Ser Asp Val Trp Ser Phe Gly Ile Leu Leu Thr Glu
                        420                 425                 430

Ile Val Thr His Gly Arg Ile Pro Tyr Pro Gly Met Thr Asn Pro Glu
                        435                 440                 445

Val Ile Gln Asn Leu Glu Arg Gly Tyr Arg Met Val Arg Pro Asp Asn
        450                 455                 460

Cys Pro Glu Glu Leu Tyr Gln Leu Met Arg Leu Cys Trp Lys Glu Arg
        465                 470                 475                 480

Pro Glu Asp Arg Pro Thr Phe Asp Tyr Leu Arg Ser Val Leu Glu Asp
                            485                 490                 495

Phe Phe Thr Ala Thr Glu Gly Gln Tyr Gln Pro Gln Pro
                        500                 505

<210> SEQ ID NO 10
<211> LENGTH: 509
<212> TYPE: PRT
<213> ORGANISM: Artificial Sequence
<220> FEATURE:
<223> OTHER INFORMATION: Amino acid sequence of mutated human Lck 2
      (Y318L)

<400> SEQUENCE: 10

Met Gly Cys Gly Cys Ser Ser His Pro Glu Asp Asp Trp Met Glu Asn
        1               5                   10                  15

Ile Asp Val Cys Glu Asn Cys His Tyr Pro Ile Val Pro Leu Asp Gly
                        20                  25                  30

Lys Gly Thr Leu Leu Ile Arg Asn Gly Ser Glu Val Arg Asp Pro Leu
                    35                  40                  45

Val Thr Tyr Glu Gly Ser Asn Pro Pro Ala Ser Pro Leu Gln Asp Asn
                50                  55                  60

Leu Val Ile Ala Leu His Ser Tyr Glu Pro Ser His Asp Gly Asp Leu
        65                  70                  75                  80

Gly Phe Glu Lys Gly Glu Gln Leu Arg Ile Leu Glu Gln Ser Gly Glu
                        85                  90                  95

Trp Trp Lys Ala Gln Ser Leu Thr Thr Gly Gln Glu Gly Phe Ile Pro
                    100                 105                 110

Phe Asn Phe Val Ala Lys Ala Asn Ser Leu Glu Pro Glu Pro Trp Phe
                115                 120                 125

Phe Lys Asn Leu Ser Arg Lys Asp Ala Glu Arg Gln Leu Leu Ala Pro
            130                 135                 140

Gly Asn Thr His Gly Ser Phe Leu Ile Arg Glu Ser Glu Ser Thr Ala
        145                 150                 155                 160
```

-continued

```
Gly Ser Phe Ser Leu Ser Val Arg Asp Phe Asp Gln Asn Gln Gly Glu
            165                 170                 175

Val Val Lys His Tyr Lys Ile Arg Asn Leu Asp Asn Gly Gly Phe Tyr
        180                 185                 190

Ile Ser Pro Arg Ile Thr Phe Pro Gly Leu His Glu Leu Val Arg His
        195                 200                 205

Tyr Thr Asn Ala Ser Asp Gly Leu Cys Thr Arg Leu Ser Arg Pro Cys
    210                 215                 220

Gln Thr Gln Lys Pro Gln Lys Pro Trp Trp Glu Asp Glu Trp Glu Val
225                 230                 235                 240

Pro Arg Glu Thr Leu Lys Leu Val Glu Arg Leu Gly Ala Gly Gln Phe
                245                 250                 255

Gly Glu Val Trp Met Gly Tyr Tyr Asn Gly His Thr Lys Val Ala Val
            260                 265                 270

Lys Ser Leu Lys Gln Gly Ser Met Ser Pro Asp Ala Phe Leu Ala Glu
        275                 280                 285

Ala Asn Leu Met Lys Gln Leu Gln His Gln Arg Leu Val Arg Leu Tyr
    290                 295                 300

Ala Val Val Thr Gln Glu Pro Ile Tyr Ile Ile Thr Glu Leu Met Glu
305                 310                 315                 320

Asn Gly Ser Leu Val Asp Phe Leu Lys Thr Pro Ser Gly Ile Lys Leu
                325                 330                 335

Thr Ile Asn Lys Leu Leu Asp Met Ala Ala Gln Ile Ala Glu Gly Met
            340                 345                 350

Ala Phe Ile Glu Glu Arg Asn Tyr Ile His Arg Asp Leu Arg Ala Ala
        355                 360                 365

Asn Ile Leu Val Ser Asp Thr Leu Ser Cys Lys Ile Ala Asp Phe Gly
    370                 375                 380

Leu Ala Arg Leu Ile Glu Asp Asn Glu Tyr Thr Ala Arg Glu Gly Ala
385                 390                 395                 400

Lys Phe Pro Ile Lys Trp Thr Ala Pro Glu Ala Ile Asn Tyr Gly Thr
                405                 410                 415

Phe Thr Ile Lys Ser Asp Val Trp Ser Phe Gly Ile Leu Leu Thr Glu
            420                 425                 430

Ile Val Thr His Gly Arg Ile Pro Tyr Pro Gly Met Thr Asn Pro Glu
        435                 440                 445

Val Ile Gln Asn Leu Glu Arg Gly Tyr Arg Met Val Arg Pro Asp Asn
    450                 455                 460

Cys Pro Glu Glu Leu Tyr Gln Leu Met Arg Leu Cys Trp Lys Glu Arg
465                 470                 475                 480

Pro Glu Asp Arg Pro Thr Phe Asp Tyr Leu Arg Ser Val Leu Glu Asp
                485                 490                 495

Phe Phe Thr Ala Thr Glu Gly Gln Tyr Gln Pro Gln Pro
            500                 505

<210> SEQ ID NO 11
<211> LENGTH: 509
<212> TYPE: PRT
<213> ORGANISM: Artificial Sequence
<220> FEATURE:
<223> OTHER INFORMATION: Amino acid sequence of mutated human Lck 1
      (S323C)

<400> SEQUENCE: 11

Met Gly Cys Gly Cys Ser Ser His Pro Glu Asp Asp Trp Met Glu Asn
1               5                   10                  15
```

```
Ile Asp Val Cys Glu Asn Cys His Tyr Pro Ile Val Pro Leu Asp Gly
             20                  25                  30

Lys Gly Thr Leu Leu Ile Arg Asn Gly Ser Glu Val Arg Asp Pro Leu
         35                  40                  45

Val Thr Tyr Glu Gly Ser Asn Pro Ala Ser Pro Leu Gln Asp Asn
     50                  55                  60

Leu Val Ile Ala Leu His Ser Tyr Glu Pro Ser His Asp Gly Asp Leu
 65                  70                  75                  80

Gly Phe Glu Lys Gly Glu Gln Leu Arg Ile Leu Glu Gln Ser Gly Glu
                 85                  90                  95

Trp Trp Lys Ala Gln Ser Leu Thr Thr Gly Gln Glu Gly Phe Ile Pro
             100                 105                 110

Phe Asn Phe Val Ala Lys Ala Asn Ser Leu Glu Pro Glu Pro Trp Phe
         115                 120                 125

Phe Lys Asn Leu Ser Arg Lys Asp Ala Glu Arg Gln Leu Leu Ala Pro
130                 135                 140

Gly Asn Thr His Gly Ser Phe Leu Ile Arg Glu Ser Glu Ser Thr Ala
145                 150                 155                 160

Gly Ser Phe Ser Leu Ser Val Arg Asp Phe Asp Gln Asn Gln Gly Glu
                 165                 170                 175

Val Val Lys His Tyr Lys Ile Arg Asn Leu Asp Asn Gly Gly Phe Tyr
             180                 185                 190

Ile Ser Pro Arg Ile Thr Phe Pro Gly Leu His Glu Leu Val Arg His
         195                 200                 205

Tyr Thr Asn Ala Ser Asp Gly Leu Cys Thr Arg Leu Ser Arg Pro Cys
210                 215                 220

Gln Thr Gln Lys Pro Gln Lys Pro Trp Trp Glu Asp Glu Trp Glu Val
225                 230                 235                 240

Pro Arg Glu Thr Leu Lys Leu Val Glu Arg Leu Gly Ala Gly Gln Phe
                 245                 250                 255

Gly Glu Val Trp Met Gly Tyr Tyr Asn Gly His Thr Lys Val Ala Val
             260                 265                 270

Lys Ser Leu Lys Gln Gly Ser Met Ser Pro Asp Ala Phe Leu Ala Glu
         275                 280                 285

Ala Asn Leu Met Lys Gln Leu Gln His Gln Arg Leu Val Arg Leu Tyr
290                 295                 300

Ala Val Val Thr Gln Glu Pro Ile Tyr Ile Ile Thr Glu Tyr Met Glu
305                 310                 315                 320

Asn Gly Cys Leu Val Asp Phe Leu Lys Thr Pro Ser Gly Ile Lys Leu
                 325                 330                 335

Thr Ile Asn Lys Leu Leu Asp Met Ala Ala Gln Ile Ala Glu Gly Met
             340                 345                 350

Ala Phe Ile Glu Glu Arg Asn Tyr Ile His Arg Asp Leu Arg Ala Ala
         355                 360                 365

Asn Ile Leu Val Ser Asp Thr Leu Ser Cys Lys Ile Ala Asp Phe Gly
370                 375                 380

Leu Ala Arg Leu Ile Glu Asp Asn Glu Tyr Thr Ala Arg Glu Gly Ala
385                 390                 395                 400

Lys Phe Pro Ile Lys Trp Thr Ala Pro Glu Ala Ile Asn Tyr Gly Thr
                 405                 410                 415

Phe Thr Ile Lys Ser Asp Val Trp Ser Phe Gly Ile Leu Leu Thr Glu
             420                 425                 430
```

```
Ile Val Thr His Gly Arg Ile Pro Tyr Pro Gly Met Thr Asn Pro Glu
        435                 440                 445

Val Ile Gln Asn Leu Glu Arg Gly Tyr Arg Met Val Arg Pro Asp Asn
    450                 455                 460

Cys Pro Glu Glu Leu Tyr Gln Leu Met Arg Leu Cys Trp Lys Glu Arg
465                 470                 475                 480

Pro Glu Asp Arg Pro Thr Phe Asp Tyr Leu Arg Ser Val Leu Glu Asp
                485                 490                 495

Phe Phe Thr Ala Thr Glu Gly Gln Tyr Gln Pro Gln Pro
                500                 505

<210> SEQ ID NO 12
<211> LENGTH: 26
<212> TYPE: PRT
<213> ORGANISM: Artificial Sequence
<220> FEATURE:
<223> OTHER INFORMATION: Amino acid sequence part of mutated Zap-70
      (consensus)
<220> FEATURE:
<221> NAME/KEY: MISC_FEATURE
<222> LOCATION: (1)..(1)
<223> OTHER INFORMATION: Xaa1 is selected from Val and Ile
<220> FEATURE:
<221> NAME/KEY: MISC_FEATURE
<222> LOCATION: (2)..(2)
<223> OTHER INFORMATION: Xaa2 is selected from Arg, Lys and His
<220> FEATURE:
<221> NAME/KEY: MISC_FEATURE
<222> LOCATION: (3)..(3)
<223> OTHER INFORMATION: Xaa3 is selected from Leu, Ile, Val, Met, Ala,
      Phe and Tyr
<220> FEATURE:
<221> NAME/KEY: MISC_FEATURE
<222> LOCATION: (4)..(4)
<223> OTHER INFORMATION: Xaa4 is selected from Ile, Leu, Val, Met, Ala,
      Phe and Tyr
<220> FEATURE:
<221> NAME/KEY: MISC_FEATURE
<222> LOCATION: (5)..(5)
<223> OTHER INFORMATION: Xaa5 is selected from Gly, Pro and Ala
<220> FEATURE:
<221> NAME/KEY: MISC_FEATURE
<222> LOCATION: (6)..(6)
<223> OTHER INFORMATION: Xaa6 is selected from Val, Ile, Met, Leu, Phe,
      Ala and Pro
<220> FEATURE:
<221> NAME/KEY: MISC_FEATURE
<222> LOCATION: (7)..(7)
<223> OTHER INFORMATION: Xaa7 is selected from Cys, Ser, Thr and Ala
<220> FEATURE:
<221> NAME/KEY: MISC_FEATURE
<222> LOCATION: (8)..(8)
<223> OTHER INFORMATION: Xaa8 is selected from Gln and Asn
<220> FEATURE:
<221> NAME/KEY: MISC_FEATURE
<222> LOCATION: (9)..(9)
<223> OTHER INFORMATION: Xaa9 is selected from Ala, Val, Leu, Ile and
      Pro
<220> FEATURE:
<221> NAME/KEY: MISC_FEATURE
<222> LOCATION: (10)..(10)
<223> OTHER INFORMATION: Xaa10 is selected from Glu and Asp
<220> FEATURE:
<221> NAME/KEY: MISC_FEATURE
<222> LOCATION: (11)..(11)
<223> OTHER INFORMATION: Xaa11 is selected from Ala, Val, Leu, Ile and
      Pro
<220> FEATURE:
<221> NAME/KEY: MISC_FEATURE
<222> LOCATION: (12)..(12)
<223> OTHER INFORMATION: Xaa12 is selected from Leu, Ile, Val, Met, Ala,
      Phe and Tyr
<220> FEATURE:
<221> NAME/KEY: MISC_FEATURE
```

```
-continued

<222> LOCATION: (13)..(13)
<223> OTHER INFORMATION: Xaa13 is selected from Met, Val, Leu, Ile and
      Phe
<220> FEATURE:
<221> NAME/KEY: MISC_FEATURE
<222> LOCATION: (14)..(14)
<223> OTHER INFORMATION: Xaa14 is selected from Leu, Ile, Val, Met, Ala,
      Phe and Tyr
<220> FEATURE:
<221> NAME/KEY: MISC_FEATURE
<222> LOCATION: (15)..(15)
<223> OTHER INFORMATION: Xaa15 is selected from Val, Ile, Met, Leu, Phe,
      Ala and Pro
<220> FEATURE:
<221> NAME/KEY: MISC_FEATURE
<222> LOCATION: (16)..(16)
<223> OTHER INFORMATION: Xaa16 is selected from Met, Ala, Val, and Thr
<220> FEATURE:
<221> NAME/KEY: MISC_FEATURE
<222> LOCATION: (17)..(17)
<223> OTHER INFORMATION: Xaa17 is selected from Glu and Asp
<220> FEATURE:
<221> NAME/KEY: MISC_FEATURE
<222> LOCATION: (18)..(18)
<223> OTHER INFORMATION: Xaa18 is selected from Met, Tyr and Leu
<220> FEATURE:
<221> NAME/KEY: MISC_FEATURE
<222> LOCATION: (19)..(19)
<223> OTHER INFORMATION: Xaa19 is selected from Ala, Val, Leu, Ile and
      Pro
<220> FEATURE:
<221> NAME/KEY: MISC_FEATURE
<222> LOCATION: (20)..(20)
<223> OTHER INFORMATION: Xaa20 is selected from Gly, Pro and Ala
<220> FEATURE:
<221> NAME/KEY: MISC_FEATURE
<222> LOCATION: (21)..(21)
<223> OTHER INFORMATION: Xaa21 is selected from Gly, Pro and Ala
<220> FEATURE:
<221> NAME/KEY: MISC_FEATURE
<222> LOCATION: (22)..(22)
<223> OTHER INFORMATION: Xaa22 is selected from Gly, Pro and Ala
<220> FEATURE:
<221> NAME/KEY: MISC_FEATURE
<222> LOCATION: (23)..(23)
<223> OTHER INFORMATION: Xaa23 is selected from Pro, Ala and Gly
<220> FEATURE:
<221> NAME/KEY: MISC_FEATURE
<222> LOCATION: (24)..(24)
<223> OTHER INFORMATION: Xaa24 is selected from Leu, Ile, Val, Met, Ala,
      Phe and Tyr
<220> FEATURE:
<221> NAME/KEY: MISC_FEATURE
<222> LOCATION: (25)..(25)
<223> OTHER INFORMATION: Xaa25 is selected from His, Lys and Arg
<220> FEATURE:
<221> NAME/KEY: MISC_FEATURE
<222> LOCATION: (26)..(26)
<223> OTHER INFORMATION: Xaa26 is selected from Lys, Arg and His

<400> SEQUENCE: 12

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa
            20                  25

<210> SEQ ID NO 13
<211> LENGTH: 9
<212> TYPE: PRT
<213> ORGANISM: Artificial Sequence
<220> FEATURE:
<223> OTHER INFORMATION: Amino acid sequence part of mutated Lck
      (consensus)
<220> FEATURE:
<221> NAME/KEY: MISC_FEATURE
<222> LOCATION: (1)..(1)
```

```
<223> OTHER INFORMATION: Xab1 is selected from Thr, Val and Ser
<220> FEATURE:
<221> NAME/KEY: MISC_FEATURE
<222> LOCATION: (2)..(2)
<223> OTHER INFORMATION: Xab2 is selected from Glu and Asp
<220> FEATURE:
<221> NAME/KEY: MISC_FEATURE
<222> LOCATION: (3)..(3)
<223> OTHER INFORMATION: Xab3 is selected from Tyr and Leu
<220> FEATURE:
<221> NAME/KEY: MISC_FEATURE
<222> LOCATION: (4)..(4)
<223> OTHER INFORMATION: Xab4 is selected from Met, Val, Leu, Ile and
      Phe
<220> FEATURE:
<221> NAME/KEY: MISC_FEATURE
<222> LOCATION: (5)..(5)
<223> OTHER INFORMATION: Xab5 is selected from Glu and Asp
<220> FEATURE:
<221> NAME/KEY: MISC_FEATURE
<222> LOCATION: (6)..(6)
<223> OTHER INFORMATION: Xab6 is selected from Asn and Gln
<220> FEATURE:
<221> NAME/KEY: MISC_FEATURE
<222> LOCATION: (7)..(7)
<223> OTHER INFORMATION: Xab7 is selected from Gly, Pro and Ala
<220> FEATURE:
<221> NAME/KEY: MISC_FEATURE
<222> LOCATION: (8)..(8)
<223> OTHER INFORMATION: Xab8 is selected from Ser, Cys, Thr and Ala
<220> FEATURE:
<221> NAME/KEY: MISC_FEATURE
<222> LOCATION: (9)..(9)
<223> OTHER INFORMATION: Xab9 is selected from Leu, Ile, Val, Met, Ala,
      Phe and Tyr

<400> SEQUENCE: 13

Xaa Xaa Xaa Xaa Xaa Xaa Xaa Xaa Xaa
1               5

<210> SEQ ID NO 14
<211> LENGTH: 1857
<212> TYPE: DNA
<213> ORGANISM: Artificial Sequence
<220> FEATURE:
<223> OTHER INFORMATION: Nucleic acid sequence of Z1 (5'- 3'; mutated
      human Zap-70)

<400> SEQUENCE: 14
atgcctgatc ctgccgccca tctgccattc ttctacggca gcatcagcag agccgaggcc      60
gaggaacacc tgaagctggc cggaatggcc gacggcctgt tcctgctgag acagtgcctg     120
agaagcctgg gcggctacgt gctgagcctg gtgcacgatg tgcggttcca ccacttcccc     180
atcgagcggc agctgaacgg cacctacgct atcgctggcg gcaaggccca ttgtggacct     240
gccgagctgt gcgagttcta cagcagagat cccgatggcc tgccctgcaa cctgcggaag     300
ccctgcaata gacccagcgg cctggaacct cagcccggcg tgttcgactg tctgagggat     360
gccatggtgc gcgactacgt gcggcagacc tggaagctgg aaggcgaggc tctggaacag     420
gctatcatca gccaggcccc ccaggtggaa aagctgatcg ccacaaccgc ccacgagcgg     480
atgccctggt atcacagcag cctgaccaga gaggaagccg agcggaagct gtactctggc     540
gcccagaccg acggcaaatt cctgctgcgg cccagaaaag agcagggcac atacgccctg     600
agcctgatct acggcaagac cgtgtaccac acctgatct cccaggacaa ggccggcaag     660
tactgcatcc ccgagggcac caagttcgac accctgtggc agctggtgga atatctgaag     720
ctgaaggccg acggactgat ctactgcctg aaagaggcct gccccaacag cagcgccagc     780
aatgctagcg gagccgccgc tcctacactg cctgccatc ctagcaccct gacccacccc     840
```

```
cagagaagaa tcgataccct gaattccgac ggctacaccc ccgagcctgc cagaatcacc    900
agccccgaca agcccagacc catgcccatg acaccagctg tgtacgagag cccctacagc    960
gaccccgagg aactgaagga caagaagctg ttcctgaagc gggacaacct gctgattgcc   1020
gacatcgagc tgggctgcgg caactttgga tctgtgcggc agggcgtgta ccggatgcgg   1080
aagaaacaga tcgacgtggc catcaaggtg ctgaagcagg aaccgagaa ggccgatacc    1140 gaggaaatga tgcgcgaggc ccagatcatg caccagctgg acaacccta catcgtgcgg   1200 ctgatcggcg tgtgtcaggc cgaagctctg atgctcgtgg ccgaaatggc tggcggcgga   1260
cccctgcaca agtttctcgt gggcaagcgg aagagatcc ccgtgtccaa tgtggccgag    1320
ctgctgcacc aggtgtcaat gggaatgaag tacctcgagg agaagaactt cgtgcaccgg   1380
gacctggccg ccagaaacgt gctgctcgtg aaccggcact acgccaagat cagcgacttt   1440
ggcctgagca aggccctggg cgccgacgac agctactaca cagccagatc cgccggaaag   1500
tggcccctga gtggtacgc cccgagtgc atcaacttca gaaagttcag cagccgcagc    1560
gacgtgtggt cctacggcgt gacaatgtgg gaggccctga gctacggcca gaaccctac    1620 aagaagatga agggccccga agtgatggcc ttcatcgagc agggaaagcg gatgaatgc    1680 cccctgagt gccctcctga gctgtatgcc ctgatgagcg actgctggat ctacaagtgg   1740
gaggaccggc ccgacttcct gaccgtggaa cagagaatgc gggcctgcta ctacagcctg   1800
gcctctaagg tggaaggccc tcctggcagc acccagaaag ccgaagccgc ctgtgct    1857

<210> SEQ ID NO 15
<211> LENGTH: 1857
<212> TYPE: DNA
<213> ORGANISM: Artificial Sequence
<220> FEATURE:
<223> OTHER INFORMATION: Nucleic acid sequence of Z2 (5'- 3'; mutated
      human Zap-70)

<400> SEQUENCE: 15
atgcctgatc ctgccgccca tctgccattc ttctacggca gcatcagcag agccgaggcc     60
gaggaacacc tgaagctggc cggaatggcc gacggcctgt cctgctgag acagtgcctg    120 agaagcctgg gcggctacgt gctgagcctg gtgcacgatg tgcggttcca ccacttcccc    180
atcgagcggc agctgaacgg cacctacgct atcgctggcg gcaaggccca ttgtggacct    240
gccgagctgt gcgagttcta cagcagagat cccgatggcc tgccctgcaa cctgcggaag    300
ccctgcaata gacccagcgg cctggaacct cagcccggcg tgttcgactg tctgagggat    360
gccatggtgc gcgactacgt gcggcagacc tggaagctgg aaggcgaggc tctggaacag    420
gctatcatca gccaggcccc ccaggtggaa aagctgatcg ccacaaccgc ccacgagcgg    480
atgccctggt atcacagcag cctgaccaga gaggaagccg agcggaagct gtactctggc    540
gcccagaccg acggcaaatt cctgctgcgg cccagaaaag agcagggcac atacgccctg    600
agcctgatct acgcaagac cgtgtaccac tacctgatct cccaggacaa ggccggcaag    660
tactgcatcc ccgagggcac caagttcgac accctgtggc agctggtgga atatctgaag    720
ctgaaggccg acggactgat ctactgcctg aaagaggcct gccccaacag cagcgccagc    780
aatgctagcg agccgccgc tcctacactg cctgcccatc ctagcaccct gacccaccc    840 cagagaagaa tcgataccct gaattccgac ggctacaccc ccgagcctgc cagaatcacc    900
agccccgaca agcccagacc catgcccatg acaccagctg tgtacgagag cccctacagc    960
gaccccgagg aactgaagga caagaagctg ttcctgaagc gggacaacct gctgattgcc   1020
```

-continued

```
gacatcgagc tgggctgcgg caactttgga tctgtgcggc agggcgtgta ccggatgcgg   1080
aagaaacaga tcgacgtggc catcaaggtg ctgaagcagg aaccgagaa ggccgatacc    1140 gaggaaatga tgcgcgaggc ccagatcatg caccagctgg acaacccta catcgtgcgg    1200 ctgatcggcg tgtgtcaggc cgaagctctg atgctcgtga ccgaaatggc tggcggcgga   1260
cccctgcaca agtttctcgt gggcaagcgg aagagatcc ccgtgtccaa tgtggccgag    1320
ctgctgcacc aggtgtcaat gggaatgaag tacctcgagg agaagaactt cgtgcaccgg   1380
gacctggccg ccagaaacgt gctgctcgtg aaccggcact acgccaagat cagcgacttt   1440
ggcctgagca aggccctggg cgccgacgac agctactaca cagccagatc cgccggaaag   1500 tggccctga agtggtacgc ccccgagtgc atcaacttca gaaagttcag cagccgcagc    1560
gacgtgtggt cctacggcgt gacaatgtgg gaggccctga gctacggcca gaaaccctac    1620
aagaagatga agggccccga agtgatggcc ttcatcgagc agggaaagcg gatggaatgc    1680
ccccctgagt gccctcctga gctgtatgcc ctgatgagcg actgctggat ctacaagtgg    1740
gaggaccggc ccgacttcct gaccgtggaa cagagaatgc gggcctgcta ctacagcctg    1800
gcctctaagg tggaaggccc tcctggcagc acccagaaag ccgaagccgc ctgtgct       1857
```

<210> SEQ ID NO 16
<211> LENGTH: 1857
<212> TYPE: DNA
<213> ORGANISM: Artificial Sequence
<220> FEATURE:
<223> OTHER INFORMATION: Nucleic acid sequence of Z3 (5'- 3'; mutated human Zap-70)

<400> SEQUENCE: 16

```
atgcctgatc ctgccgccca tctgccattc ttctacggca gcatcagcag agccgaggcc    60
gaggaacacc tgaagctggc cggaatggcc gacggcctgt cctgctgag acagtgcctg    120 agaagcctgg cggctacgt gctgagcctg gtgcacgatg tgcggttcca ccacttcccc    180
atcgagcggc agctgaacgg cacctacgct atcgctggcg gcaaggccca ttgtggacct    240
gccgagctgt gcgagttcta cagcagagat cccgatggcc tgccctgcaa cctgcggaag    300
ccctgcaata gacccagcgg cctggaacct cagccggcg tgttcgactg tctgagggat    360
gccatggtgc gcgactacgt gcggcagacc tggaagctgg aaggcgaggc tctggaacag    420
gctatcatca gccaggcccc ccaggtggaa aagctgatcg ccacaaccgc ccacgagcgg    480 atgcctggt atcacagcag cctgaccaga gaggaagccg agcggaagct gtactctggc    540
gcccagaccg acggcaaatt cctgctgcgg cccagaaaag agcagggcac atacgccctg    600
agcctgatct acggcaagac cgtgtaccac tacctgatct cccaggacaa ggccggcaag    660
tactgcatcc ccgagggcac caagttcgac accctgtggc agctggtgga atatctgaag    720
ctgaaggccg acggactgat ctactgcctg aaagaggcct gcccaacag cagcgccagc    780 aatgctagcg agccgccgc tcctacactg cctgcccatc ctagcaccct gacccacccc    840
cagagaagaa tcgataccct gaattccgac ggctacaccc ccgagcctgc agaatcacc     900 agccccgaca gcccagacc catgcccatg gacaccagc tgtacgagag ccctacagc      960 gaccccgagg aactgaagga caagaagctg ttcctgaagc gggacaacct gctgattgcc   1020
gacatcgagc tgggctgcgg caactttgga tctgtgcggc agggcgtgta ccggatgcgg   1080
aagaaacaga tcgacgtggc catcaaggtg ctgaagcagg aaccgagaa ggccgatacc    1140 gaggaaatga tgcgcgaggc ccagatcatg caccagctgg acaacccta catcgtgcgg    1200
```

```
ctgatcggcg tgtgtcaggc cgaagctctg atgctcgtgg tcgaaatggc tggcggcgga    1260
cccctgcaca agtttctcgt gggcaagcgg aagagatcc ccgtgtccaa gtggccgag     1320 ctgctgcacc aggtgtcaat gggaatgaag tacctcgagg agaagaactt cgtgcaccgg    1380
gacctggccg ccagaaacgt gctgctcgtg aaccggcact acgccaagat cagcgacttt    1440
ggcctgagca aggccctggg cgccgacgac agctactaca cagccagatc cgccggaaag    1500
tggcccctga gtggtacgc ccccgagtgc atcaacttca aaagttcag cagccgcagc     1560 gacgtgtggt cctacggcgt gacaatgtgg gaggccctga gctacggcca gaaaccctac    1620
aagaagatga agggccccga agtgatggcc ttcatcgagc agggaaagcg gatggaatgc    1680 cccctgagt gccctcctga gctgtatgcc ctgatgagcg actgctggat ctacaagtgg    1740
gaggaccggc ccgacttcct gaccgtggaa cagagaatgc gggcctgcta ctacagcctg    1800
gcctctaagg tggaaggccc tcctggcagc acccagaaag ccgaagccgc ctgtgct      1857
```

<210> SEQ ID NO 17
<211> LENGTH: 1857
<212> TYPE: DNA
<213> ORGANISM: Artificial Sequence
<220> FEATURE:
<223> OTHER INFORMATION: Nucleic acid sequence of Z8 (5'- 3'; mutated human Zap-70)

<400> SEQUENCE: 17

```
atgcctgatc ctgccgccca tctgccattc ttctacggca gcatcagcag agccgaggcc      60
gaggaacacc tgaagctggc cggaatggcc gacggcctgt cctgctgag acagtgcctg     120 agaagcctgg gcggctacgt gctgagcctg gtgcacgatg tgcggttcca ccacttcccc    180
atcgagcggg agctgaacgg cacctacgct atcgctggcg gcaaggccca ttgtggacct    240
gccgagctgt gcgagttcta cagcagagat cccgatggcc tgccctgcaa cctgcggaag    300
ccctgcaata gacccagcgg cctggaacct cagcccggcg tgttcgactg tctgagggat    360
gccatggtgc gcgactacgt gcggcagacc tggaagctgg aaggcgaggc tctggaacag    420 ctatcatca gccaggcccc ccaggtggaa aagctgatcg ccacaaccgc ccacgagcgg    480
atgccctggt atcacagcag cctgaccaga gaggaagccg agcggaagct gtactctggc    540
gcccagaccg acggcaaatt cctgctgcgg cccagaaaag agcagggcac atacgccctg    600
agcctgatct acggcaagac cgtgtaccac tacctgatct cccaggacaa ggccggcaag    660
tactgcatcc ccgagggcac caagttcgac accctgtggc agctggtgga atatctgaag    720
ctgaaggccg acggactgat ctactgcctg aaagaggcct gccccaacag cagcgccagc    780
aatgctagcg gagccgccgc tcctacactg cctgcccatc ctagcaccct gacccacccc    840
cagagaagaa tcgatacccc tgaattccga cggctacaccc ccgagcctgc cagaatcacc    900
agccccgaca gcccagacc catgcccatg acaccagcg tgtacgagag cccctacagc    960 gacccccgagg aactgaagga caagaagctg ttcctgaagc gggacaacct gctgattgcc    1020
gacatcgagc tgggctgcgg caactttgga tctgtgcggc agggcgtgta ccggatgcgg    1080
aagaaacaga tcgacgtggc catcaaggtg ctgaagcagg aaccgagaa ggccgatacc    1140 gaggaaatga tgcgcgaggc ccagatcatg caccagctgg acaaccccta catcgtgcgg    1200
ctgatcggcg tgtgtcaggc cgaagctctg atgctcgtgg tcgaatacgc tggcggcga    1260 cccctgcaca gtttctcgt gggcaagcgg aagagatcc ccgtgtccaa gtggccgag     1320 ctgctgcacc aggtgtcaat gggaatgaag tacctcgagg agaagaactt cgtgcaccgg    1380
```

```
gacctggccg ccagaaacgt gctgctcgtg aaccggcact acgccaagat cagcgacttt      1440
ggcctgagca aggccctggg cgccgacgac agctactaca cagccagatc cgccggaaag      1500
tggcccctga gtggtacgc ccccgagtgc atcaacttca gaaagttcag cagccgcagc       1560
gacgtgtggt cctacggcgt gacaatgtgg gaggccctga gctacggcca gaaaccctac      1620
aagaagatga agggccccga agtgatggcc ttcatcgagc agggaaagcg gatggaatgc      1680
ccccctgagt gccctcctga gctgtatgcc ctgatgagcg actgctggat ctacaagtgg      1740
gaggaccggc ccgacttcct gaccgtggaa cagagaatgc gggcctgcta ctacagcctg      1800
gcctctaagg tggaaggccc tcctggcagc acccagaaag ccgaagccgc ctgtgct         1857
```

<210> SEQ ID NO 18
<211> LENGTH: 1857
<212> TYPE: DNA
<213> ORGANISM: Artificial Sequence
<220> FEATURE:
<223> OTHER INFORMATION: Nucleic acid sequence of Z9 (5'- 3'; mutated
     human Zap-70)

<400> SEQUENCE: 18

```
atgcctgatc ctgccgccca tctgccattc ttctacggca gcatcagcag agccgaggcc      60
gaggaacacc tgaagctggc cggaatggcc gacggcctgt cctgctgag acagtgcctg       120 agaagcctgg gcggctacgt gctgagcctg gtgcacgatg gcggttccta ccacttcccc      180
atcgagcggc agctgaacgg cacctacgct atcgctggcg gcaaggccca ttgtggacct      240
gccgagctgt gcgagttcta cagcagagat cccgatggcc tgccctgcaa cctgcggaag      300
ccctgcaata gacccagcgg cctggaacct cagcccggcg tgttcgactg tctgagggat      360
gccatggtgc gcgactacgt gcggcagacc tggaagctgg aaggcgaggc tctggaacag      420
gctatcatca gccaggcccc ccaggtggaa aagctgatcg ccacaaccgc ccacgagcgg      480
atgccctggt atcacagcag cctgaccaga gaggaagccg agcggaagct gtactctggc      540
gcccagaccg acggcaaatt cctgctgcgg cccagaaaag agcagggcac atacgccctg      600
agcctgatct acggcaagac cgtgtaccac taccctgatct cccaggacaa ggccggcaag      660
tactgcatcc ccgagggcac caagttcgac accctgtggc agctggtgga atatctgaag      720
ctgaaggccg acggactgat ctactgcctg aaagaggcct gccccaacag cagcgccagc      780
aatgctagcg gagccgccgc tcctacactg cctgcccatc ctagcaccct gacccacccc      840
cagagaagaa tcgatacccc tgaattccga ggctacaccc ccgagcctgc cagaatcacc      900
agccccgaca gcccagacc catgcccatg gacaccagcg tgtacgagag ccctacagc       960 gaccccgagg aactgaagga caagaagctg ttcctgaagc gggacaacct gctgattgcc      1020
gacatcgagc tgggctgcgg caactttgga tctgtgcggc agggcgtgta ccggatgcgg      1080
aagaaacaga tcgacgtggc catcaaggtg ctgaagcagg aaccgagaa ggccgatacc       1140 gaggaaatga tgcgcgaggc ccagatcatg caccagctga caaccccta catcattcgg      1200 ctgatcggcg tgtgtcaggc cgaagctctg atgctcgtgg tcgaaatggc tggcggcgga      1260
cccctgcaca gtttctcgt gggcaagcgg aagagatcc ccgtgtccaa gtggccgag       1320 ctgctgcacc aggtgtcaat gggaatgaag tacctcgagg agaagaactt cgtgcaccgg      1380
gacctggccg ccagaaacgt gctgctcgtg aaccggcact acgccaagat cagcgacttt      1440
ggcctgagca aggccctggg cgccgacgac agctactaca cagccagatc cgccggaaag      1500
tggcccctga gtggtacgc ccccgagtgc atcaacttca gaaagttcag cagccgcagc       1560
```

```
gacgtgtggt cctacggcgt gacaatgtgg gaggccctga gctacggcca gaaaccctac    1620
aagaagatga agggccccga agtgatggcc ttcatcgagc agggaaagcg gatggaatgc    1680 cccctgagt gccctcctga gctgtatgcc ctgatgagcg actgctggat ctacaagtgg    1740
gaggaccggc ccgacttcct gaccgtggaa cagagaatgc gggcctgcta ctacagcctg    1800
gcctctaagg tggaaggccc tcctggcagc acccagaaag ccgaagccgc ctgtgct       1857
```

<210> SEQ ID NO 19
<211> LENGTH: 1857
<212> TYPE: DNA
<213> ORGANISM: Artificial Sequence
<220> FEATURE:
<223> OTHER INFORMATION: Nucleic acid sequence of Z10 (5'- 3'; mutated human Zap-70)

<400> SEQUENCE: 19

```
atgcctgatc ctgccgccca tctgccattc ttctacggca gcatcagcag agccgaggcc    60
gaggaacacc tgaagctggc cggaatggcc gacggcctgt cctgctgag acagtgcctg     120 agaagcctgg cggctacgt gctgagcctg gtgcacgatg tgcggttcca ccacttcccc     180
atcgagcggc agctgaacgg cacctacgct atcgctggcg gcaaggccca ttgtggacct    240
gccgagctgt gcgagttcta cagcagagat cccgatggcc tgccctgcaa cctgcggaag    300
ccctgcaata gacccagcgg cctggaacct cagcccggct gttcgactg tctgagggat     360 gccatggtgc gcgactacgt gcggcagacc tggaagctgg aaggcgaggc tctggaacag    420
gctatcatca gccaggcccc ccaggtggaa aagctgatcg ccacaaccgc ccacgagcgg    480
atgccctggt atcacagcag cctgaccaga gaggaagccg agcggaagct gtactctggc    540
gcccagaccg acggcaaatt cctgctgcgg cccagaaaag agcagggcac atacgccctg    600
agcctgatct acggcaagac cgtgtaccac tacctgatct cccaggacaa ggccggcaag    660
tactgcatcc ccgagggcac caagttcgac accctgtggc agctggtgga atatctgaag    720
ctgaaggccg acggactgat ctactgcctg aaagaggcct gccccaacag cagcgccagc    780
aatgctagcg agccgccgc tcctacactg cctgccccatc ctagcaccct gacccacccc    840
cagagaagaa tcgataccct gaattccgac ggctacaccc ccgagcctgc cagaatcacc    900
agccccgaca gcccagacc catgcccatg gacaccagcg tgtacgagag cccctacagc    960
gaccccgagg aactgaagga caagaagctg ttcctgaagc gggacaacct gctgattgcc    1020
gacatcgagc tgggctgcgg caactttgga tctgtgcggc agggcgtgta ccggatgcgg    1080
aagaaacaga tcgacgtggc catcaaggtg ctgaagcagg aaccgagaa ggccgatacc    1140 gaggaaatga tgcgcgaggc ccagatcatg caccagctgg acaaccccta catcattcgg    1200
ctgatcggcg tgtgtcaggc cgaagctctg atgctcgtgg tcgaatacgc tggcggcgga    1260
cccctgcaca gtttctcgt gggcaagcgg aagagatcc ccgtgtccaa tgtggccgag     1320
ctgctgcacc aggtgtcaat gggaatgaag tacctcgagg agaagaactt cgtgcaccgg    1380
gacctggccg ccagaaacgt gctgctcgtg aaccggcact acgccaagat cagcgacttt    1440
ggcctgagca aggcccctggg cgccgacgac agctactaca cagccagatc cgccggaaag    1500
tggcccctga agtggtacgc cccgagtgc atcaacttca gaaagttcag cagccgcagc    1560
gacgtgtggt cctacggcgt gacaatgtgg gaggccctga gctacggcca gaaaccctac    1620
aagaagatga agggccccga agtgatggcc ttcatcgagc agggaaagcg gatggaatgc    1680 cccctgagt gccctcctga gctgtatgcc ctgatgagcg actgctggat ctacaagtgg    1740
```

```
gaggaccggc cgacttcct gaccgtggaa cagagaatgc gggcctgcta ctacagcctg   1800
gcctctaagg tggaaggccc tcctggcagc acccagaaag ccgaagccgc ctgtgct      1857

<210> SEQ ID NO 20
<211> LENGTH: 509
<212> TYPE: PRT
<213> ORGANISM: Artificial Sequence
<220> FEATURE:
<223> OTHER INFORMATION: Amino acid sequence of mutated human Lck 4
      (S323C + Y318L)

<400> SEQUENCE: 20

Met Gly Cys Gly Cys Ser Ser His Pro Glu Asp Asp Trp Met Glu Asn
1               5                   10                  15

Ile Asp Val Cys Glu Asn Cys His Tyr Pro Ile Val Pro Leu Asp Gly
            20                  25                  30

Lys Gly Thr Leu Leu Ile Arg Asn Gly Ser Glu Val Arg Asp Pro Leu
        35                  40                  45

Val Thr Tyr Glu Gly Ser Asn Pro Pro Ala Ser Pro Leu Gln Asp Asn
    50                  55                  60

Leu Val Ile Ala Leu His Ser Tyr Glu Pro Ser His Asp Gly Asp Leu
65                  70                  75                  80

Gly Phe Glu Lys Gly Glu Gln Leu Arg Ile Leu Glu Gln Ser Gly Glu
                85                  90                  95

Trp Trp Lys Ala Gln Ser Leu Thr Thr Gly Gln Glu Gly Phe Ile Pro
            100                 105                 110

Phe Asn Phe Val Ala Lys Ala Asn Ser Leu Glu Pro Glu Pro Trp Phe
        115                 120                 125

Phe Lys Asn Leu Ser Arg Lys Asp Ala Glu Arg Gln Leu Leu Ala Pro
    130                 135                 140

Gly Asn Thr His Gly Ser Phe Leu Ile Arg Glu Ser Glu Ser Thr Ala
145                 150                 155                 160

Gly Ser Phe Ser Leu Ser Val Arg Asp Phe Asp Gln Asn Gln Gly Glu
                165                 170                 175

Val Val Lys His Tyr Lys Ile Arg Asn Leu Asp Asn Gly Gly Phe Tyr
            180                 185                 190

Ile Ser Pro Arg Ile Thr Phe Pro Gly Leu His Glu Leu Val Arg His
        195                 200                 205

Tyr Thr Asn Ala Ser Asp Gly Leu Cys Thr Arg Leu Ser Arg Pro Cys
    210                 215                 220

Gln Thr Gln Lys Pro Gln Lys Pro Trp Trp Glu Asp Glu Trp Glu Val
225                 230                 235                 240

Pro Arg Glu Thr Leu Lys Leu Val Glu Arg Leu Gly Ala Gly Gln Phe
                245                 250                 255

Gly Glu Val Trp Met Gly Tyr Tyr Asn Gly His Thr Lys Val Ala Val
            260                 265                 270

Lys Ser Leu Lys Gln Gly Ser Met Ser Pro Asp Ala Phe Leu Ala Glu
        275                 280                 285

Ala Asn Leu Met Lys Gln Leu Gln His Gln Arg Leu Val Arg Leu Tyr
    290                 295                 300

Ala Val Val Thr Gln Glu Pro Ile Tyr Ile Ile Thr Glu Leu Met Glu
305                 310                 315                 320

Asn Gly Cys Leu Val Asp Phe Leu Lys Thr Pro Ser Gly Ile Lys Leu
                325                 330                 335
```

-continued

```
Thr Ile Asn Lys Leu Leu Asp Met Ala Ala Gln Ile Ala Glu Gly Met
            340                 345                 350

Ala Phe Ile Glu Glu Arg Asn Tyr Ile His Arg Asp Leu Arg Ala Ala
        355                 360                 365

Asn Ile Leu Val Ser Asp Thr Leu Ser Cys Lys Ile Ala Asp Phe Gly
        370                 375                 380

Leu Ala Arg Leu Ile Glu Asp Asn Glu Tyr Thr Ala Arg Glu Gly Ala
385                 390                 395                 400

Lys Phe Pro Ile Lys Trp Thr Ala Pro Glu Ala Ile Asn Tyr Gly Thr
                405                 410                 415

Phe Thr Ile Lys Ser Asp Val Trp Ser Phe Gly Ile Leu Leu Thr Glu
            420                 425                 430

Ile Val Thr His Gly Arg Ile Pro Tyr Pro Gly Met Thr Asn Pro Glu
        435                 440                 445

Val Ile Gln Asn Leu Glu Arg Gly Tyr Arg Met Val Arg Pro Asp Asn
        450                 455                 460

Cys Pro Glu Glu Leu Tyr Gln Leu Met Arg Leu Cys Trp Lys Glu Arg
465                 470                 475                 480

Pro Glu Asp Arg Pro Thr Phe Asp Tyr Leu Arg Ser Val Leu Glu Asp
                485                 490                 495

Phe Phe Thr Ala Thr Glu Gly Gln Tyr Gln Pro Gln Pro
            500                 505
```

KINASE MUTANTS AND USES THEREOF

FIELD OF THE INVENTION

The present invention relates to the field of gene therapy and in particular, to the use of genetically modified cells expressing specific kinase mutants for modulating the behavior of those cells with respect to their target, in particular to control the behavior of the cells either involved directly in a target disease or in the control or destruction of the disease-related cells.

BACKGROUND OF THE INVENTION

Protein kinases catalyze the phosphorylation of proteins that in turn modulate the activity of the protein, control its localization in cells, stabilize it or mark it for destruction, and orchestrate its interaction with other proteins. Kinases are thus the key regulators of biological pathways and cell function, particularly in signal transduction and coordination of complex functions such as the cell cycle.

More than 500 human protein kinases have been discovered. In particular, those human protein kinases include lymphocyte-specific protein tyrosine kinase (Lck) found in lymphocytes, notably in T cells and Zeta-chain-associated protein kinase 70 (ZAP-70) found in T cells and natural killer cells (NK cells). Upon the T-cell receptor (TCR) binding to a specific antigen presented by the Major Histocompatibility Complex (MHC), Lck phosphorylates the immunoreceptor tyrosine-based activation motifs (ITAMs) of the intracellular chains of the cluster of differentiation 3 (CD3) and ζ-chains of the TCR complex, allowing cytoplasmic kinase ZAP-70 to bind to them. Lck then phosphorylates and activates ZAP-70. Upon activation of the TCR and phosphorylation of the ITAMs of the TCR complex, ZAP-70 is recruited and phosphorylates the transmembrane protein Linker for activation of T cells (LAT). This initiates a biological cascade leading to the transcription of several gene products allowing T-cells differentiation, proliferation and secretion of cytokines. Therefore, Lck and ZAP-70 play a critical role in T-cell response, and their inhibition leads to T-cell inactivation (*Brownlie et al., 2013, Nature Reviews. Immunology,* 13(4): 257-269; *Wang et al., 2010, Cold Spring Harbor Perspectives in Biology,* 2(5): a002279; *Chakraborty et al., 2014, Nature Immunology,* 15(9), 798-807).

Further protein kinases involved in the control of T-cells function, in particular activation, include proto-oncogene tyrosine-protein kinase Fyn (FYN), tyrosine-protein kinase CSK (or C-terminal Src kinase; CSK), tyrosine-protein kinase ITK/TSK (or interleukin-2-inducible T-cell kinase; ITK) (*Brownlie et al., 2013, Nat Rev Immunol.,* 13, 257-269), tyrosine-protein kinase ABL (ABL) (*Gu et al., 2009, Immunol. Rev.,* 228(1), 170-183).

Due to the kinase importance as targets for the treatment of several pathologies, in particular in oncology, several tens of drugs which inhibit the activity of kinases have been developed or are under development. Studies have shown that, despite the functional and structural similarities between kinases, several kinase inhibitors have a narrow spectrum of specificity, meaning that most of the 500 human kinases will not be affected by them. (*Karaman et al., 2008, Nat. Biotechnol.,* 26, 127-132). In particular, several Food and Drug Administration (FDA) approved kinase inhibitors have no or little inhibitory effect on the wild type Zap-70 (e.g. afatinib, erlotinib and lapatinib) or Lck (e.g. afatinib, erlotinib and gefitinib) (*Karaman et al., supra*).

A method for the generation of target-specific protein kinase inhibitors was developed that utilizes a functionally silent active-site mutation to sensitize a target kinase to inhibition by adenosine triphosphate (ATP) analogs that do not inhibit wild-type kinase (WO 2005/000197). In this approach, a residue at a structurally conserved position in the kinase active site (gatekeeper) is mutated from natural bulky amino acid side chains to smaller residues and a novel pocket is created within the ATP-binding site, which is not found in wild-type kinase. Such an engineered kinase is said to be able to still accommodate ATP and functions normally, but additionally to have a high affinity for large ATP analogs, pyrazolo[3,4-d]pyrimidine (PP) inhibitors, that compete for entry into the ATP binding site. Electrophile-sensitive (ES)-kinases where the gatekeeper site is mutated to cysteine for sensitizing the ES-kinase to PP-inhibitors have been also developed (*Zhang et al., 2013, ACS Chem Biol.,* 8(9):1931-8). Mutated kinases were used to study the function of Zap-70 and a first mutant of ZAP-70 (AS1) was generated by mutating the gatekeeper methionine to alanine (M414A) and the second mutant of ZAP-70 (AS2), was generated by introducing, a secondary mutation, C405V, in conjunction with M414A (*Levin et al., 2008, J Biol Chem.,* 283(22): 15419-15430). A similar approach was used to study the function of Lck where mutated Lcks were generated: Lck-as with the mutation T316G and Lck$^a$-as with the double mutation T316G and Y505F mutation (*Denzel et al., 2003, J Immunol.,* 171(2):519-23). In this approach, a mutation is first introduced into the kinase and then a ligand is designed for inhibiting the mutated kinase. The so-designed ligand would then need to be subjected to extensive further characterization and tests for pharmacokinetics and pharmacodynamics in view of potential therapeutic use. Therefore, the attrition rate of those ligands based on undesirable ADME profile is rather high.

Immunotherapy is gaining increasing importance for the treatment and prevention of various human diseases including cancer. Adoptive cell therapy (ACT) uses T-cells engineered to xpress a cancer-related TCR for recognizing and targeting cancer cells (*Rosenberg et al., 2015, Science,* 348, 62-68; *Khalil et al., 2016, Nat. Rev. Clin. Oncol.,* 13, 273-290). It is known that this type of treatment can lead to rapid and dramatic side effects after reinjection of the modified T-cells into the patient, due, to for instance, to an auto-immune response that may include cerebral hemorrhage, epileptic seizures, cardiac arrest, multiple organ failure and irreversible neurologic damage (*van den Berg et al., 2015, Mol. Ther.,* 23, 1541-1550). Currently, side effects are counter-acted by administration of corticosteroids, which results in the shutdown of the whole immune system. Studies investigating the possibility to use suicide genes to eradicate irreversibly the transferred T cells have also been reported (*Sato et al., 2007, Mol. Ther.,* 15, 962-970; *Di Stasi et al., 2011, N. Engl. J. Med.,* 365 (18): 1673-1683). However, this technique is rather costly, it will end the effect of the treatment as well by eradicating irreversibly the engineered T-cells and may also itself have further side effects. The use of adoptive transfer of virus-specific T cells was also in the prevention and treatment of infections with viruses in patients after hematopoietic stem cell transplant (*Gerdemann et al., 2013, Mol Ther.* 21(11): 2113-21; *Papadopoulou et al., 2014, Sci Transl Med.* 6(242): 242ra83). Single T cell lines from stem cell donors, which have specificity for up to five viruses (cytomegalovirus, adenovirus, Epstein Barr virus, BK virus and human herpesvirus 6) have been generated (*Papadopoulou et al., 2014, supra*).

Stem-cell therapy is an emerging therapeutic route and a well-established and widely used stem cell treatment is the transplantation of blood stem cells to treat diseases and conditions of the blood and immune system, or to restore the blood system after treatments for specific cancers. Examples of used stem-cell therapy include bone marrow transplant and the therapies with the use of umbilical cord blood. Research is underway to develop further sources for stem cells, and to apply stem-cell treatments for neurodegenerative diseases and conditions such as diabetes, heart disease, and other conditions. However, this type of treatment can lead to various side effects such as toxicity, neoplasm formation and other unwanted biological effects (*Herberts et al.*, 2011, *J Transl Med.*, 9: 29).

Therefore, there is a need to find specific agents able to control the auto-immune response resulting from ACT using engineered T-cells, while preserving the immune system integrity of the patient.

SUMMARY OF THE INVENTION

The present invention is based on the finding that it is possible to modify kinases, such as ZAP-70 and/or Lck, for reprogramming them to render them sensitive to a specific inhibitor which had normally no or little binding affinity for the native kinase, in order to control, through the use of the specific inhibitor, the behavior of cells genetically engineered to express those mutated kinases, while keeping the activity of the wild-type kinases in the non-modified cells, unchanged. The invention is particularly directed to the design of new kinase mutants, such as mutants of ZAP-70 and/or Lck, which are rendered sensitive to a selected specific kinase inhibitor having little and no affinity for the wild-type, the expression of those mutants in cells such as T-cells, in particular T-cells expressing at least one cancer-related TCR and the use thereof in the treatment of cancers, for example by adoptive cell therapy. The present invention is particularly useful for controlling the activity of specific biological pathways in specific cells of a living organism, such as a human patient, through the inhibition of those engineered kinases expressed by these specific cells. This invention could be used in several treatments against various human diseases, notably cancer. A particular advantage of the present invention is that, contrarily to standard therapies, the strategy is not necessarily to target the cells at the origin of the disease, e.g. cancer cells, but to possibly modify the behavior of cells that could be involved in the control or destruction of the disease-related cells. Kinase reprograming could be used for modifying the behavior of those controlling cells, by stimulating them against their target, or reversely, by inhibiting them for instance if their excessive activity is at the origin of a detrimental side effect. According to a particular aspect, a typical application of a kinase reprogramming method according to the invention is the control the activity of engineered T-cells used in adoptive cell therapy against cancer. Further, a particular application of a kinase reprogramming method according to the invention can be in treatment of disorders where T-cell therapy is envisioned, notably for prevention and treatment of infections or stem cell therapy. For example, it is observed that the mutated Zap-70 kinase of the invention can be inhibited by various small inhibitor molecules and the inhibitory response of those mutated Zap-70 kinases to these inhibitors is increased as compared to wild type Zap-70, therefore offering a promising tool for modifying in vivo activity of cells expressing said mutated kinases.

According to a particular aspect, the invention relates to a method of designing mutated kinases for reprogramming the kinase sensitivity to specific inhibitors.

Another aspect of the invention relates to a method for reprogramming cell kinase sensitivity to specific inhibitors.

Another aspect of the invention relates to mutated kinases of the invention, which are sensitive to specific kinase inhibitors, in particular mutated ZAP-70 and/or Lck kinases of the invention.

Another aspect of the invention relates to an isolated nucleic acid molecule encoding a mutated kinase according to the invention.

Another aspect of the invention relates to an isolated cell expressing at least one kinase mutant of the invention, in particular a T cell (e.g. a T-cell expressing at least one cancer-related receptor).

In another aspect, the invention provides a recombinant vector comprising a nucleic acid molecule encoding a kinase mutant according to the invention.

Another aspect of the invention provides a composition comprising an isolated cell (e.g. T cell, in particular a T-cell expressing at least one cancer-related receptor) expressing at least one kinase mutant of the invention or a recombinant vector according to the invention such as for example a pharmaceutical composition comprising cells of the invention or at least one recombinant vector according to the invention and at least one pharmaceutically acceptable carrier, diluent or excipient thereof.

Another aspect of the invention relates to an isolated cell (e.g. T cell, in particular a T-cell expressing at least one cancer-related receptor) expressing at least one kinase mutant of the invention or a recombinant vector according to the invention for use as a medicament. Another aspect of the invention provides an ex vivo method (e.g. in culture) of inducing the expression of at least one kinase mutant of the invention in a cell (e.g. a T cell, in particular a T-cell expressing at least one cancer-related receptor) comprising the step of ex vivo transducing said cell with a vector according to the invention.

Another aspect of the invention provides a method of inducing in vivo the expression of at least one kinase mutant of the invention in a target cell a cell (e.g. a T cell, in particular a T-cell expressing at least one cancer-related receptor) in a subject in need thereof, said method comprising the steps of administering a vector encoding at least one kinase mutant according to the invention to said subject under suitable conditions for inducing transduction of the subject's target cell in vivo with said vector.

Another aspect of the invention relates to mutated kinases of the invention which are sensitive to at least one specific kinase inhibitor, isolated cells expressing at least one of those mutated kinases or a recombinant vector comprising a nucleic acid molecule encoding at least one of those mutated kinases, for use in controlling the activity of the cells expressing those and in particular for use in the treatment of a disorder or disease, more particularly, a cancer, in combination with said specific at least one kinase inhibitor.

Another aspect of the invention relates to the use of mutated kinases of the invention which are sensitive to specific kinase inhibitors, of isolated cells expressing at least one of those mutated kinases or of a recombinant vector comprising a nucleic acid molecule encoding at least one of those mutated kinases, for the preparation of a pharmaceutical composition for controlling the activity of the cells expressing those and in particular for the treatment of a disorder or disease, more particularly a cancer.

Another aspect of the invention provides a method of treating a disorder or disease in a subject in need thereof, said method comprising administering an effective amount of mutated kinases of the invention, of isolated cells expressing at least one of those mutated kinases or of a recombinant vector comprising a nucleic acid molecule encoding at least one of those mutated kinases, in a subject in need thereof.

Another aspect of the invention provides a kit comprising at least one mutated kinases of the invention, of isolated cells expressing at least one of those mutated kinases or of a recombinant vector comprising a nucleic acid molecule encoding at least one of those mutated kinases according to the invention.

DETAILED DESCRIPTION

Figure 1:
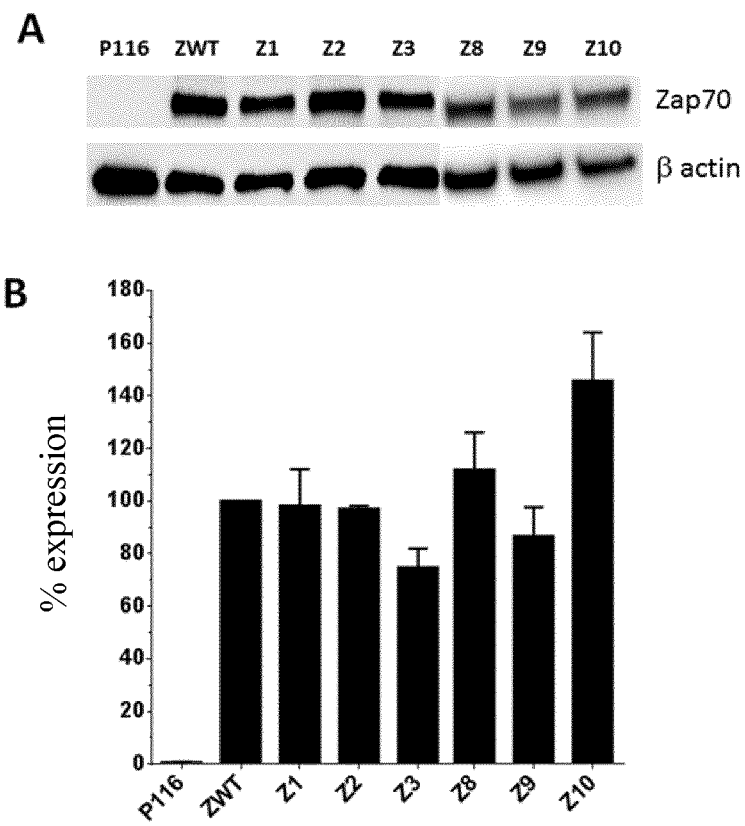
FIG. 1 shows the expression profile of Zap-70 mutants (Z1-Z3 and Z8-Z10) in P116 cells as analysed by western blot (A) and quantified as % of expression (B) as described in Example 3, 100% expression corresponding to the expression of the Zap-70 wild-type (ZWT).

The term "drug candidate" includes any agent which is developmental drug, a drug submitted for approval, an investigational, approved or marketed drug.

The term "approved drug" includes any agent that has been approved for pharmaceutical or veterinary use by a health authority.

The term "cell-based therapies" relates to the therapy that can be used e.g. in cancer immunotherapy and include transfer of various lymphocytes and antigen-presenting cells (APC) into the subject. A type of cell-based therapy is called "adoptive cell therapy" or "ACT" and includes transfer of T lymphocytes. The cells may be autologous, i.e. originating from the subject to be treated and been altered before being transferred back, or, they may have come from another subject (heterologous).

The term "bind" in relation to an inhibitor means an inhibitor which sticks to or has an affinity for an active site of kinase through one or more hydrophobic, hydrophilic, hydrogen, and/or ionic bonds, or, in the case of non-competitive inhibitors, through covalent bonds.

The terms "mutant kinase" or "modified kinase" refers to a kinase of the invention having an amino acid sequence differing from the amino acid at sequence of the wild-type kinase at one or more positions.

The term "cancer-related T-cell receptor" or "cancer-related TCR" refers to a TCR that recognizes at least one cancer-associated antigen. T cells expressing at least one TCR can be used for immunotherapy of cancer through adoptive cell therapy (Rosenberg et al., 2015, supra; *Khalilet al.*, 2016, *supra*). Examples of design of T cells expressing at least one TCR are provided under Irving et al., 2012, *Journal of Biological Chemistry*, 287(27), 23068-23078.

The term a "chimeric antigen receptor" or "CAR" refers to an engineered receptor, which grafts an arbitrary specificity onto an immune effector cell. Typically, these receptors are used to graft the specificity of a monoclonal antibody onto a T cell with transfer of their coding sequence facilitated by retroviral vectors. The receptors are called chimeric because they are composed of parts from different sources. T cells expressing at least one CAR can be used for immunotherapy of cancer through adoptive cell therapy. Examples of design of T cells expressing at least one CAR are provided under *Kalos et al.,* 2011, Sci Transl Med., (95): 95ra73 and U.S. Pat. No. 9,499,629.

The term "stem-cell therapy" refers to the use of stem cells to treat or prevent a disease or condition. Examples of used stem-cell therapy include bone marrow transplant and the therapies with the use of umbilical cord blood. Research is underway to develop further sources for stem cells, and to apply stem-cell treatments for neurodegenerative diseases and conditions such as diabetes, heart disease, and other conditions (*Fox et al.,* 2014, Science 345(6199): 1247391; *Kimbrel et al.,* 2015, Nature Reviews. Drug Discovery, 14(10), 681-692).

The terms "cancers" or "tumors" as defined herewith are diseases involving abnormal cell growth with the potential to invade or spread to other parts of the body. Term "cancers" designate diseases exemplified by, but not limited to, carcinomas (such as breast, prostate, lung, pancreas, and colon cancers), melanomas, sarcomas (such as bone, cartilage, nerve cancer), lymphomas and leukemias (hematopoietic cancers), germ cell tumors (such as seminoma and dysgerminoma) and blastomas.

As used herein, "treatment" and "treating" and the like generally mean obtaining a desired pharmacological and physiological effect. The effect may be therapeutic in terms of a partial or complete cure of a disease, condition, symptom or adverse effect attributed to the disease or to the used treatment. The term "treatment" as used herein covers any treatment of a cancer in a mammal, particularly a human, and includes inhibiting the disease, i.e., arresting its development; or relieving the disease, i.e., causing regression of the disease and/or its symptoms or conditions such as improvement or remediation of damage. In particular, the cells, vectors, methods, uses, formulations and compositions according to the invention are useful in the treatment of a cancer and/or in the prevention of evolution of a cancer into an advanced or metastatic stage in patients with early stage cancer, thereby improving the cancer staging and patient prognosis. In particular, treatment of a cancer may include administration of cells according to the invention.

The term "efficacy" of a treatment or method according to the invention can be measured based on changes in the course of disease or condition in response to a use or a method according to the invention. For example, the efficacy of a treatment or method according to the invention can be measured by its impact on signs or symptoms of illness. A response is achieved when the subject experiences partial or total alleviation, or reduction of unwanted symptoms of illness. According to a particular embodiment, the efficacy can be measured through the assessing of reduction of side effects (e.g. auto-immune response) observed after reinjection of modified T cells of the invention into a subject in combination with a corresponding specific kinase inhibitor in adoptive cell therapy as compared to standard adoptive cell therapy with modified T cells not expressing the kinase mutants of the invention or with modified T cells expressing kinase mutants but in absence of specific kinase inhibitor. The term "effective amount" as used herein refers to an amount of at least one cell or recombinant vector according to the invention, or a pharmaceutical formulation thereof, that elicits a detectable reduction of the symptoms of the disease in a subject that is being administered said cells, these symptoms can include, for instance decrease in side effects, increase in duration of treatment or dosage before those side effects appear etc.

The term "subject" as used herein refers to mammals. For examples, mammals contemplated by the present invention include human, primates, domesticated animals such as cattle, sheep, pigs, horses, laboratory rodents, other pets and the like.

Examples of "conservative substitution" include substitution of one aliphatic residue for another, such as Ile, Val, Leu, or Ala for one another, or substitutions of one polar residue for another, such as between Lys and Arg; Glu and Asp; or Gln and Asn. Amino acid hydrophobicity can be found on the basis of known scales such as *Kyte, et al*, 1982, *J. Mol. Biol.*, 157: 105-131; *Eisenberg*, 1984, *Ann. Rev. Biochem.* 53: 595-623. Other such conservative substitutions, for example, substitutions of entire regions having similar hydrophobicity characteristics or a-helical propensity, are well known (*Kyte, et al*, 1982, *supra*). For example, a "conservative amino acid substitution" may involve a substitution of a native amino acid residue with a non-native residue such that there is little or no effect on the polarity or charge of the amino acid residue at that position. Desired amino acid substitutions (whether conservative or non-conservative) can be determined by those skilled in the art at the time such substitutions are desired. Exemplary amino acid substitutions are presented in Table 1 below.

TABLE 1

| Amino acids | Examples of « conservative » substitutions |
|---|---|
| Ala (A) | Val, Leu, Ile, Pro |
| Arg (R) | Lys, His |
| Asn (N) | Gln |
| Asp (D) | Glu |
| Cys (C) | Ser, Ala, Thr |
| Gln (Q) | Asn |
| Glu (E) | Asp |
| Gly (G) | Pro, Ala |
| His (H) | Lys, Arg, |
| Ile (I) | Leu, Val, Met, Ala, Phe, Tyr |
| Leu (L) | Ile, Val, Met, Ala, Phe, Tyr |
| Lys (K) | Arg, His |
| Met (M) | Val, Leu, Ile, Phe |
| Phe (F) | Leu, Val, Ile, Ala, Tyr, Trp |
| Pro (P) | Ala, Gly |

TABLE 1-continued

| Amino acids | Examples of « conservative » substitutions |
|---|---|
| Ser (S) | Thr, Ala, Cys |
| Trp (W) | Phe, Tyr |
| Thr (T) | Ser |
| Tyr (Y) | Trp, Phe, Thr, Ser |
| Val (V) | Ile, Met, Leu, Phe, Ala, Pro |

Method of Designing Mutated Kinases and Uses thereof

According to a first aspect, the invention provides a method for designing kinase mutants with reprogrammed sensitivity to specific inhibitors comprising the steps of:
a) selecting a target kinase involved in a disease-related biological pathway;
b) selecting an agent, in particular drug candidate (e.g. an inhibitor of a kinase), not being an inhibitor of the target kinase (foreign kinase) having little or no affinity for the wild-type target kinase and having little cross-reactivity with other kinases than the foreign kinase;
c) mutating the target kinase sequence to render it sensitive to said agent having little or no affinity for the wild-type target kinase, while keeping functional activity of the wild-type target kinase for the mutated target kinase in absence of said agent;
d) confirming selective binding affinity of the said agent to the mutated sequence obtained under c) compared to said wild-type target kinase;
e) confirming functional activity of the said mutated target kinase in absence of said agent;
f) obtaining a mutated kinase sequence being sensitive to said agent which is not an inhibitor of the said wild-type target kinase (foreign kinase) with functional activity of the said wild-type target kinase in absence of said agent.

According to a further aspect, the invention provides a method for designing kinase mutants with reprogrammed sensitivity to specific inhibitors comprising the steps of:
a) selecting a target kinase involved in a disease-related biological pathway;
b) selecting an inhibitor of a kinase not being the target kinase (foreign kinase) having little or no affinity for the wild-type target kinase and having little cross-reactivity with other kinases than the foreign kinase;
c) mutating the target kinase sequence to render it sensitive to said kinase inhibitor having little or no affinity for the wild-type target kinase, while keeping functional activity of the wild-type target kinase for the mutated target kinase in absence of said kinase inhibitor;
d) confirming selective binding affinity of the said inhibitor to the mutated sequence obtained under c) compared to said wild-type target kinase;
e) confirming functional activity of the said mutated target kinase in absence of said kinase inhibitor;
f) obtaining a mutated kinase sequence being sensitive to a kinase inhibitor of a kinase not being the said wild-type target kinase (foreign kinase) and with functional activity of the said wild-type target kinase in absence of said kinase inhibitor.

According to a particular aspect, step c) can further comprise the steps of:
c1) calculating the total binding free energy and the contribution of each residue for the binding of the foreign kinase inhibitor to the foreign kinase;
c2) deriving from the total binding free energy and the contribution of each residue for the binding in the foreign kinase obtained in c1) possible mutations in the sequence of the wild-type target kinase;

c3) estimating the total binding free energy, and the contribution of each residue, for the binding of the foreign kinase inhibitor to the mutated target kinase.

The absolute binding free energy for the inhibitor/kinase association can be calculated using various methods including Molecular Mechanics-Generalized Born Surface Area (MM-GBSA) approach (*Zoete et al., 2013, Zoete et al., 2013, Front Immunol.*, 4, 268; *Zoete et al., 2005, Proteins* 61: 79-93; *Zoete et al., 2007, Proteins*, 67: 1026-1047; *Zoete et al., 2010, J. Mol. Recogn.*, 23: 142-152).

According to another particular aspect, step c) can further comprise the step of experimental yeast or phage display to design a mutated kinase of step c).

According to a further particular aspect, the mutated kinase sequences of the invention can be used to design expressing systems thereof for expressing the said mutated kinase which are useful in compositions and methods of the invention.

According to another aspect, the invention provides a method for reprogramming cell kinase sensitivity to specific inhibitors comprising the steps of:
a) selecting a target kinase involved in a disease-related biological pathway;
b) providing an expression system for a mutant of the said target kinase wherein the sequence of said mutant corresponds to the sequence of the target kinase wherein mutations have been introduced to render it sensitive to an inhibitor of a kinase not being the target kinase (foreign kinase), which inhibitor has little or no affinity for the wild-type target kinase and has little cross-reactivity with other kinases than the foreign kinase and wherein the said mutant retains the functional activity of the wild-type target kinase in absence of said kinase inhibitor;
c) modifying a cell of a living organism with an expression system under b) for inducing the said cell to produce a mutant of the target kinase;
d) obtaining a modified cell expressing a mutant of the target kinase, wherein the mutant of the target kinase has an activity essentially similar to the activity of the wild-type target kinase in absence of the inhibitor of the said foreign kinase and has an inhibited kinase activity compared to the wild-type target kinase in presence of said inhibitor of the said foreign kinase.

According to a further particular aspect, is provided a method of the invention wherein said inhibitor of kinase is a drug candidate.

According to a further particular aspect, is provided a method of the invention wherein said drug candidate is an approved drug.

According to another particular aspect, is provided a method of the invention for reprogramming cell kinase sensitivity to specific inhibitors, wherein said modified cells are to be administered in a subject in the need thereof in combination with said inhibitor of foreign kinase to control the activity of the modified cell, while not effecting the activity of the activity of the same non-modified cells.

For example, said method is used to control the killing activity of antigen-presenting cells in case of T-cell therapy or of cell proliferation activity in case of stem-cell therapy through the use of the specific inhibitors.

According to a particular aspect, is provided a method of the invention for reprogramming cell kinase sensitivity to specific inhibitors wherein the method is an ex vivo method.

In particular, the modified cell obtained under step d) is isolated for preparing a pharmaceutical composition.

According to another particular aspect, is provided a method of the invention for reprogramming cell kinase sensitivity to specific inhibitors wherein the modified cell obtained under step c) are administered to a living organism to induce in vivo the expression of the mutant of the target kinase under step d).

According to another particular aspect, is provided a method of the invention for reprogramming cell kinase sensitivity to specific inhibitors further comprising a step of modulating the kinase activity of said modified cell by contacting the said foreign kinase inhibitor with the said modified cell.

According to a particular aspect, the inhibitor of the kinase not being the target kinase (foreign kinase) can be selected among agents having a binding mode to their active site on the foreign kinase compatible with a binding in the active site of the target kinase. The above compatibility of binding modes can be assessed by for example molecular modelling, for instance by superimposing the 3D structure of the target kinase to that of the foreign kinase in complex with its inhibitor, and verifying that the binding of the foreign kinase inhibitor to the mutated target kinase would not require any significant conformational rearrangement of the target kinase. The complex between the foreign kinase and its inhibitor can be obtained by molecular docking.

According to another particular aspect, the inhibitor of the kinase not being the target kinase (foreign kinase) can be selected among inhibitors of a kinase having significant sequence difference in the binding site of the said inhibitor compared to the said target kinase.

According to another particular aspect, the inhibitor of the kinase not being the target kinase (foreign kinase) can be selected among agents that have no or limited side effects.

According to another particular aspect, the target kinase can be selected among kinases that are known to be involved in a disease-related biological pathway.

According to a further particular aspect, the target kinase is selected from those involved in the control of T-cells function.

According to a further particular aspect, the target kinase is selected from Zap-70 and Lck kinases.

According to a further particular aspect, the target kinase mutants are selected from the Zap-70 and Lck kinase mutants of the invention.

According to another further particular aspect, the target kinase is selected from proto-oncogene tyrosine-protein kinase Fyn (FYN), tyrosine-protein kinase CSK (or C-terminal Src kinase; CSK), tyrosine-protein kinase ITK/TSK (or interleukin-2-inducible T-cell kinase; ITK) and tyrosine-protein kinase ABL (ABL).

According to a further particular aspect, a drug candidate according to the invention is an inhibitor of a foreign kinase selected from a marketed, approved, developmental or investigational drug.

According to a further particular aspect, an inhibitor of a foreign kinase according to the invention is an agent selected from a marketed, approved, developmental or investigational drug.

Kinases According to the Invention

In one embodiment, is provided a kinase mutant obtainable by a method according to the invention.

In another further embodiment, is provided a Zap-70 kinase mutant comprising an amino acid sequence of SEQ ID NO: 1 wherein is introduced:

(i) at least one mutation selected from: V399I, M414A, M414T, M414V, M416Y, M416V, M416L, M416I, M416F, M416W, M416H, M416T and M416S (mutated SEQ ID NO: 1 sequence), and (ii) optionally, at least one conservative substitution of at least one amino acid of the said mutated SEQ ID NO: 1 on at least one position selected from 342, 344-346, 350-354, 367-369, 386, 390, 399, 412-421, 424, 466-468 and 478-480 which was not mutated under (i).

In another further embodiment, is provided a Zap-70 kinase mutant comprising an amino acid sequence of SEQ ID NO: 1 wherein is introduced:

(i) at least one mutation selected from selected from: M414A, M414T and M414V, and (ii) optionally, at least one conservative substitution of an amino acid of the said mutated SEQ ID NO: 1 on at least one position selected from 342, 344-346, 350-354, 367-369, 386, 390, 399, 412-413, 415-421, 424, 466-468 and 478-480.

In another further embodiment, is provided a Zap-70 kinase mutant comprising an amino acid sequence of SEQ ID NO: 1 wherein is introduced:

(i) at least one mutation selected from: V399I, M414A, M414T, M414V, M416Y, M416V, M416L, M416I, M416F, M416W, M416H, M416T and M416S (mutated SEQ ID NO: 1 sequence), and (ii) optionally, at least one conservative substitution of at least one amino acid of the said mutated SEQ ID NO: 1 on at least one position selected from 342, 344-346, 350-354, 367-369, 386, 390, 399, 412-421, 424, 466-468 and 478-480 which was not mutated under (i), wherein when the at least one mutation under (i) is M414A, then at least one conservative as described under (ii) is present.

In another further embodiment, is provided a Zap-70 kinase mutant comprising an amino acid sequence of SEQ ID NO: 1 wherein are introduced:

(i) at least one mutation selected from selected from: M414A, M414T and M414V and at least one mutation selected from V399I and M416Y, and (ii) optionally, at least one conservative substitution of an amino acid of the said mutated SEQ ID NO: 1 on at least one position selected from 342, 344-346, 350-354, 367-369, 386, 390, 399, 412-413, 415-421, 424, 466-468 and 478-480 which was not mutated under (i).

In another further embodiment, is provided a Zap-70 kinase mutant comprising an amino acid sequence of SEQ ID NO: 1 wherein are introduced:

(i) at least the mutation M414V and at least one mutation selected from V399I and M416Y, and (ii) optionally, at least one conservative substitution of an amino acid of the said mutated SEQ ID NO: 1 on at least one position selected from 342, 344-346, 350-354, 367-369, 386, 390, 399, 412-413, 415-421, 424, 466-468 and 478-480 which was not mutated under (i).

In another further embodiment, is provided a Zap-70 kinase mutant comprising an amino acid sequence of SEQ ID NO: 1 wherein are introduced:

(i) at least one mutation selected from selected from: M414A, M414T and M414V and the mutation V399I and the mutation M416Y, and (ii) optionally, at least one conservative substitution of an amino acid of the said mutated SEQ ID NO: 1 on at least one position selected from 342, 344-346, 350-354, 367-369, 386, 390, 412-413, 415, 417-421, 424, 466-468 and 478-480.

In another further embodiment, is provided a Zap-70 kinase mutant comprising an amino acid sequence of SEQ ID NO: 1 wherein are introduced:

(i) at least the mutation M414V and the V399I and the mutation M416Y, and (ii) optionally, at least one conservative substitution of an amino acid of the said mutated SEQ ID NO: 1 on at least one position selected from 342, 344-346, 350-354, 367-369, 386, 390, 412-413, 415, 417-421, 424, 466-468 and 478-480.

In another further embodiment, is provided a Zap-70 kinase mutant having a mutated SEQ ID NO: 1 sequence according to the invention wherein said at least one conservative substitution of an amino acid of the said mutated SEQ ID NO: 1 on at least one of the positions selected from 342, 344-346, 350-354, 367-369, 386, 390, 399, 412-421, 424, 466-468 and 478-480 which was not mutated under (i) is a conservative substitution of about 1 to 10 amino acids at those positions, for example a conservative substitution of about 1 to 5 amino acids at those positions, for another example a conservative substitution of about two, three, four or five amino acids at those positions.

In another further embodiment, is provided a Zap-70 kinase mutant comprising the following amino acid sequence:

```
                                        (SEQ ID NO: 12)
Xaa1 Xaa2 Xaa3 Xaa4 Xaa5 Xaa6 Xaa7 Xaa8 Xaa9 Xaa10

Xaa11 Xaa12 Xaa13 Xaa14 Xaa15 Xaa16 Xaa17 Xaa18

Xaa19 Xaa20 Xaa21 Xaa22 Xaa23 Xaa24 Xaa25 Xaa26
``` wherein
Xaa1 is selected from V and I;
Xaa2 is selected from R, K, and H;
Xaa3 is selected from L, I, V, M, A, F and Y;
Xaa4 is selected from I, L, V, M, A, F and Y;
Xaa5 is selected from G, P and A;
Xaa6 is selected from V, I, M, L, F, A and P;
Xaa7 is selected from C, S, T and A;
Xaa8 is selected from Q and N;
Xaa9 is selected from A, V, L, I and P;
Xaa10 is selected from E and D;
Xaa11 is selected from A, V, L, I and P;
Xaa12 is selected from L, I, V, M, A, F and Y;
Xaa13 is selected from M, V, L, I and F;
Xaa14 is selected from L, I, V, M, A, F and Y;
Xaa15 is selected from V, I, M, L, F, A and P;
Xaa16 is selected from M, A, V and T;
Xaa17 is selected from E and D;
Xaa18 is selected from M, Y and L;
Xaa19 is selected from A, V, L, I and P;
Xaa20 is selected from G, P and A;
Xaa21 is selected from G, P and A;
Xaa22 is selected from G, P and A;
Xaa23 is selected from P, A and G;
Xaa24 is selected from L, I, V, M, A, F and Y;
Xaa25 is selected from H, K and R;
Xaa26 is selected from K, R and H;
wherein SEQ ID NO: 12 is a mutated sequence of a fragment of SEQ ID NO: 1 from position 399 to 424 and therefore not identical to SEQ ID NO: 1.

In another further particular embodiment is provided a Zap-70 kinase mutant comprising an amino acid sequence of SEQ ID NO: 12, wherein when Xaa1 is I, Xaa16 can be selected from M or a conservative substitution thereof (V, L, I or F) and/or Xaa18 can be selected from M or a conservative substitution thereof (V, L, I or F).

In another further particular embodiment is provided a Zap-70 kinase mutant comprising an amino acid sequence of SEQ ID NO: 12, wherein when Xaa16 is A, T or V, Xaa1 can be selected from V or a conservative substitution thereof (I, M, L, F, A or P) and/or Xaa18 can be selected from M or a conservative substitution thereof (V, L, I or F).

In another further particular embodiment is provided a Zap-70 kinase mutant comprising an amino acid sequence of SEQ ID NO: 12, wherein when Xaa18 is L or Y, Xaa1 can be selected from V or a conservative substitution thereof (I, M, L, F, A or P) and/or Xaa16 can be selected from M or a conservative substitution thereof (V, L, I or F).

In another further particular embodiment is provided a Zap-70 kinase mutant comprising an amino acid sequence selected from SEQ ID NO: 3, SEQ ID NO: 4, SEQ ID NO: 5, SEQ ID NO: 6, SEQ ID NO: 7 and SEQ ID NO: 8.

In another further particular embodiment is provided a Zap-70 kinase mutant comprising an amino acid sequence selected from SEQ ID NO: 5, SEQ ID NO: 6 and SEQ ID NO: 8.

In another further embodiment, is provided a Zap-70 kinase mutant according to the invention wherein at least one second mutation as described under (ii) is present.

In another further embodiment, is provided a Lck kinase mutant comprising an amino acid sequence of SEQ ID NO: 2 wherein is introduced:

(a) at least one mutations selected from: T316V, T316S, Y318L, Y318W, Y318F, Y318H, Y318T, Y318S, S323C and S323A (mutated SEQ ID NO: 2 sequence) and (b) optionally, at least one conservative substitution of at least one amino acid of the said mutated SEQ ID NO: 2 on at least one position selected from 251-253, 259, 261, 271-273, 288, 292, 301, 314-327, 330, 368-371, 381-383 which was not mutated under (a).

In another further embodiment, is provided a Lck kinase mutant comprising an amino acid sequence of SEQ ID NO: 2 according to the invention wherein is introduced under a) at least one mutation, said mutation being S323C.

In another further embodiment, is provided a Lck kinase mutant comprising an amino acid sequence of SEQ ID NO: 2 according to the invention wherein is introduced under a) at least two mutations, said mutation being S323C and Y318L.

In another further embodiment, is provided a Lck kinase mutant having a mutated SEQ ID NO: 2 sequence according to the invention wherein said at least one conservative substitution of an amino acid of the said mutated SEQ ID NO: 2 on at least one of the positions selected from 251-253, 259, 261, 271-273, 288, 292, 301, 314-327, 330, 368-371, 381-383 which was not mutated under (a) is a conservative substitution of about 1 to 10 amino acids at those positions, for example a conservative substitution of about 1 to 5 amino acids at those positions, for another example a conservative substitution of about two, three, four or five amino acids at those positions.

In another further embodiment, is provided a Lck kinase mutant comprising the following amino acid sequence (SEQ ID NO: 13)
Xab1 Xab2 Xab3 Xab4 Xab5 Xab6 Xab7 Xab8 Xab9 wherein
Xab1 is selected from T, V and S;
Xab2 is selected from E and D;
Xab3 is selected from Y and L;
Xab4 is selected from M, V, L, I and F;
Xab5 is selected from E and D;
Xab6 is selected from N and Q;
Xab7 is selected from G, P and A;
Xab8 is selected from S, C, T and A;
Xab9 is selected from L, I, V, M, A, F and Y;

wherein SEQ ID NO: 13 is a mutated sequence of a fragment of SEQ ID NO: 2 from position 316 to 324 and therefore not identical to SEQ ID NO: 2.

In another further particular embodiment is provided a Lck kinase mutant comprising an amino acid sequence of SEQ ID NO: 13, wherein when Xab1 is V, Xab3 can be selected from Y or a conservative substitution thereof (W, F, T or S) and/or Xab8 can be selected from S or a conservative substitution thereof (T, A or C).

In another further particular embodiment is provided a Lck kinase mutant comprising an amino acid sequence of SEQ ID NO: 13, wherein when Xab3 is L, Xab1 can be selected from T or a conservative substitution thereof (S) and/or Xab8 can be selected from S or a conservative substitution thereof of (T, A or C).

In another further particular embodiment is provided a Lck kinase mutant comprising an amino acid sequence of SEQ ID NO: 13, wherein when Xab8 is C, Xab1 can be selected from T or a conservative substitution thereof (S) and/or Xab3 can be selected from Y or a conservative substitution thereof (W, F, T or S).

In another further particular embodiment, is provided a Lck kinase mutant comprising an amino acid sequence selected among: SEQ ID NO: 9, SEQ ID NO: 10 and SEQ ID NO: 11.

In another further particular embodiment, is provided a Lck kinase mutant comprising an amino acid sequence selected from SEQ ID NO: 11 and SEQ ID NO: 20.

Nucleic Acids of the Invention

Isolated nucleic acid encoding a kinase mutant according to the invention may be, for instance, natural DNA or RNA or a recombinant or synthetic DNA, RNA or LNA or a recombinant nucleic acid molecule. For example isolated nucleic acid encoding a kinase mutant of the invention comprises any of the nucleic acid molecules according to the invention either alone or in combination.

In a particular embodiment, is provided an isolated nucleic acid molecule encoding at least one, and in particular one, kinase mutant according to the invention.

In a more particular embodiment, is provided an isolated nucleic acid molecule encoding a kinase according to the invention, wherein the said nucleic acid molecule is selected from SEQ ID NO: 14, SEQ ID NO: 15, SEQ ID NO: 16, SEQ ID NO: 17, SEQ ID NO: 18, SEQ ID NO: 19.

Vectors and Methods for Cell Transduction

In one embodiment, the invention provides a recombinant vector comprising a nucleic acid molecule encoding at least one kinase mutant according to the invention.

In one embodiment, the invention provides a recombinant expression vector comprising a nucleic acid molecule according to the invention, wherein the vector optionally comprises an expression controlling sequence, allowing expression in eukaryotic host cells of the encoded sequence, operably linked to said nucleic acid molecule.

Numerous expression systems can be used, including without limitation chromosomes, episomes, plasmids, and virus-derived vectors. More particularly, the recombinant vectors used can be derived from bacterial plasmids, transposons, yeast episomes, insertion elements, yeast chromosome elements, viruses such as baculovirus, papilloma viruses such as SV40, vaccinia viruses, adenoviruses, fox pox viruses, pseudorabies viruses, retroviruses, lentiviruses, adeno-associated viruses (AAV).

In a particular embodiment, the recombinant vector is a lentiviral vector.

A recombinant expression vector according to the invention may comprise nucleic acid molecules encoding for one or more than one of kinase mutant of the invention.

The nucleic acid sequence can be inserted in the recombinant expression vector by methods well known to a person skilled in the art such as, for example, those that are described in *Molecular Cloning: A Laboratory Manual, Sambrook et al., 4$^{th}$ Ed., Cold Spring Harbor Laboratory Press, Cold Spring Harbor, N.Y.*, 2001.

Recombinant vectors can include nucleotide sequences that allow, control or regulate the expression and the transcription of a polynucleotide of the invention as well as the translation of a kinase of the invention, these sequences being selected according to the host cells that are used.

In a further embodiment, is provided a host cell comprising a recombinant vector according to the invention.

According to a particular embodiment, said host cell is a T cell, in particular a T cell engineered to express at least a cancer related TCR or a chimeric antigen receptor (CAR).

The introduction of the recombinant vector in a host cell can be carried out according to methods that are well known to a person skilled in the art, such as those described in *Basic Methods in Molecular Biology, Davis et al., 2$^{nd}$ ed., McGraw-Hill Professional Publishing*, 1995, *and Molecular Cloning: A Laboratory Manual*, supra, such as transfection by calcium phosphate, transfection by DEAE dextran, transfection, microinjection, transfection by cationic lipids, electroporation, transduction or infection.

According to a particular embodiment is provided a cell expressing at least one kinase mutant according to the invention.

According to a particular aspect, cells of the invention are selected from T cells, T-cells targeting antigen-presenting cancer cells, such as tumors infiltrating T-cells (TIL) and engineered T-cells (producing an optimized TCR or a CAR).

According to an embodiment, the invention provides a T cell expressing at least one kinase mutant according to the invention and at least one cancer related T-cell receptor. Examples of cancer related T-cell receptor are TRC BC1 (β-chain of an HLA-A*0201-restricted NY-ESO-$_{1157-165}$-specific TCR (*Irving et al., 2012, supra*).

According to an embodiment, is provided a cell composition comprising isolated cells of the invention.

According to one embodiment, the expression level of kinase mutants can be measured by methods such as Western Blot.

In another embodiment, the invention provides cells expressing at least one kinase mutant of the invention wherein the mutant has a kinase activity essentially similar to the activity of the wild-type target kinase in absence of the inhibitor of the said foreign kinase and has an enhanced ability to respond to selected foreign kinase inhibitors as compared to non-modified cells (i.e. expressing the kinase wild-type but not expressing the kinase mutant of the invention). The kinase response of the cells expressing at least one kinase mutant of the invention as compared to the response to the wild-type cells can be assessed by methods such as testing cells' ability of production of IL-2 or cell viability in cell-based assay. In a particular aspect, is provided a process for producing a cell capable of expressing at least one kinase mutant of the invention, comprising contacting said cell with a vector or a nucleic acid according to the invention.

According to a particular aspect is provided an ex vivo method (i.e. in culture) of inducing expression of at least one kinase mutant of the invention in a cell, in particular a T cell, comprising a step of ex vivo transducing said cell with a vector according to the invention. Another aspect of the invention provides a method of inducing in vivo the expression of at least one kinase mutant of the invention in a cell, in particular a T cell, in a subject in need thereof, said method comprising the step of administering a vector encoding at least one kinase mutant according to the invention to said subject under suitable conditions for inducing transduction of the subject's cells in vivo with said vector.

Methods and Uses according to the Invention

Kinase mutants and methods of expressing thereof advantageously allow to reprogram the activity of target kinases in cells in rendering them sensitive to an inhibitor of another kinase than said target kinase (foreign kinase) and thereby allow controlling the activity of a biological pathway through the combined use of cells expressing kinase mutants of the invention and said inhibitor of said foreign kinase, without affecting the same biological pathway in cells not expressing the kinase mutants of the invention since the activity of the biological pathway of interest is altered reversibly in modified cells expressing the kinase mutant of the invention upon administration of the kinase inhibitor, while the activity of said pathway will remain unchanged in non-modified cells. This is particularly useful since this method can be applied not only directly to cells at the origin of the disorder but also indirectly be applied to cells involved in the control or destruction of the disease-related cells such as cells from the immune system. The activity of a target biological pathway can be controlled via the administration of a kinase inhibitor and through a window of time of its effect.

Another aspect of the invention provides mutated kinases of the invention, isolated cells expressing at least one of those mutated kinases or recombinant vectors comprising a nucleic acid molecule encoding at least one of those mutated kinases which are useful for controlling the activity of the cells expressing those and in particular for use in the treatment of a disorder or disease, in particular cancer, in combination with a specific kinase inhibitor.

According to a particular aspect, the invention provides mutated kinase mutants obtainable according to the invention, a recombinant vector expressing at least one of said mutants, an isolated cell expressing at least one said kinase mutants for use in the treatment of a disorder or disease selected from cancer, autoimmune diseases, asthma, diabetes, inflammatory diseases and neurodegenerative diseases or during or after an organ transplant.

According to a particular aspect, the invention provides mutated kinase mutants obtainable according to the invention, a recombinant vector expressing at least one of said mutants, an isolated cell expressing at least one said kinase mutants for controlling the activity of a cell expressing said at least one mutants.

According to a particular aspect, the invention provides mutated kinase mutants obtainable according to the invention, a recombinant vector expressing at least one of said mutants, an isolated cell expressing at least one said kinase mutants for use in a method of treatment of the invention or a method of controlling the activity of a cell expressing said at least one mutants according the invention, in combination with a specific kinase inhibitor wherein said at least one kinase inhibitor is erlotinib.

According to a particular aspect, the invention provides mutated kinase mutants obtainable according to the invention, a recombinant vector expressing at least one of said mutants, an isolated cell expressing at least one said kinase mutants for use in a method of treatment of the invention or a method of controlling the activity of a cell expressing said at least one mutants according the invention, in combination with a specific kinase inhibitor wherein said at least one kinase inhibitor is gefitinib.

According to another aspect, the invention provides a method of inducing expression of at least one kinase mutant of the invention in a cell comprising the step of transducing said cell with a vector according to the invention. The method of inducing expression of at least one kinase mutant of the invention in cells can be an ex vivo or in vivo method.

Another aspect of the invention provides a method of treating a disorder or disease in a subject in need thereof, said method comprising administering an effective amount of mutated kinases of the invention, of isolated cells expressing at least one of those mutated kinases or of a recombinant vector comprising a nucleic acid molecule encoding at least one of those mutated kinases, in a subject in need thereof.

According to another particular aspect, mutated kinases of the invention, isolated cells expressing at least one of those mutated kinases or recombinant vectors comprising a nucleic acid molecule encoding at least one of those mutated kinases are useful in the treatment of diseases selected from cancer, autoimmune diseases, asthma, diabetes, infectious and inflammatory diseases, neurodegenerative diseases or during or after an organ transplant or stem cell therapy.

According to a further particular aspect, mutated kinases of the invention, isolated cells expressing at least one of those mutated kinases or recombinant vectors comprising a nucleic acid molecule encoding at least one of those mutated kinases are useful in the treatment of cancer subjects, in particular by cancer immunotherapy, in particular through adoptive cell therapy. According to a particular aspect, the activity of the isolated cells expressing at least one of those mutated kinases or recombinant vectors comprising a nucleic acid molecule encoding at least one of those mutated kinases can be modulated (down or up-regulated, depending on the target mutation) in immunotherapy of cancer based on the (re)introduction of such cells in patients.

According to another further particular aspect, is provided a method of treatment of a cancer subject through adoptive cell therapy wherein engineered T cells for expressing at least one cancer related TCR are further engineered to express at least one kinase mutant of the invention. In a further particular aspect, those cells are engineered autologous cells, i.e. originating from the subject to be treated and being engineered.

According to another particular aspect, mutated kinases of the invention, isolated cells expressing at least one of those mutated kinases or recombinant vectors comprising a nucleic acid molecule encoding at least one of those mutated kinases are useful in the treatment of side effects of an organ transplant in a subject in need thereof.

In a particular embodiment, is provided an in vivo method of inducing expression of a kinase mutant of the invention in a cell, comprising the step of delivering a kinase-expressing vector via systemic (e.g., intravenous) or local (e.g., intra-tumoral, peri-tumoral, lymphnodal, etc.) routes to a cancer subject.

According to another particular aspect, is provided a Zap-70 kinase mutant or a Lck kinase mutant or a recombinant vector comprising a nucleic acid molecule encoding said kinase mutant or an isolated cell expressing said kinase mutant or a composition thereof according to the invention for use in combination with at least one kinase inhibitor selected from erlotinib, vandetanib, gefitinib and afatinib, in particular erlotinib, vandetanib and gefitinib for controlling the activity of a cell expressing those, in particular for use in the treatment of a disorder or disease selected from a cancer, an autoimmune disease or disorder, asthma, diabetes, an infectious or inflammatory disease, a neurodegenerative disease or during or after an organ transplant or a stem cell therapy.

According to another particular aspect, is provided a Zap-70 kinase mutant or a Lck kinase mutant or a recombinant vector comprising a nucleic acid molecule encoding said kinase mutant or an isolated cell expressing said kinase mutant or a composition thereof according to the invention for use in combination with at least one kinase inhibitor selected from erlotinib, vandetanib, gefitinib and afatinib, in particular erlotinib, vandetanib and gefitinib for controlling the activity of a cell expressing those, in particular for use in the treatment of a disorder or disease selected from a cancer, an autoimmune disease or disorder, asthma, diabetes, an infectious or inflammatory disease, a neurodegenerative disease or during or after an organ transplant or a stem cell therapy, wherein said Zap-70 kinase mutant comprises an amino acid sequence of SEQ ID NO: 1 wherein is introduced (i) at least one mutation selected from: V399I, M414A, M414T, M414V, M416Y, M416V, M416L, M416I, M416F, M416W, M416H, M416T and M416S (mutated SEQ ID NO: 1 sequence), and (ii) optionally, at least one conservative substitution of at least one amino acid of the said mutated SEQ ID NO: 1 on at least one position selected from 342, 344-346, 350-354, 367-369, 386, 390, 399, 412-421, 424, 466-468 and 478-480 which was not mutated under (i) and wherein said Lck kinase mutant comprises an amino acid sequence of SEQ ID NO: 2 wherein is introduced (a) at least one mutations selected from: T316V, T316S, Y318L, Y318W, Y318F, Y318H, Y318T, Y318S, S323C and S323A (mutated SEQ ID NO: 2 sequence) and (b) optionally, at least one conservative substitution of at least one amino acid of the said mutated SEQ ID NO: 2 on at least one position selected from 251-253, 259, 261, 271-273, 288, 292, 301, 314-327, 330, 368-371 and 381-383 which was not mutated under (a).

According to another particular embodiment, Zap-70 kinase mutants of the invention comprising an amino acid sequence selected from SEQ ID NO: 3, SEQ ID NO: 4, SEQ ID NO: 5, SEQ ID NO: 6, SEQ ID NO: 7 and SEQ ID NO: 8, isolated cells (e.g. T-cells) expressing at least one of those mutants or of a recombinant vector comprising a nucleic acid molecule encoding at least one of those mutants are particularly useful in a treatment according to the invention in combination with a kinase inhibitor selected from Vandetanib and Erlotinib.

According to a further particular embodiment, Zap-70 kinase mutants of the invention comprise an amino acid sequence selected from SEQ ID NO: 5, SEQ ID NO: 6, SEQ ID NO: 7 and SEQ ID NO: 8.

According to a further particular embodiment, Zap-70 kinase mutants of the invention comprising an amino acid sequence selected from SEQ ID NO: 3 and SEQ ID NO: 8, isolated cells (e.g. T-cells) expressing at least one of those mutants or of a recombinant vector comprising a nucleic acid molecule encoding at least one of those mutants are particularly useful in a treatment according to the invention in combination with Vandetanib.

According to another further particular embodiment, Zap-70 kinase mutants of the invention comprising an amino acid sequence of SEQ ID NO: 8, isolated cells (e.g. T-cells) expressing at least one of those mutants or of a recombinant vector comprising a nucleic acid molecule encoding at least one of those mutants are particularly useful in a treatment according to the invention in combination with Vandetanib.

According to another further particular embodiment, Zap-70 kinase mutants of the invention comprising an amino acid sequence selected from SEQ ID NO: 6 and SEQ ID NO: 8, isolated cells (e.g. T-cells) expressing at least one of those mutants or of a recombinant vector comprising a nucleic acid molecule encoding at least one of those mutants are particularly useful in a treatment according to the invention in combination with Erlotinib.

According to another further particular embodiment, Zap-70 kinase mutants of the invention comprising an amino acid sequence selected from SEQ ID NO: 5, SEQ ID NO: 7 and SEQ ID NO: 8, isolated cells (e.g. T-cells) expressing at least one of those mutants or of a recombinant vector comprising a nucleic acid molecule encoding at least one of those mutants are particularly useful in a treatment according to the invention in combination with Erlotinib. In another further embodiment, Lck kinase mutants of the invention comprising an amino acid sequence selected from SEQ ID NO: 9 and SEQ ID NO: 10, isolated cells (e.g. T-cells) expressing at least one of those mutants or of a recombinant vector comprising a nucleic acid molecule encoding at least one of those mutants are particularly useful in a treatment according to the invention in combination with a kinase inhibitor selected from Gefitinib and Erlotinib.

In another further embodiment, Lck kinase mutant of the comprising an amino acid sequence of SEQ ID NO: 11, isolated cells (e.g. T-cells) expressing at least one of those mutants or of a recombinant vector comprising a nucleic acid molecule encoding at least one of those mutants are particularly useful in a treatment according to the invention in combination with Erlotinib.

In another further embodiment, Lck kinase mutants of the invention comprising an amino acid sequence selected from SEQ ID NO: 11 and SEQ ID NO: 20, isolated cells (e.g. T-cells) expressing at least one of those mutants or of a recombinant vector comprising a nucleic acid molecule encoding at least one of those mutants are particularly useful in a treatment according to the invention in combination with Gefitinib.

In another further embodiment, Lck kinase mutant of the invention, isolated cells (e.g. T-cells) expressing at least one of those mutants or of a recombinant vector comprising a nucleic acid molecule encoding at least one of those mutants are used in a treatment according to the invention in combination with Afatinib.

Compositions According to the Invention

Pharmaceutical compositions or formulations according to the invention may be administered as a pharmaceutical formulation, which contains kinase mutant-expressing vectors or isolated cells as described herein.

Another aspect of the invention provides a pharmaceutical composition comprising cells of the invention and at least one pharmaceutically acceptable agent able to inhibit the activation of the cell.

The invention provides pharmaceutical or therapeutic cells as compositions and methods for treating a subject, preferably a mammalian subject, and most preferably a human patient who is suffering from a cancer, in particular through adoptive cell therapy.

The compositions according to the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral use by injection or continuous infusion. Injectable compositions are typically based upon injectable sterile saline or phosphate-buffered saline or other injectable carriers known in the art. Such pharmaceutical compositions and unit dosage forms thereof may comprise ingredients in conventional proportions, with or without additional active compounds or principles, and such unit dosage forms may contain any suitable effective amount of the active ingredient commensurate with the intended dosage range to be employed.

Compositions of this invention may also be formulated as a depot preparation, which may be administered by implantation or by intramuscular injection.

The compounds of this invention can also be administered in sustained release forms or from sustained release drug delivery systems.

According to a particular embodiment, compositions according to the invention are for intravenous use, intratumoral use, subcutaneous use or intralymphnodal use.

In another particular aspect, compositions according to the invention are adapted for delivery by single administration.

According to a particular embodiment, compositions of the invention are veterinary compositions.

In another aspect, the invention provides compositions comprising vectors according to the invention.

In another aspect, the invention provides compositions comprising kinase mutant-expressing cells according to the invention.

Further materials as well as formulation processing techniques and the like are set out in *Part 5 of Remington's "The Science and Practice of Pharmacy"*, 22$^{nd}$ *Edition*, 2012, *University of the Sciences in Philadelphia, Lippincott Williams & Wilkins*, which is incorporated herein by reference.

Mode of Administration

Vectors, cells and formulations thereof according to this invention may be administered in any manner including parenterally, intravenously, intratumorally, subcutaneously, intra-dermally, rectally, by direct tissue perfusion during surgery, or combinations thereof.

Parenteral administration includes, but is not limited to, intravenous, intra-arterial, intra-peritoneal, subcutaneous and intramuscular. The compositions of this invention may also be administered in the form of an implant, which allows slow release of the compositions as well as a slow controlled i.v. infusion.

The kinase inhibitors can be administered before, concomitantly or sequentially the administration of the vectors, cells or formulations thereof according to the invention via the same or a different route.

Combination

According to the invention, the vectors and cells according to the invention, and pharmaceutical formulations thereof, can be administered alone or in combination with a co-agent.

The invention encompasses the administration of vectors or cells, pharmaceutical formulations thereof, or composition according to the invention, wherein said vectors or cells or compositions are administered to an individual prior to, simultaneously or sequentially with other therapeutic regimens, such as for example co-agents useful in the treatment of a cancer, in a therapeutically effective amount.

Cells or composition according to the invention, or the pharmaceutical formulation thereof, that are administered simultaneously with said co-agents can be administered in the same or different composition(s) and by the same or different route(s) of administration.

Kits

According to another aspect of the invention, is provided a kit comprising at least one mutated kinases of the invention, isolated cells expressing at least one of those mutated kinases of the invention or recombinant vectors comprising a nucleic acid molecule encoding at least one of those mutated kinases and optionally instructional material.

According to a further embodiment, the kit according to the invention comprises at least one recombinant expression vector.

According to a further embodiment, the kit according to the invention comprises at least one recombinant expression vector and at least one agent kinase inhibitor.

According to a particular aspect, the kits of the invention are useful in the methods of the invention, in particular in the preparation of pharmaceutical compositions according to the invention or in methods of screening of therapeutic agents, in particular kinase inhibitors.

Patients

In an embodiment, patients according to the invention are suffering from asthma, diabetes, an infectious disease such as tuberculosis, an inflammatory disease, an autoimmune disease or disorder, a neurodegenerative disease such as Parkinson's disease or a cancer.

In an embodiment, patients according to the invention are subject of an organ transplant.

In an embodiment, patients according to the invention are suffering from any type of disease or disorder that can be treated by cell-based therapy, including but not limited to a cancer, an infectious or inflammatory disease, a neurodegenerative disease and acute heart damage.

In a further embodiment, patients according to the invention are suffering from a cancer.

In a particular embodiment, subjects according to the invention are suffering from a cancer selected from melanoma, breast cancer, ovarian cancer, prostate cancer, pancreatic cancer, brain cancer, kidney cancer, spinal cancer, non-Hodgkin lymphoma, leukemia and myeloma.

In another embodiment, patients according to the invention are undergoing stem cell therapy.

In a further embodiment, patients according to the invention are undergoing stem cell therapy for tissue regeneration such as corneal regeneration.

References cited herein are hereby incorporated by reference in their entirety. The present invention is not to be limited in scope by the specific embodiments and drawings described herein, which are intended as single illustrations of individual aspects of the invention, and functionally equivalent methods and components are within the scope of the invention.

EXAMPLES

The following abbreviations refer respectively to the definitions below:

293T cells (cells isolated from human embryonic kidneys and transformed with large T antigen); $\Delta\Delta G_{bind,sum}$ (a difference between binding free energy sum for wild type and mutated system); ALK (anaplastic lymphoma kinase); c-Met (hepatocyte growth factor receptor, also known as HGFR); DMSO (dimethyl sulfoxide); EML (echinoderm microtubule protein); EGFR (epidermal growth factor receptor or ErbB-1); ErbB-2 (Receptor tyrosine-protein kinase erbB-2, also known as CD340); ErbB-4 (Receptor tyrosine-protein kinase erbB-4); FDA (U.S. Food and Drug Administration); IL-2 (interleukin 2); KD (equilibrium dissociation constant); L1, L2, L4, L7 (Lck mutants experimental IDs); LWT (Lck wild-type kinase); OD450 (optical density, wavelength 450 nm); P116 cells (T cell line deficient for Syk and Zap-70); PDB ID (Protein Data Bank identification); RET (receptor tyrosine kinase); Ros1 (c-ros oncogene 1); Syk (Spleen tyrosine kinase); TKI (tyrosine kinase inhibitor); VEGFR (vascular endothelial growth factor receptor); WT (wild type); Z1-Z3, Z8-Z10 (ZAP-70 mutants experimental IDs); ZWT (ZAP-70 wild-type kinase)

Example 1: Selection of Kinase Inhibitors for use in Kinase Engineering

Different kinase inhibitors that are FDA-approved or are advanced in clinical trials can be used in a method of design of kinase mutants according to the invention. For example, the kinase ligand can be selected according to the following criteria:

agent which is FDA-approved or advanced in clinical trials, ensuring its possible use in human;

agent having little or no affinity for the wild-type target kinase (e.g. for ZAP-70 and/or Lck), ensuring that non-reprogrammed cells will not be affected by them;

agent having little cross-reactivity with other kinases than the foreign kinase (other than the target kinase), and limited known side effects;

agent having available experimentally determined binding mode to the foreign kinase they target, to ensure that this binding mode is compatible with a binding in the active site of the kinase to be mutated, i.e. to ensure that no large conformational change of the reprogrammed kinase is necessary to bind the selected kinase inhibitor;

agent bind to foreign kinase that have significant sequence differences in the active site compared to the target kinase, to ensure that the lack of binding in the wild-type target kinase to be reprogrammed is due to the presence of sub-optimal residues potentially to be engineered, rather than a to a conformational rearrangement.

Experimental structures of the kinase/inhibitor complexes from the Protein Data Bank (PDB) are collected (*Bermanet al.*, 2000, *Nucleic Acids Res.*, 28, 235-242) and for each inhibitor, it has been checked how many kinases it is known to bind to, with an affinity ($K_D$) (i) lower than 10 µM and (ii) lower than 100 nM, to estimate the selectivity profile (*Davis et al.*, 2011, *Nat. Biotechnol.*, 29: 1046-1051). The toxicity information is recorded based Toxicity Flags ACToR (EPA), the Material Safety Data Sheet (MSDS) of the FDA and DrugBank (*Wishart et al.*, 2006, *Nucleic Acids Res.*, 34, D668D672). Any known experimental affinity of each kinase inhibitors for the wild-type target kinase to be reprogrammed, e.g. ZAP-70 or Lck is retrieved. A first filtering is made on kinase inhibitors on this basis.

In the second step, all available experimental 3D structures of each kinase/kinase inhibitor complex from a short list obtained by a first filtering step is then superimposed to a list of representative experimental 3D structures of the wild-type kinases e.g. Zap-70 (PDB IDs: 1U59 and 2OZO) and Lck (PDB IDs: 3AD5, 3BYM, 3AC1, 2OF2).

Were retained only the kinase inhibitors for which binding in their targeted kinase (foreign kinase) does not require any significant conformational rearrangement of the latter compared to that of the target kinase for being mutated (e.g. Zap-70 or Lck), notably for the activation loop, the P-loop and the hinge domain. The kinase inhibitors whose primary target (foreign kinase) does not show any significant sequence difference in the active site compared to that of the target kinase to be mutated (e.g. Zap-70 or Lck) were excluded. These two criteria are necessary to ensure that the lack of binding of the kinase inhibitor to the wild-type target kinase is due to some residues that could be modified, and not to a global conformational change.

For Zap-70, the following kinase inhibitors were selected Afatinib, Erlotinib, Lapatinib, Neratinib and Vandetanib. For Lck, the following compounds were selected Afatinib, Erlotinib, Gefitinib and possibly Neratinib (Tables 2 and 3).

Example 2: Design and Characterization of Binding of Kinase Mutants

Several mutants of Zap-70 and Lck were designed according to the method of the invention and the binding free energy change for their binding to selected compounds was calculated.

Docking of Selected Kinase Inhibitors in Zap-70 and Lck

Kinase inhibitors selected after second step in Example 1 (step b) of the method of the invention for designing a kinase mutant) i.e. Afatinib, Erlotinib, Lapatinib, Neratinib, Vandetanib and Gefitinib were docked into the experimental 3D structure of Zap-70 and Lck, using the PDB files 1U59 and 3AD5, respectively. This allows verifying that the calculated binding mode, i.e. the position, conformation and orientation, of the ligand into the wild-type kinase, e.g. Zap-70 or Lck active sites is similar to the one observed experimentally for these kinase inhibitors in their respective primary target kinases, despite the lower affinity. This ensures that these small molecules have the potential to bind into the target wild-type kinase, e.g. Zap-70 and Lck in the binding modes they were developed for, and that a strong binding to Zap-70 or Lck can potentially be established by simple kinase mutations. Secondly, the calculated binding modes can be used to visually check the existing interactions between the ligand and the kinase, design kinase sequence modifications to enhance the binding, and finally to start the binding free energy estimations described below.

A consensus approach was used for the docking, which consists in using 3 different docking programs: Autodock 4.2 (Morris et al., 2008, Curr Protoc Bioinformatics, Chapter 8, Unit 8.14), Autodock Vina (Trott et al., 2009, J Comput Chem, 31: 455-461) and in house Attracting Cavities approach (Zoete et al. 2016, J Comput Chem, 37: 437-447) to verify the consistency of the predictions.

All approaches predicted a binding mode for these ligands in Zap-70 or Lck kinases similar to the one they have in their respective primary targets (foreign kinases).

Computer-Aided Design of Sequence Modifications of Target Kinases to Increase the Affinity for the Selected Kinase Inhibitors To design kinase mutants (steps c1) to c3) of the method of the invention for designing a kinase mutant), in particular Zap-70 and Lck kinase mutants, sequence modifications able to increase the affinity of the selected ligands (foreign kinase inhibitors) for these target kinases, a computer-aided protein engineering strategy similar to the strategy setup to design T-cell receptors with optimized affinities for cancer antigens was used as described in *Zoete et al.,* 2013, *supra*). This approach comprises:

1. estimating the total binding free energy, and the contribution of each residue, for the binding of the kinase inhibitor to the wild-type target kinase;
2. using this quantitative information, along with the predicted binding mode of the kinase inhibitor into the wild-type target kinase, to design potential sequence modifications of the wild-type kinase able to increase the affinity;
3. introducing virtually these mutations into the wild-type target kinase, and estimating the total binding free energy, and the contribution of each residue, for the binding of the kinase inhibitor to the mutated target kinase; and
4. comparing the binding free energy changes between the wild-type and mutated target kinase for the kinase inhibitor binding, to select for experimental assay the sequence modifications calculated to increase the affinity for the kinase inhibitor.

The absolute binding free energy for the inhibitor/kinase association was calculated using the Molecular Mechanics—Generalized Born Surface Area (MM-GBSA) approach (*Zoete et al.,* 2013, *supra; Zoete et al.,* 2005, *supra; Zoete et al.,* 2007, *supra; Zoete et al.,* 2010, *supra*). In MM-GBSA, the binding free energy, $\Delta G_{bind}$, is written as the sum of the gas phase contribution, $\Delta H_{bind}^{gas}$, the desolvation free energy of the system upon binding, $\Delta G_{desolv}$, and an entropic contribution, —TΔS:

$$\Delta G_{bind} = \langle \Delta H_{bind}^{gas} \rangle + \langle \Delta G_{desolv} \rangle - \langle T\Delta S \rangle$$

The brackets, ⟨ ⟩, indicate an average of these energy terms along a Molecular Dynamics (MD) simulation trajectory of the inhibitor/kinase complex. MD simulations, each 2 ns in length, were performed using the CHARMM (v36) program and the CHARMM27 force field, in explicit solvent using the TIP3P model for water molecules, at 300K. Stochastic boundary conditions (SBC) were used to restrain the water molecules around the protein. Energy terms were averaged over 200 frames regularly separated by 10 ps for each MD simulation, and were further averaged over 3 independent MD simulations. The entropy was neglected to save time and resources. It was demonstrated that the entropy term is useful to get a precise estimate of residue contribution to the binding, but is not mandatory for protein or peptide engineering (*Zoete et al.,* 2007, *supra*).

The gas-phase contribution to the binding free energy is equal to the sum of the van der Waals and electrostatic interaction energies between the ligand and the kinase, $\Delta H_{vdW}$ and $\Delta H_{elec}$. $\Delta G_{desolv}$ is the difference between the solvation free energy, $\Delta G_{solv}$, of the complex and that of the isolated parts (i.e. ligand and kinase taken separately). The solvation free energy, $\Delta G_{solv}$, is divided into the electrostatic, $\Delta G_{elec,solv}$, and the nonpolar, $\Delta G_{np,solv}$, contributions:

$$\Delta G_{solv} = \Delta G_{elec,solv} + \Delta G_{np,solv}. \quad (2)$$

$\Delta G_{elec,solv}$, which can be considered as the sum of a cavity term and a solute-solvent van der Waals term, is assumed to be proportional to the solvent accessible surface area, (SASA):

$$\Delta G_{np,solv} = \gamma SASA + b. \quad (3)$$

A value of 0.0072 kcal/(mol Å$^2$) for γ and 0 for b. The electrostatic contribution to the solvation free energy, $\Delta G_{elec,solv}$, was calculated using the analytical generalized Born (GB) GB-MV2 implicit solvent model (*Lee et al.,* 2003, *J Comput Chem,* 24: 1348-1356) implemented in CHARMM (Chemistry at Harvard Macromolecular Mechanics). The use of a GB equation not only reduces the computing time, but also allows one to decompose the electrostatic contribution to the binding free energy on a per-atom basis in a straightforward manner. This allows decomposing the binding free energy into contributions coming from each residue (Zoete et al., 2007, supra). According to previous research in protein engineering (Zoete et al., 2013, supra; Zoete et al., 2005, supra; Zoete et al., 2010, supra), it was found and applied that a better estimation of the effect of a mutation on the binding free energy is obtained by:

summing the contribution of the residue of interest with those of all residues in direct contact;

calculating this sum for the wild type system, $\Delta G_{bind,sum}^{wt}$, and the mutated system $\Delta G_{bind,sum}^{mutant}$, averaged along SBC simulations centered on the residue of interest (i.e. 6 MD simulations are thus performed for each mutant: 3 for the wild-type system and 3 for the mutated system);

calculating the difference between the mutated and wild-type systems:

$$\Delta\Delta G_{bind,sum} = \Delta G_{bind,sum}^{mutant} - \Delta G_{bind,sum}^{wt} \quad (4)$$

If $\Delta\Delta G_{bind,sum}$ is negative, than the mutation is expected to be favorable to the binding. All energy terms were calculated with CHARMM (v36).

Several mutations of Zap-70 and Lck were designed that are listed in Tables 2 to 3 along with the calculated binding free energy change upon mutation for several kinase inhibitors. The activity on the wild-type (ZWT) Zap-70/Lck is also given.

The designed mutations of Zap-70 and corresponding calculated binding free energy change ($\Delta\Delta G_{bind,sum}$) for the binding of Vandetanib or Erlotinib to Zap-70 are shown in Table 2 below.

TABLE 2

| Mutation in human Zap-70 | $\Delta\Delta G_{bind, sum}$ (kcal/mol) (Erlotinib) | $\Delta\Delta G_{bind, sum}$ (kcal/mol) (Vandetanib) | Compound |
|---|---|---|---|
| None (Wild-Type) | 0.0 | 0.0 | ZWT |
| M414A | −2.0 | −3.2 | Z1 |
| M414T | −3.8 | −1.5 | Z2 |
| M414V | −2.9 | −4.3 | Z3 |
| M414V/M416Y | −3.7 | −3.6 | Z8 |
| M414V/V399I | −3.0 | −3.3 | Z9 |
| M414V/M416Y/V399I | −3.8 | −4.5 | Z10 |

The designed mutations of Lck and corresponding calculated binding free energy change ($\Delta\Delta G_{bind,sum}$) for the binding of Gefitinib or Erlotinib (Table 3) to Lck are shown.

TABLE 3

| Mutation in human Lck | $\Delta\Delta G$ (kcal/mol) Erlotinib | $\Delta\Delta G_{bind, sum}$ (kcal/mol) Gefitinib | Compound |
|---|---|---|---|
| None (Wild-Type) | 0.0 | 0.0 | LWT |
| T316V | −5.0 | −5.1 | L7 |
| Y318L | −3.6 | −0.9 | L2 |
| S323C | −1.5 | +0.2 | LI |

This supports that a method of the invention allows designing sequence modification in a target kinase and predicting a binding strength of mutated kinase such as Zap-70 or Lck to specific kinase inhibitors.

Example 3: Expression of Kinase Mutants in T Cells

The expression profile of kinase mutants in T cells can be tested as follows, in particular Zap-70 mutants were tested to assess the expression of those mutants in this cell type.

Cell Line

The P116 T cell line deficient for Syk and Zap-70 was purchased from ATCC (Manassas, Va.) and were maintained in complete media (Roswell Park Memorial Institute (RPMI)-1640 medium supplemented with 10% heat-inactivated fetal bovine serum and penicillin-streptomycin, all from Gibco, Invitrogen).

Lentivirus Production and Cell Transduction Efficiency

Full-length codon optimized DNA encoding the Zap-70 mutants were cloned in the pRRL third generation lentiviral vector (Dull et al., 1998, J. Virol., 72: 8463-8471). Lentiviral vectors were produced by transient transfection of 293T cells using a standardized protocol for Lipofectamine 3000 (ThermoFisher Scientific). The P116 cells were transduced with fresh lentiviral supernatant and expression of the introduced Zap-70 mutants measured 2 weeks later, after antibiotic selection, by Western Blot.

Western Blotting

Transduction efficiency was determined from the lysates of transduced-P116 cells. Western blots were revealed with Zap-70 (Cell Signaling Technology) in 5% BSA-TBS (overnight at 4° C.) followed by polyclonal goat anti-rabbit horseradish peroxidase-labeled antibody (Cell Signaling Technology) for 1.5 h at room temperature, or with β-actin antibody (Santa Cruz) followed by polyclonal goat anti-mouse horseradish peroxidase-labeled antibody (Jackson ImmunoResearch). Membranes were revealed by chemiluminescence using the Fusion imaging system (Witec AG).

The expression of different Zap-70 mutants of the invention was assessed by Western Blot analysis on cell protein lysates after at least 2 weeks of culture in antibiotic selection condition to eliminate non-transduced cells. For Z1, Z2, Z3, Z8, Z9 and Z10 mutants, the expression was comparable to the WT form (FIG. 1). These results show that Zap-70 mutants can be expressed in T cells at the level of wild type Zap-70 kinase.

Example 4: T Cells Expressing Mutants of the Invention Produce IL-2

To assess the functionality of the T cells expressing mutants of the invention can be assessed through their ability of production of IL-2. The functionality of the T cells producing the Zap-70 mutants of the invention was tested in a cell-based assay as follows.

The used cell line, lentivirus production and cell transduction were as described in example 3.

Cell-Based Assays $10^5$ transduced P116 cells in microtiter plates coated were stimulated with 5 μg/ml anti-CD3 antibodies (OKT3) and stimulated with soluble anti-CD28 (CD28.2) mAbs for 24 h and 48 h at 37° C. and 5% CO2 in complete medium. IL-2 secretion was evaluated in the supernatant with the Max Set Deluxe Human IL-2 Elisa Kit (Biolegend) and measurement of the optical density (OD) at 450 nm.

Figure 2:
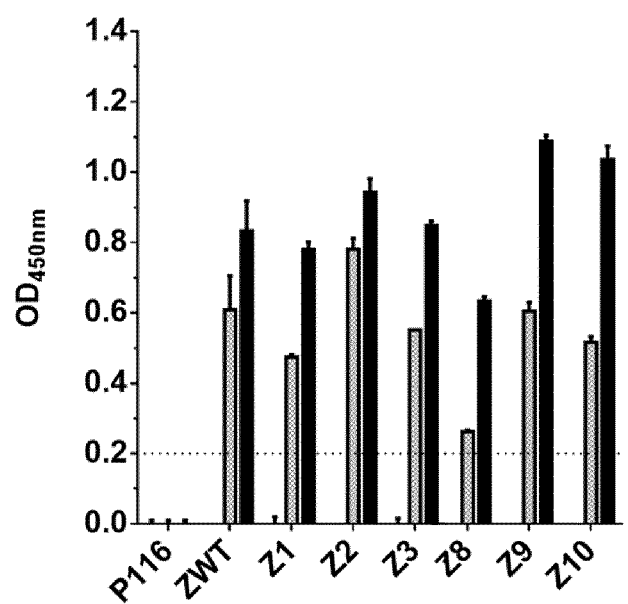
FIG. 2 shows IL-2 secretion after 24 h (grey bars) and 48 h (black bars) activation of Zap-70 mutants or Zap-70 wild-type (ZWT) transduced P116 cells, with anti-C3 and anti-CD8 antibodies and control (white bars), as described in Example 4.

The WT form of Zap-70 is able to restore IL-2 secretion after antibody stimulation while non-transduced P116 cells are not able to produce IL-2 upon activation (FIG. 2). For mutants of the invention Z1 to Z3 and Z8 to Z10, IL-2 production was comparable to the WT form of Zap-70 (FIG. 2).

These results demonstrate that expression of Zap-70 mutants of the invention in T cells deficient for Syk and Zap-70 can restore the T cell function of production of IL-2 and do not affect cells physiological responses.

Example 5: Specific Sensitivity to Inhibitory Agents, in Particular Tyrosine Kinase Inhibitors of T Cells Expressing Mutants In order to determine the sensitivity to inhibitory agents, in particular kinase inhibitors of T cells expressing kinase mutants of the invention, the cell viability of those T cells and their ability of production of IL-2 can be investigated in the presence of the specific kinase inhibitor for which the mutant has been reprogrammed as compared to those properties in absence of specific kinase inhibitor or in presence of a different kinase inhibitor. The sensitivity of T cells expressing Zap-70 mutants kinase of the invention were tested as follows.

The used cell line, lentivirus production and cell transduction were as described in example 3 and the cell-based assays used are those described in Example 4. The sensitivity of the Zap-70 mutants was investigated not only for the tyrosine kinase inhibitors (TKIs) for which those mutants were designed, Vandetanib and Erlotinib but also for other available ligands as listed in Table 4.

TABLE 4

| TKI | Formula | Known Foreign Kinase Targets |
|---|---|---|
| Afatinib | $C_{24}H_{25}ClFN_5O_3$ | EGFR, ErbB2 |
| CO-1686 | $C_{27}H_{28}F_3N_7O_3$ | EGFR |
| Crizotinib | $C_{21}H_{23}Cl_3FN_5O$ | ALK c-Met, HGFR EML Ros1 |
| Erlotinib | $C_{22}H_{24}ClN_3O_4$ | EGFR |
| Lapatinib | $C_{29}H_{26}ClFN_4O_4S$ | EGFR, ErbB2 |
| Neratinib | $C_{30}H_{29}ClN_6O_3$ | EGFR, ErbB2 |
| Vandetanib | $C_{22}H_{24}BrFN4O_2$ | EGFR, VEGFR, RET-tyrosine kinase |

Cell Viability

Following DMSO (negative control) or treatments with a kinase inhibitor, apoptotic cells were detected by 4',6-diamidino-2-phenylindole (DAPI) staining, which allowed identification of apoptotic nuclear change by fluorocytometry. Briefly, after 24 h of incubation cells were washed with PBS, re-suspended in PBS with 1 µg/mL DAPI and immediately analyzed using a BD LSR II cytometer. A 405 nm laser with 450/50 nm bandpass filter was used to collect data.

Figure 3:
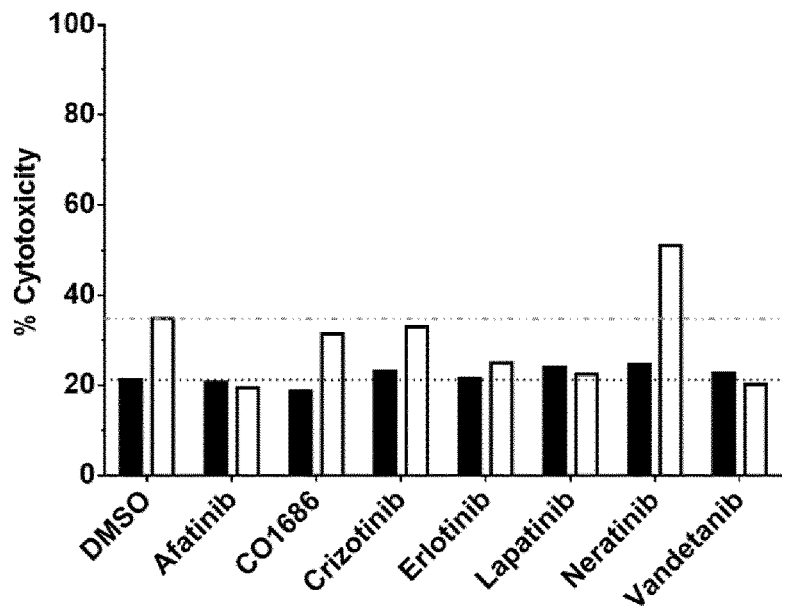
FIG. 3 shows percentage of WT Zap-70 transduced P116 dead cells after 24 h of antibody activation in presence of the Tyrosine Kinase Inhibitors (TKIs) at 2 concentrations (black bars: 500 nM; white bars: and 2.5 μM) or DMSO (control) as described in Example 5.
Figure 4:
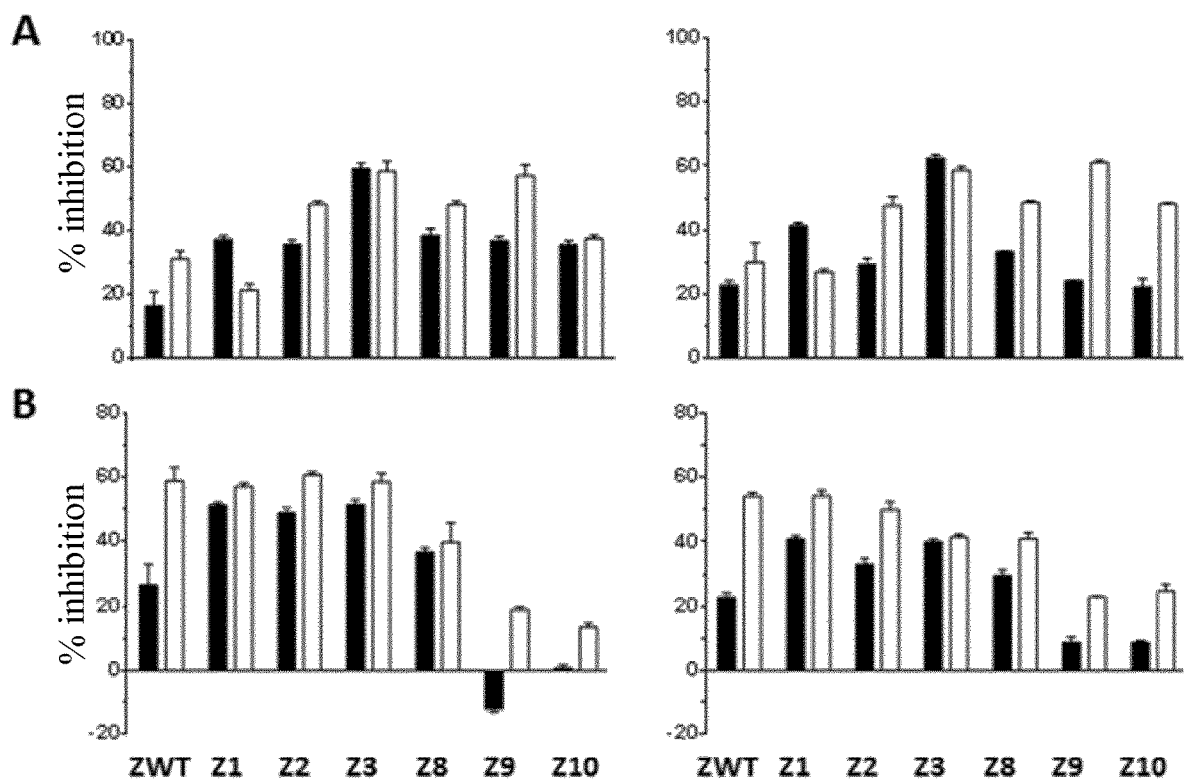
FIG. 4 shows percentage of inhibition of TKI compared to the control (DMSO) after 24 h (left panel) and 48 h (right panel) of culture upon stimulation with anti-CD3 and anti-CD28 antibodies as described in Example 5. A: Afatinib at 500 nM and 1 μM; B: CO-1686 at 500 nM and 1 μM; C: Crizotinib at 500 nM and 2.5 μM; D: Erlotinib at 500 nM and 2.5 μM; E: Lapatinib at 500 nM and 2.5 μM; F: Neratinib at 500 nM and 1 μM and G: Vandetanib at 500 nM and 1 μM; (black bars: 500 nM and white bars: 2.5 or 1 μM).
Figure 4:
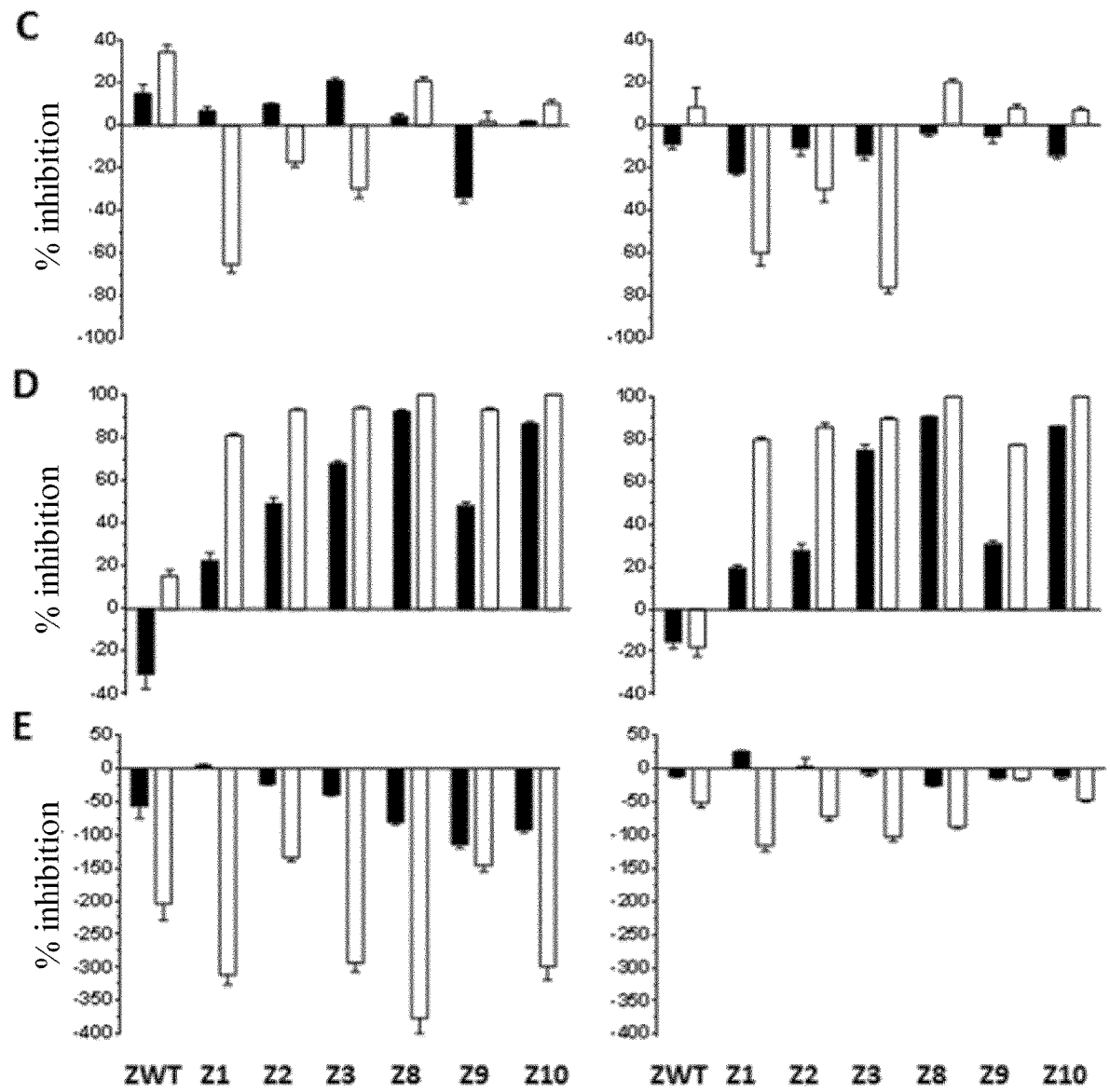
Figure 4:
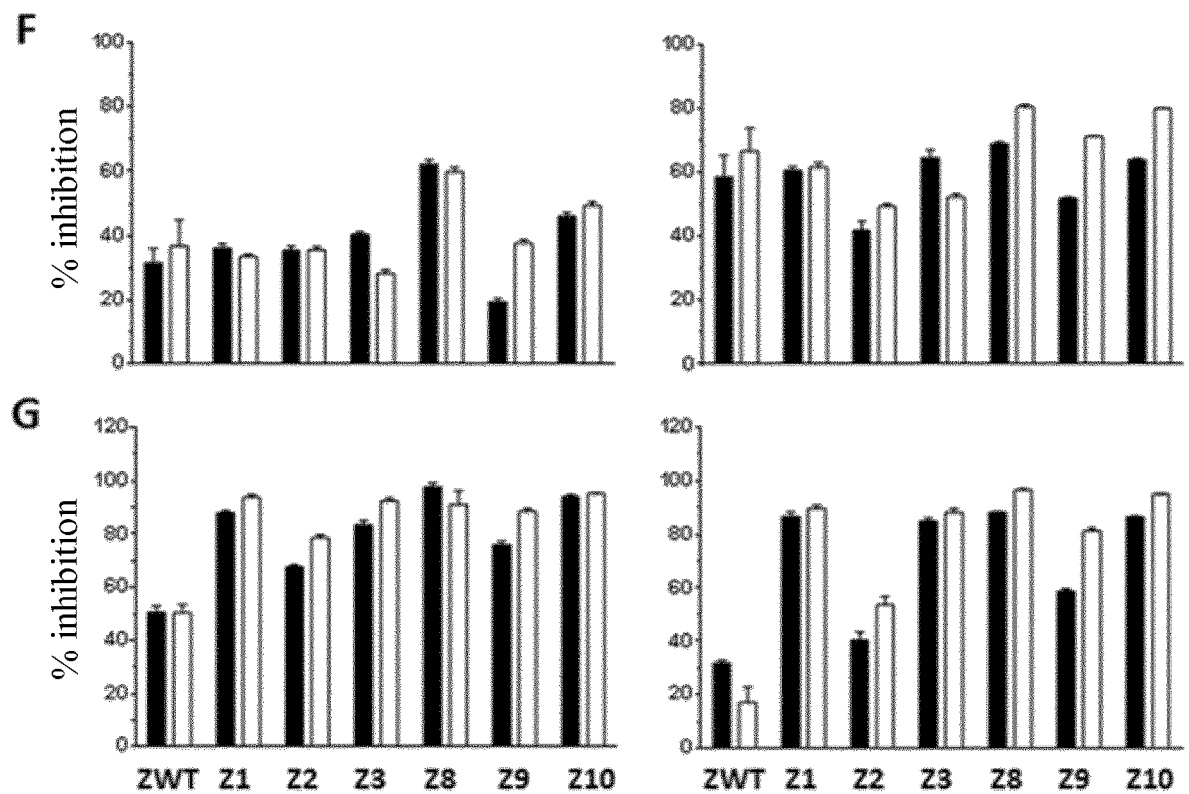
Figure 5:
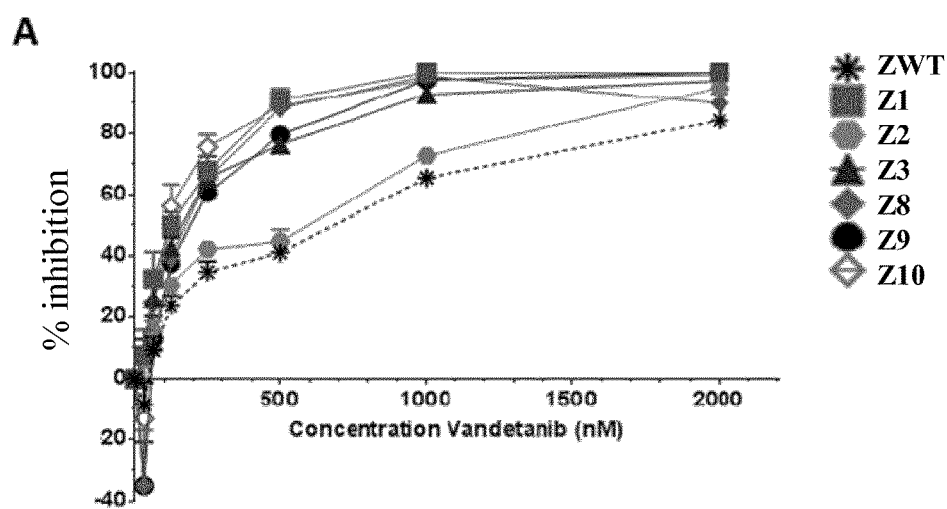
FIG. 5 shows dose-response curves of inhibition induced by Vandetanib (A, B) and Erlotinib (C, D) at 24 h (A, C) and 48 h (B, D) in P116 cells expressing wild Zap-70 type (ZWT) and mutants Z1, Z2, Z3, Z8, Z9 or Z10, after antibody stimulation (n=4) as described in Example 5.
Figure 5:
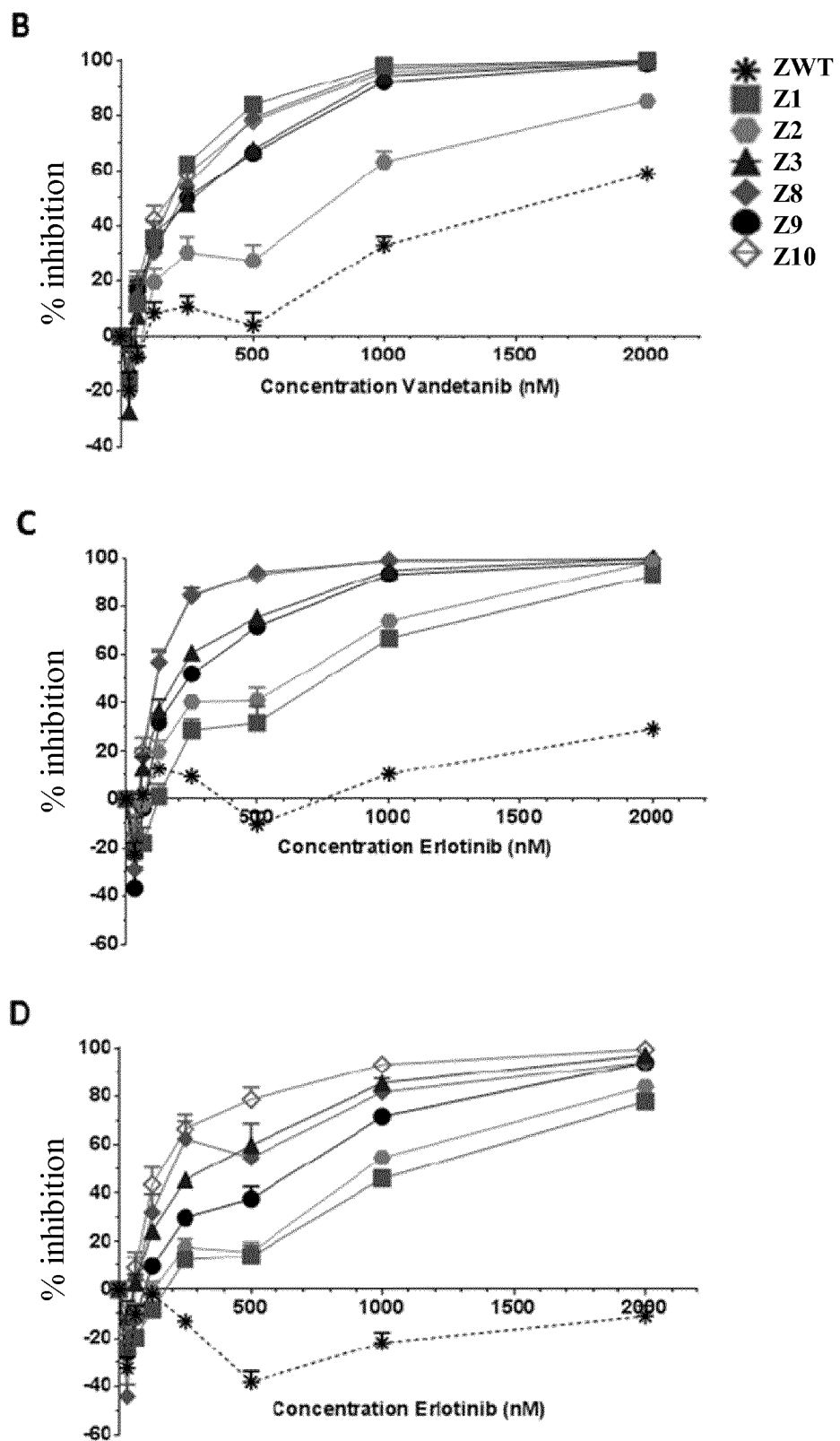

The inhibition of activation by TKIs was assessed by measuring their effect on cell viability (Table 5). After stimulation of WT Zap-70 transduced P116 cells, in presence or not of TKI, no cytotoxicity was observed for tested TKIs at 500 nM concentrations, only Neratinib induced cytotoxicity at 2.5 µM (FIG. 3). For the assessment of TKI, two concentrations of TKIs were used 500 nM and 1 or 2.5 µM. No significantly different inhibition in production of IL-2 was obtained with Afatinib, CO-1686 and Neratinib compared to the Zap-70 WT mutant (FIG. 4A, 4B, 4F), whereas Crizotinib and Lapatinib induced an increase of cell response (FIG. 4C, 4E). The inhibition was higher in mutants than WT with Erlotinib and Vandetanib (FIG. 4D, 4G) supporting the specific sensitivity of the mutants for the inhibitors for which they were designed by a method of the invention. The dose-response of these two inhibitors, i.e. Erlotinib and Vandetanib, clearly showed that mutants of Zap-70 of the invention are more sensitive to their to inhibition than the WT Zap-70 (FIG. 5), where Z1 and Z10 are the most sensitive mutants to Vandetanib and Z8 and Z10 to Erlotinib (FIG. 5 and Table 5). This is in line with the favorable modeled interactions between these ligands and the mutated residues in Z1 and Z10 for Vandetanib and Z8 and Z10 for Erlotinib. This is also in agreement with the calculated binding free energy changes (Table 2).

TABLE 5

| | $IC_{50}$ (nM) with Vandetanib | | $IC_{50}$ (nM) with Erlotinib | |
|---|---|---|---|---|
| | 24 h | 48 h | 24 h | 48 h |
| ZWT | 665 | 1660 | >2000 | >2000 |
| | | Mutants | | |
| Z1 | 125 | 195 | 775 | 1130 |
| Z2 | 600 | 820 | 640 | 940 |
| Z3 | 165 | 280 | 195 | 335 |
| Z8 | 180 | 230 | 110 | 200 |
| Z9 | 195 | 250 | 230 | 690 |
| Z10 | 110 | 180 | 110 | 170 |

For Z1 and Z10 mutants, there was a 5-6 fold decrease in IC50 of Vandetanib at 24 h (ZWT: 665 nM, Z1: 125 nM, Z10: 110 nM) and a 10-fold decrease at 48 h (ZWT: 1660 nM, Z1: 195 nM, Z10: 180 nM), as compared to the WT Zap-70 condition. For Z8 and Z10 mutants, there was more than 18 fold decrease in $IC_{50}$ of Erlotinib at 24 h (ZWT: >2000 nM, Z8: 110 nM, Z10:110 nM) and a 10 fold decrease at 48 h (ZWT: >2000 nM, Z8: 200 nM, Z10: 170 nM), as compared to the WT Zap-70 condition.

These results demonstrate that mutated Zap-70 kinases of the invention can be efficiently inhibited by specific TKI and that the inhibitory response of mutated Zap-70 kinases to TKI is increased as compared to wild type Zap-70.

Example 6: Binding of Lck Mutants to Gefitinib

The ability of Lck mutants to bind to the tyrosine kinase inhibitor (TKIs) for which those mutants were designed i.e., gefitinib was assessed as follows (Table 6):

TABLE 6

| Mutation in human Lck | Compound |
|---|---|
| None (Wild-Type) | LWT |
| S323C | L1 |
| S323C + Y318L | L4 |

The Lck mutants were produced and purified and used in a functional test as described below.

Cell Transfection and Protein Production

Full-length, codon-optimized DNAs encoding the Lck mutants, tagged with a c-Myc-tag (a polypeptide protein tag derived from the c-myc gene) at their N-terminal site, were cloned in an EBV (EBV promoter) promoter-based episome vector. Lck mutants were produced by transfection of 293T cells using a standardized protocol for Lipofectamine® 3000 (ThermoFisher Scientific). Expression of the introduced LcK mutants is measured by Western blot analysis.

Western Blot Analysis

Western blots are performed on the lysates of transfected-293T cells. Lck (c-myc tag labeled) was detected by anti-c-Myc antibody (clone 9E10) in 5% Milk-TBS (overnight at 4° C.) followed by polyclonal goat anti-mouse horseradish peroxidase-labeled antibody (Jackson ImmunoResearch) for 1.5 h at room temperature. As a control, β-actin was measured with an anti-β-actin antibody (Santa Cruz) followed by polyclonal goat anti-mouse horseradish peroxidase-labeled antibody (Jackson ImmunoResearch). Membranes are revealed by chemiluminescence using the Fusion imaging system (Witec AG).

Purification of Lck Mutants

Lck mutant purification was performed with μMACS c-myc Isolation Kit (Miltenyi Biotech), according to the manufacturer's instructions. Briefly, after lysis of the transfected 293T cells, c-myc-tagged Lck proteins were captured with μMACS magnetic anti-c-myc MicroBeads. The sample was loaded onto a MACS Column placed in the magnetic field of a μMACS separator in which the magnetically labeled c-myc-tagged and associated proteins are retained during the washing steps. The Lck proteins associated with anti-c-myc MicroBeads were eluted by removing the μColumn from μMacs Separator and adding elution buffer (50 mM Tris-HCl, pH 7.5, 150 mM NaCl, 0.25 mM DTT (dithiothreitol), 0.1 mM PMSF (phenylmethylsulfonyl fluoride), 10% glycerol, Halt protease inhibitory cocktail (ThermoFischer Scientific) and phosphatase inhibitory cocktail (Cell Signaling Technology)).

Functional Testing of Lck Mutants

The activity of Lck mutants as compared to wild-type Lck (LWT) was determined with the LCK Kinase Enzyme System (ADP-Glo™ Kinase Assay Family) from Promega, according to the manufacturer's instructions. Briefly, LWT and Lck mutants, in presence or not of increasing concentration of gefitinib, were incubated with substrate (ATP). After the kinase reaction, an equal volume of ADP-Glo™ Reagent was added to terminate the kinase reaction and deplete the remaining ATP. In the second step, the Kinase Detection Reagent was added, which simultaneously converts ADP to ATP and allows the newly synthesized ATP to be measured using a coupled luciferase/luciferin reaction. The luminescence was acquired on a SpectraMax Plus Microplate Reader (Molecular Devices). The percentages of inhibition and $IC_{50}$ of Lck mutants and LWT by gefitinib were derived therefrom. The experiment was performed 3 times and the result of trail 1, 2 and 3 as well as the pooled results (n=3) are shown in Table 7.

TABLE 7

| | $IC_{50}$ (nM) Gefitinib | | | |
|---|---|---|---|---|
| | trial 1 | trail 2 | trial 3 | n = 3 |
| LWT | >4000 | 7400 | 7900 | 7600 |
| Mutants | | | | |
| L1 | 2600 | 3200 | 3600 | 3200 |
| L4 | >4000 | 6200 | 8000 | 6900 |

Figure 6:
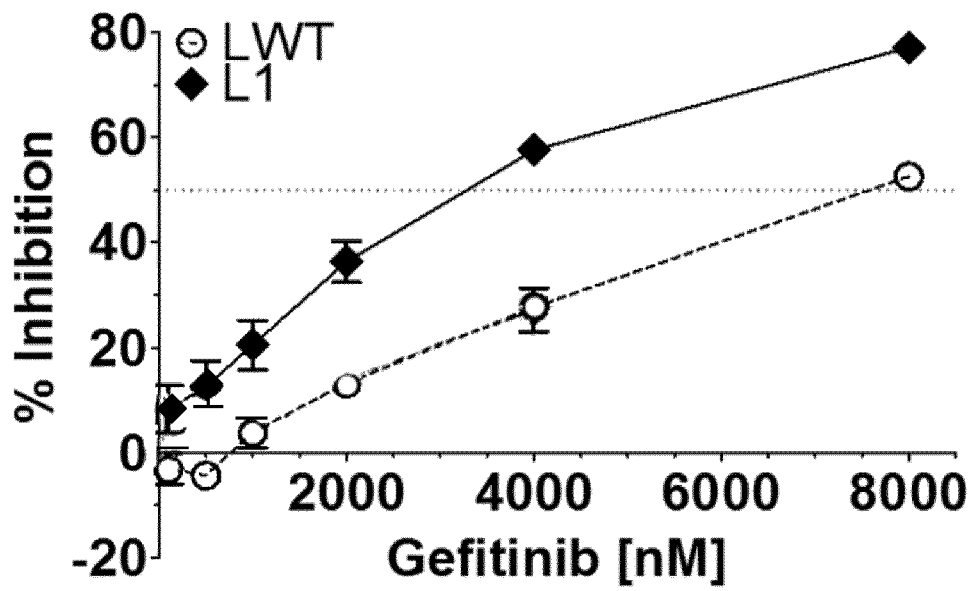
FIG. 6 shows dose-response curves of inhibition induced by Gefitinib on Lck type (LWT) and mutants L1 (A) or L4 (B) (n=3) as described in Example 6.
Figure 6:
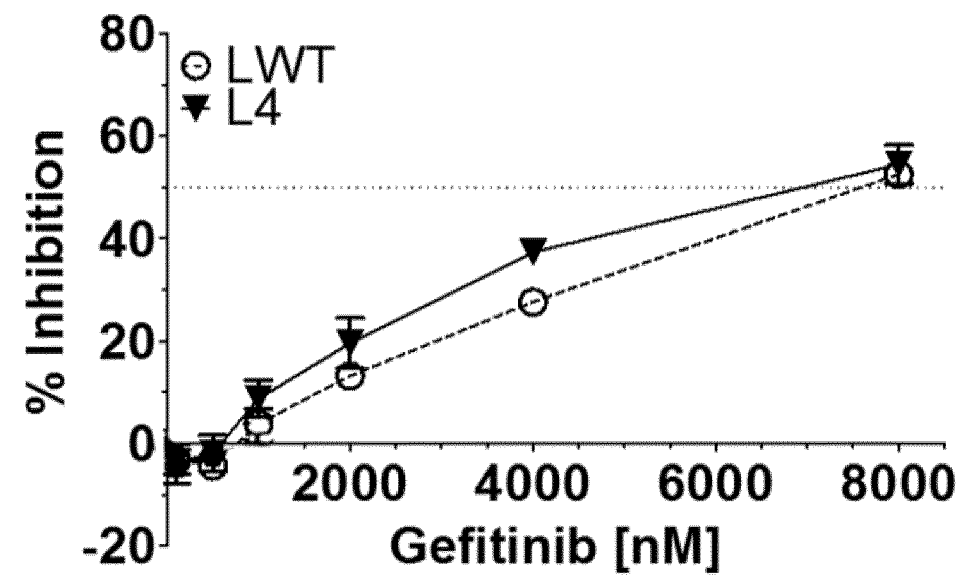

The dose-response of gefitinib, clearly showed that Lck mutants of the invention L1 and L4 are more sensitive than WT Lck, (FIG. 6). These results demonstrate that mutated Lck kinases of the invention can be efficiently inhibited by a specific TKI and that the inhibitory response of mutated Lck kinases to TKI is increased as compared to wild type Lck.

The invention claimed is:

1. A Zap-70 kinase mutant that retains functional activity of wild-type Zap-70 kinase and is more sensitive than wild-type Zap-70 kinase to inhibition by erlotinib and vandetanib, wherein said Zap-70 kinase mutant comprises an amino acid sequence of SEQ ID NO: 1 wherein is introduced at least one mutation selected from: V399I, M414A, M414T, M414V, M416Y, M416V, M416L, M416I, M416F, M416W, M416H, M416T and M416S.

2. The A Zap-70 kinase mutant that retains functional activity of wild-type Zap-70 kinase and is more sensitive than wild-type Zap-70 kinase to inhibition by erlotinib and vandetanib, wherein said Zap-70 kinase mutant comprises an amino acid sequence selected from SEQ ID NO: 3, SEQ ID NO: 4, SEQ ID NO: 5, SEQ ID NO: 6, SEQ ID NO: 7 and SEQ ID NO: 8.

3. The Zap-70 kinase mutant according to claim 1, said mutant comprising an amino acid sequence selected from SEQ ID NO: 5, SEQ ID NO: 6, SEQ ID NO: 7 and SEQ ID NO: 8.

4. The Zap-70 kinase mutant according to claim 1 comprising an amino acid sequence of SEQ ID NO: 1 wherein is introduced the mutation M414A, and at least one conservative substitution of at least one amino acid on at least one position selected from 342, 344-346, 350-354, 367-369, 386, 390, 399, 412, 413, 415-421, 424, 466-468 and 478-480.

5. A kit comprising at least one kinase mutant according to claim 1 and instructional material.

6. The Zap-70 kinase mutant of claim 1 further comprising at least one conservative substitution of at least one amino acid of the mutated SEQ ID NO: 1 on at least one position selected from 342, 344-346, 350-354, 367-369, 386, 390, 399, 412-421, 424, 466-468 and 478-480 which was not mutated.

* * * * *